# (12) United States Patent
Schafer et al.

(10) Patent No.: US 11,034,707 B2
(45) Date of Patent: Jun. 15, 2021

(54) GROUP 5 METAL COMPLEXES FOR CATALYTIC AMINE FUNCTIONALIZATION

(71) Applicant: THE UNIVERSITY OF BRITISH COLUMBIA, Vancouver (CA)

(72) Inventors: Laurel Schafer, Vancouver (CA); Sorin-Claudiu Rosca, Vancouver (CA); Rebecca Dipucchio, Vancouver (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 16/616,689

(22) PCT Filed: May 25, 2018

(86) PCT No.: PCT/CA2018/050619
§ 371 (c)(1),
(2) Date: Nov. 25, 2019

(87) PCT Pub. No.: WO2018/213938
PCT Pub. Date: Nov. 29, 2018

(65) Prior Publication Data
US 2020/0283459 A1 Sep. 10, 2020

Related U.S. Application Data

(60) Provisional application No. 62/511,725, filed on May 26, 2017.

(51) Int. Cl.
*C07F 9/00* (2006.01)
*B01J 31/16* (2006.01)
*C07C 11/02* (2006.01)

(52) U.S. Cl.
CPC ............. *C07F 9/00* (2013.01); *B01J 31/165* (2013.01); *C07C 11/02* (2013.01); *C07C 2531/12* (2013.01)

(58) Field of Classification Search
CPC .................................. C07F 9/00; C07F 9/005
See application file for complete search history.

(56) References Cited

U.S. PATENT DOCUMENTS 10,738,008 B2 * 8/2020 Anthis ..................... C23C 16/18
2006/0102895 A1 * 5/2006 Hendrix ............ H01L 23/53238
257/40

FOREIGN PATENT DOCUMENTS

WO WO 2012/040853 4/2012

OTHER PUBLICATIONS

Development of Group 4 and 5 complexes with N, O Chelating Supporting Ligands as Catalysts for the a-Alkylation of Amines.

Jean Michel Lauzon May 2013. Thesis for the degree of Doctor of Philosophy. Department of Chemistry, the University of British Columbia (Year: 2013).*
P. Eisenbergeretal., 82 Pure and Applied Chemistry, 1503-1515 (2010) (Year: 2010).*
M. Aresta et al., 39 Dalton Transactions, 6985-6992 (2010) (Year: 2010).*
R. DiPucchio et al., 57 Angewandte Chemie, International Edition, 3469-3472 (2018) (Year: 2018).*
E. Chong et al., 136, Journal of the American Chemical Society, 10898-10901 (2014) (Year: 2014).*
J. Clarkson et al., 56 Inorganic Chemistry, 5553-5566 (2017) (Year: 2017).*
M. Drew et al., 23 Journal of the Chemical Society, Dalton Transactions: Inorganic Chemistry, 2611-2617 (1975) (Year: 1975).*
A. Sarkar et al., 7 Metal-Based Drugs, 157-164 (2000) (Year: 2000).*
E. Chong et al., 46 Synthesis, 2884-2896 (2014) (Year: 2014).*
S. Ryken et al., Tight Bite Angle N,O-Chelates. Amidates, Ureates and Beyond, Ligand Design in Metal Chemistry: Reactivity and Catalysis (1st ed., M. Stradiotto et al., ed., 2016) (Year: 2016).*
Ackermann, L., "Metal-catalyzed direct alkylations of (hetero)arenes via C—H bond cleavages with unactivated alkyl halides" Chem. Commun. (2010) 46:4866-4877.
Brandt et al., "Ligand effects and kinetic investigations of sterically accessible 2-pyridonate tantalum complexes for hydroaminoalkylation" ACS Catal. (2017) 7:6323-6330.
Chen et al., "Palladium(II)-catalyzed C—H activation/C—C cross-coupling reactions: versatility and practicality" Angew. Chem. Int. Ed. (2009) 48:5094-5115.
Chisholm et al., "Chloro(dimethylamido) compounds of tantalum(V): Preparations, properties, and structures of $[Ta(NMe_2)_3Cl_2]_2$, $TaCl_3(NMe_2)_2(HNMe_2)$, $Ta(NMe_2)_3Cl_2(HNMe_2)$, and $[TaCl_2(NMe_2)_2(HNMe_2)]_2O$", Inorg. Chem.(1981) 20(6):1859-1866.
Chong et al., "2-Pyridonate tantalum complexes for the intermolecular hydroaminoalkylation of sterically demanding alkenes" J. Am. Chem. Soc. (2014) 136:10898-10901.
Clerici et al., "Catalytic C-alkylation of secondary amines with alkenes" Synthesis (1980):305-306.
Colby et al., "Rhodium catalyzed chelation-assisted C—H bond functionalization reactions" Acc. Chem. Res. (2012) 45(6):814-825.
Dörfler et al., "A commercially available tantalum catalyst for the highly regioselective intermolecular hydroaminoalkylation of styrenes" Eur. J. Org. Chem. (2014):2790-2797.

(Continued)

*Primary Examiner* — Alexander R Pagano
(74) *Attorney, Agent, or Firm* — Knobbe Martens Olson & Bear LLP

(57) ABSTRACT

This application pertains to group 5 metal complexes having the structure of Formula I:

(Formula I)

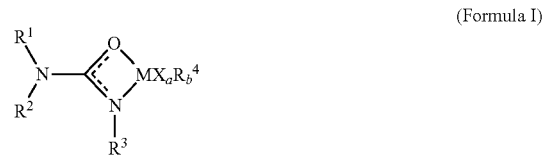

and their potential utility in catalyzing α-alkylation of secondary amine-containing moieties.

20 Claims, 25 Drawing Sheets

(56) References Cited

OTHER PUBLICATIONS

Edwards et al., "In situ generation of a regio- and diastereoselective hydroaminoalkylation catalyst using commercially available starting materials" Org. Lett. (2017) 19:5720-5723.
Eisenberger et al., "Tantalum-amidate complexes for the hydroaminoalkylation of secondary amines: enhanced substrate scope and enantioselective chiral amine synthesis" Angew. Chem. Int. Ed. (2009) 48:8361-8365.
Eisenberger et al., "Catalytic synthesis of amines and N-containing heterocycles: Amidate complexes for selective C—N and C—C bond-forming reactions" Pure Appl. Chem. (2010) 82(7):1503-1515.
Garcia et al., "Phosphoramidate tantalum complexes for room-temperature C—H functionalization: Hydroaminoalkylation catalysis" Angew. Chem. Int. Ed. (2013) 52:9144-9148.
Garcia et al., "Easily assembled, modular N,O-chelating ligands for Ta(V) complexation: a comparative study of ligand effects in hydroaminoalkylation with N-methylaniline and 4-methoxy-N-methylaniline" Tetrahedron (2013) 69:5737-5743.
Hamzaoui et al., "Solid-state NMR and DFT studies on the formation of well-defined silica-supported tantallaaziridines: From synthesis to catalytic application" Chem. Eur. J. (2016) 22:3000-3008.
Herzon et al., "Direct, catalytic hydroaminoalkylation of unactivated olefins with N-alkyl arylamines" J. Am. Chem. Soc. (2007) 129:6690-6691.
Herzon et al., "Hydroaminoalkylation of unactivated olefins with dialkylamines" J. Am. Chem. Soc. (2008) 130:14940-14941.
Lau, Y. Y., "Catalytic synthesis of N-heterocycles and alpha-alkylated amines by hydroamination and hydroaminoalkylation." Dec. 2016 PhD thesis. The University of British Columbia.
Lauzon et al., "Amidate complexes of tantalum and niobium for the hydroaminoalkylation of unactivated alkenes" ACS Catalysis (2017) 7:5921-5931.
Le et al., "Selective $sp^3$ C—H alkylation via polarity-match-based cross-coupling" Nature (2017) 547:79-83.
Lyons et al., "Palladium-catalyzed ligand-directed C—H functionalization reactions" Chem. Rev. (2010) 110:1147-1169.
Moorhouse et al., "Bis[(trimethylsilyl)methyl]- and bis(neopentyl)-zinc, and tris[(trimethylsilyl)methyl]aluminium-diethyl ether (1/1); their use as alkylating agents in forming niobium and tantalum alkyls" J. Chem. Soc., Dalton Trans. (1974):2187-2190.
Nugent et al., "Catalytic C—H activation in early transition-metal dialkylamides and alkoxides" Organometallics (1983) 2:161-162.
Oda et al., "Diene hydroaminomethylation via ruthenium-catalyzed C—C bond forming transfer hydrogenation: beyond carbonylation" Chem. Sci. (2016) 7:136-141.
Payne et al., "Tantalum Catalyzed Hydroaminoalkylation for the Synthesis of alpha- and beta-Substituted N-Heterocycles" Org. Lett. (2013) 15(9):2182-2185.
Pelletier et al., "Catalysis by design: Well-defined single-site heterogeneous catalysts" Acc. Chem. Res. (2016) 49:664-677.
Perez et al., "Ruthenium-catalyzed transfer hydrogenation for C—C bond formation: Hydrohydroxyalkylation and hydroaminoalkylation via reactant redox pairs" Top. Curr. Chem. (2016) 374(3):35.
Perry et al., Catalytic synthesis of secondary amine-containing polymers: Variable hydrogen bonding for tunable rheological properties, Macromolecules (2016) 49(12):4423-4430.
Perry, M. R., "Catalytic synthesis of amines: From small molecules to nitrogen-containing polymers", 2017, PhD Thesis, The University of British Columbia.
Reznichenko et al., "Group 5 metal binaphtholate complexes for catalytic asymmetric hydroaminoalkylation and hydroamination/cyclization" Organometallics (2011) 30:921-924.
Reznichenko et al., "The mechanism of hydroaminoalkylation catalyzed by group 5 metal binaphtholate complexes" J. Am. Chem. Soc. (2012) 134:3300-3311.
Roesky, P. W., "Catalytic hydroaminoalkylation" Angew. Chem. Int. Ed. (2009) 48:4892-4894.
Ryken et al., "N,O-Chelating four-membered metallacyclic titanium (IV) complexes for atom-economic catalytic reactions" Acc. Chem. Res. (2015) 48:2576-2586.
Ryken et al. Chapter 13. Tight Bite Angle N,O-chelates. Amidates, Ureates and Beyond. Ligand Design in Metal Chemistry: Reactivity and Catalysis. First Edition. Edited by Mark Stradiotto 2016 John Wiley and Sons.
Sattler et al., "Structural characterization of $TaMe_3Cl_2$ and $Ta(PMe_3)_2Me_3Cl_2$, a pair of five and seven-coordinate d0 tantalum methyl compounds", Dalton Trans. (2011) 40:7777-7782.
Schrock et al., "Multiple metal-carbon bonds. 7. Preparation and characterization of $Ta(\eta^5\text{-}C_5H_5)_2(CH_2)(CH_3)$, a study of its decomposition, and some simple reactions" J. Am. Chem. Soc. (1978) 100(8):2389-2399.
Schrock et al., "Multiple metal-carbon bonds. 8. Preparation, characterization, and mechanism of formation of the tantalum and niobium neopentylidene complexes, $M(CH_2CMe_3)_3(CHCMe_3)$" J. Am. Chem. Soc. (1978) 100:3359-3370.
Thullen et al., "A mild hydroaminoalkylation of conjugated dienes using a unified cobalt and photoredox catalytic system" J. Am. Chem. Soc. (2017) 139:15504-15508.
Tran et al., "Practical alkoxythiocarbonyl auxiliaries for iridium(I)-catalyzed C—H alkylation of azacycles" Angew. Chem. Int. Ed. (2017) 56:10530-10534.
Yamauchi et al., "Hydroxoiridium-catalyzed hydroalkylation of terminal alkenes with ureas by $C(sp^3)$—H bond activation" Angew. Chem. Int. Ed. (2017) 56:7200-7204.
Zhang et al., "Synthesis and catalytic activity of group 5 metal amides with chiral biaryldiamine-based ligands" Dalton Trans. (2011) 40:1547-1566.
Zhang et al., "$TaMe_3Cl_2$-catalyzed intermolecular hydroaminoalkylation: A simple complex for enhanced reactivity and expanded substrate scope" Chem. Eur. J. (2013) 19:8751-8754.
Zi et al., "Highly enantioselective hydroaminoalkylation of secondary amines catalyzed by group 5 metal amides with chiral biarylamidate ligands" Chem. Comm. (2010) 46:6296-6298.

* cited by examiner

GROUP 5 METAL COMPLEXES FOR CATALYTIC AMINE FUNCTIONALIZATION

INCORPORATION BY REFERENCE TO RELATED APPLICATIONS

Any and all priority claims identified in the Application Data Sheet, or any correction thereto, are hereby incorporated by reference under 37 CFR 1.57. This application is the national phase under 35 U.S.C. § 371 of prior PCT International Application No. PCT/CA2018/050619 which has an International Filing Date of May 25, 2018, which designates the United States of America, and which claims priority to U.S. Provisional Application No. 62/511,725 filed May 26, 2017, the disclosures of which are hereby expressly incorporated by reference in their entirety and are hereby expressly made a portion of this application.

FIELD OF THE INVENTION

This disclosure relates to the use of group 5 metal complexes for amine functionalization and synthetic process for manufacture thereof.

BACKGROUND

The catalytic functionalization of alkenes represents a sustainable and efficient method for the synthesis of molecules that are relevant for the chemical, pharmaceutical, and agrochemical industry. Such organic transformations are attractive as valuable building blocks, which are obtained economically from relatively inexpensive starting materials. Notably, the direct C—H functionalization of amines with alkenes, or hydroaminoalkylation, has gained notoriety due to the fact that polysubstituted amines can now be easily obtained in the absence of any protecting/directing groups or photoinitiators.[1]

It is known in the art that group 3 (Sc), 4 (Ti, Zr), and 5 (Nb, Ta) metal complexes may serve as powerful precatalysts in hydroaminoalkylation reactions. For example, N,O-chelated pyridonate tantalum based complexes were shown capable of reacting with sterically demanding internal alkenes and facilitate their reaction with secondary anilines. These reactions occurred in a 100% regioselective manner to give the branched products.

Despite the high demand of simple and economical methods for synthesis of amine building blocks in the chemical, pharmaceutical, and agrochemical industry, there are known issues with the catalytic systems presently in use. For instance, hydroaminoalkylation often requires high reaction temperatures (>110° C.) and quite long reaction times (>20 h), which many catalysts are not robust enough to tolerate. Moreover, substrate compatibility of these catalysts is known to be problematic, especially for internal alkenes such as cyclohexene and cyclooctene. The fact that excess alkene (at least 1.5 equivalents excess) is needed to achieve full substrate conversion remains a challenge as well.

In the case of the catalytic systems, where the active species have a Ta—$NMe_2$ moiety, the excess alkene is often justified by the deleterious side reactions between the released $HNMe_2$ and the alkene reagents, thereby affecting the stoichiometry of the reaction. The use of $TaMe_3Cl_2$ proved to be successful, as hydroaminoalkylations of amine and alkene substrates was achieved using this catalyst in stoichiometric amounts, but with the caveat that $TaMe_3Cl_2$ is light and temperature sensitive and therewith not suitable for large scale industrial processes. Using a similar approach, the addition of 1-octene to 4-methoxy-N-methylaniline at room temperature was achieved with a phosphoramidate supported Ta-Me complex as the catalyst. Although this catalyst demonstrated high reactivity, the phosphoramidate Ta-Me complex actually required excess alkene in order to fully convert the substrates. To improve the stability of early transition metal complexes, steric bulk in the form of e.g. bulky alkyl groups, such as for example $CH_2SiMe_3$ and $CH_2CMe_3$, may be complexed to the metal centre. Earlier, Wilkinson and Schrock have described the alkyl tantalum complexes $Ta(CH_2SiMe_3)_3Cl_2$ and $Ta(CH_2CMe_3)_3Cl_2$. However, their activity in hydroaminoalkylation reactions has not been reported in the art.

SUMMARY OF THE INVENTION

This disclosure is based in part on the discovery of group 5 metal complexes that are advantageous for catalyzing hydroaminoalkylation reactions. In particular, the present invention relates disclosure relates to group 5 metal complexes and their use for amine functionalization, as well as synthetic processes for manufacturing such complexes. The group 5 metal complexes described herein may catalyze hydroaminoalkylation reactions at stoichiometric ratios of N-containing heterocycle to alkene and at lower reaction temperatures than those reported in the art.

Aspects of this disclosure relate to a metal complex having the structure of Formula I:

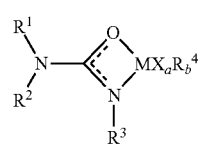

(Formula I)

wherein:

$R^1$ and $R^2$ are:
  each independently: H; a $C_1$-$C_{40}$ substituted or unsubstituted linear, branched or cyclic alkyl or alkenyl or alkynyl; a substituted or unsubstituted aryl; or a substituted or unsubstituted heterocyclic group; or
  bonded together thereby forming, together with the nitrogen atom they are both bound to, a heterocycle;

$R^3$:
  is H; a $C_1$-$C_{40}$ substituted or unsubstituted linear, branched or cyclic alkyl or alkenyl or alkynyl; or a substituted or unsubstituted aryl; or a substituted or unsubstituted heterocyclic group; or
  bonded together with $R^1$ and/or $R^2$ to form a heterocycle.

M is a group 5 metal;
a=0 to 4 and b=0 to 4, wherein the sum of a and b is 4;
each X is a halogen substituent;
each $R^4$ is independently: H; or a $C_1$-$C_{20}$ substituted or unsubstituted, linear, branched or cyclic alkyl, optionally comprising heteroatoms.

Each X is independently Cl or Br. IN various embodiments, a may be 1 or 2.

$R^1$ and $R^2$ may each independently be: methyl; ethyl; isopropyl; cyclohexyl; phenyl; 2,6-dimethyl phenyl; 2,4,6-trimethyl phenyl; 4-methyl phenyl; optionally substituted piperidine; optionally substituted pyrrolidine; or substituted morpholine.

Alternatively, $R^1$ and $R^2$ may be bonded together to form, together with the nitrogen atom they are both bound to, a 6-membered ring, which optionally may be substituted.

In various embodiments, $R^1$ and $R^2$ are each phenyl. In various embodiments, $R^1$ is phenyl and $R^2$ is isopropyl. In various embodiments, $R^1$ and $R^2$ are bonded together to form, together with the nitrogen atom they are both bound to, piperidinyl. In various embodiments, $R^1$ is phenyl and $R^2$ is methyl; $R^1$ is methyl and $R^2$ is 1-phenylethyl; In various embodiments, $R^1$ is methyl and $R^2$ is isopropyl; In various embodiments, $R^1$ is phenyl and $R^2$ is diphenylmethyl.

$R^3$ may be: phenyl; 2,6-dimethyl phenyl; 2,6-di(isopropyl) phenyl; or

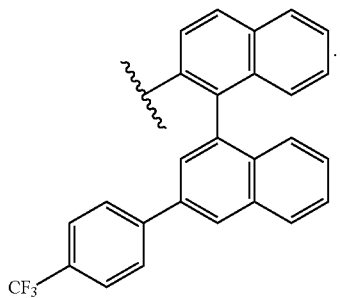 [SMILES: *c1ccc2ccccc2c1-c1cc(-c2ccc(C(F)(F)F)cc2)cc2ccccc12]

$R^3$ may be bonded together with $R^1$ and/or $R^2$ to form, together with each of the nitrogen atoms they are bound to, a 5-membered ring, which optionally may be substituted. $R^3$ may be bonded together with $R^1$ and/or $R^2$, and each of the nitrogen atoms they are bound to, to form:

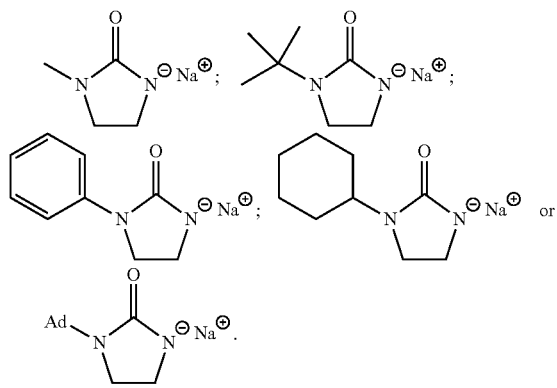

$R^4$ may be —CH$_3$, —NMe$_2$, —CH$_2$C(CH$_3$)$_3$, or —CH$_2$Si(CH$_3$)$_3$.

M may be tantalum (Ta), niobium (Nb), or vanadium (V).

Aspects of this disclosure further related to a metal complex having the structure of Formula II

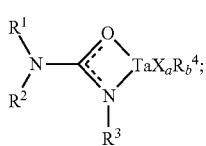

(Formula II)

wherein:

$R^1$ and $R^2$ are:

each independently: methyl; ethyl; isopropyl; cyclohexyl; phenyl; 2,6-dimethyl phenyl; 2,4,6-trimethyl phenyl; 4-methyl phenyl; optionally substituted piperidine; optionally substituted pyrrolidine; or substituted morpholine; or bonded together to form, together with the nitrogen atom they are both bound to, a 6-membered ring, which optionally may be substituted;

$R^3$ is:

phenyl; 2,6-dimethyl phenyl; or 2,6-di(isopropyl) phenyl; or bonded together with $R^1$ and/or $R^2$ to form, together with each of the nitrogen atoms they are bound to, a 5-membered ring, which optionally may be substituted;

each X is independently Cl or Br;

a=1 or 2 and b=(4−a); and $R^4$ is —CH$_3$, —NMe$_2$, —CH$_2$C(CH$_3$)$_3$, or —CH$_2$Si(CH$_3$)$_3$.

Aspects of the disclosure related to a metal complex, which metal complex is:

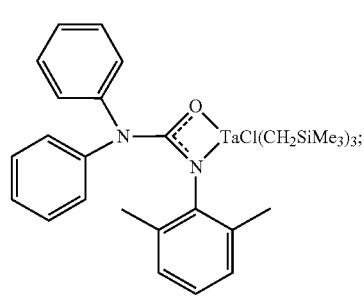

(Formula III)

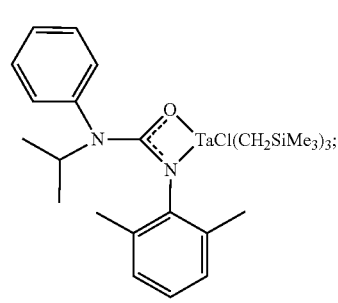

Formula (IV)

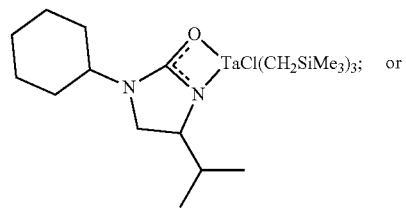

(Formula V)

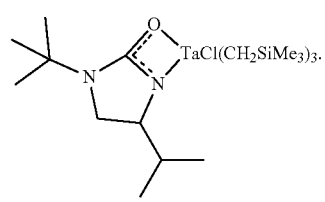

(Formula VI)

Aspects of this disclosure relate to a catalyst comprising a metal complex as defined above and elsewhere herein Aspects of this disclosure relate to a catalyst kit comprising at least one metal complex as defined above and elsewhere herein and a quenching agent. The quenching agent may include an alcohol, water, or a combination thereof.

Aspects of this disclosure relate to a method of synthesizing a metal complex of Formula I, the method comprising reacting a group 5 metal salt of Formula VII with one equivalent of an amide of Formula VIII according to the following reaction:

$$MX_cR^4{}_d \;+\; \underset{\text{Formula VIII}}{\begin{array}{c}R^1\\ \diagdown\\ N\\ \diagup\\ R^2\end{array}\!\!-\!\!\overset{O}{\underset{\ominus}{C}}\!\!-\!\!\underset{R^3}{N}} \;\longrightarrow\; \underset{\text{Formula I}}{\begin{array}{c}R^1\\ \diagdown\\ N\\ \diagup\\ R^2\end{array}\!\!-\!\!\overset{O}{C}\!\!=\!\!\underset{R^3}{N}\!-\!MX_aR_b^4}$$

Formula VII    Formula VIII    Formula I wherein:

$R^1$ and $R^2$ are:
- each independently: H; a $C_1$-$C_{40}$ substituted or unsubstituted linear, branched or cyclic alkyl or alkenyl or alkynyl; a substituted or unsubstituted aryl; or a substituted or unsubstituted heterocyclic group; or
- bonded together thereby forming, together with the nitrogen atom they are both bound to, a heterocycle;

$R^3$:
- is H; a $C_1$-$C_{40}$ substituted or unsubstituted linear, branched or cyclic alkyl or alkenyl or alkynyl; or a substituted or unsubstituted aryl; or a substituted or unsubstituted heterocyclic group; or
- bonded together with $R^1$ and/or $R^2$ to form a heterocycle.

M is a group 5 metal;

a=0 to 4 and b=0 to 4, wherein the sum of a and b is 4;

c=1 to 5 and d=0 to 4, wherein the sum of c and d is 5;

each X is a halogen substituent;

each $R^4$ is independently: H; or a $C_1$-$C_{20}$ substituted or unsubstituted, linear, branched or cyclic alkyl, optionally comprising heteroatoms.

X may be, independently, Cl or Br. In various embodiments, a may be 1 or 2.

$R^1$ and $R^2$ may each independently be: methyl; ethyl; isopropyl; cyclohexyl; phenyl; 2,6-dimethyl phenyl; 2,4,6-trimethyl phenyl; 4-methyl phenyl; optionally substituted piperidine; optionally substituted pyrrolidine; or substituted morpholine.

Alternatively, $R^1$ and $R^2$ may be bonded together to form, together with the nitrogen atom they are both bound to, a 6-membered ring, which optionally may be substituted.

In various embodiments, $R^1$ and $R^2$ are each phenyl. In various embodiments, $R^1$ is phenyl and $R^2$ is isopropyl. In various embodiments, $R^1$ and $R^2$ are bonded together to form, together with the nitrogen atom they are both bound to, piperidinyl. In various embodiments, $R^1$ is phenyl and $R^2$ is methyl; $R^1$ is methyl and $R^2$ is 1-phenylethyl; In various embodiments, $R^1$ is methyl and $R^2$ is isopropyl; In various embodiments, $R^1$ is phenyl and $R^2$ is diphenylmethyl.

$R^3$ may be: phenyl; 2,6-dimethyl phenyl; 2,6-di(isopropyl) phenyl; or

[structure of binaphthyl group substituted with 4-(trifluoromethyl)phenyl, with $CF_3$ label]

$R^3$ may be bonded together with $R^1$ and/or $R^2$ to form, together with each of the nitrogen atoms they are bound to, a 5-membered ring, which optionally may be substituted. $R^3$ may be bonded together with $R^1$ and/or $R^2$, and each of the nitrogen atoms they are bound to, to form:

[five imidazolidinone-type structures with N$^\ominus$Na$^\oplus$ groups: N-methyl, N-tert-butyl, N-phenyl, N-cyclohexyl, and N-adamantyl (Ad)]

$R^4$ may be —$CH_3$, —$NMe_2$, —$CH_2C(CH_3)_3$, or —$CH_2Si(CH_3)_3$.

M may be tantalum (Ta), niobium (Nb), or vanadium (V).

In various embodiments, the reaction may be performed in a temperature range from −30° C. to ambient temperature.

In various embodiments, the reaction is performed at ambient temperature. Ambient temperature may be room temperature.

The reaction may be performed in an organic solvent. The organic solvent may be toluene or hexane.

In various embodiments, the method may include a further reaction step that is performed in situ.

Aspects of the disclosure relate to a method for α-alkylation of a secondary amine-containing moiety, the method comprising: (i) reacting said secondary amine-containing moiety with an olefin in the presence of a metal complex as defined above and elsewhere herein. The method may further include isolating a product formed in step (i).

The secondary amine-containing moiety may include at least two α-spa hybridized C—H bonds.

The secondary amine-containing moiety may be a $C_4$-$C_{100}$ linear, branched, or cyclic alkyl, optionally substituted and/or comprising heterotaoms. The secondary amine-containing moiety may be substituted with a halogen, an ether, another amine, an alkyl, an alkene, an acetal, a phosphine, an amide, an alkyne, an imine, a nitrile, an isocyanide, an epoxide, a boronic acid ester; a phenyl that optionally may be substituted and/or part of a condensed ring system, or any combination thereof.

The olefin may include from 2 to 100 carbon atoms. In various embodiments, the olefin comprises an internal alkene. In various embodiments, the olefin is a linear or a cyclic olefin. In various embodiments, the olefin comprises a terminal alkene. In various embodiments, the olefin is an optionally substituted 1-alkene or an optionally substituted cycloalk-1-ene. In various embodiments, the olefin comprises one or more protected functional group(s). In various embodiments, the olefin is:

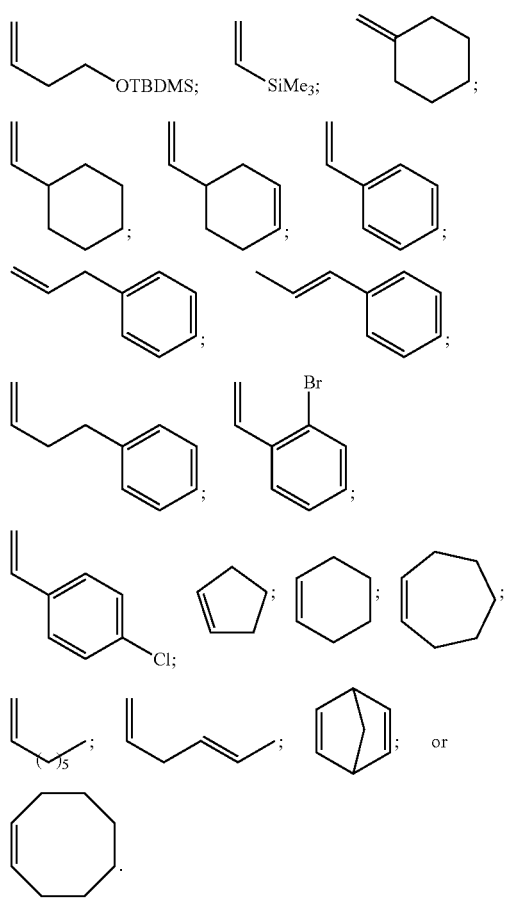

The secondary amine-containing moiety may be: pyrrolidine; piperidine;

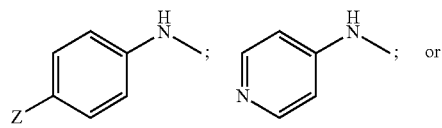

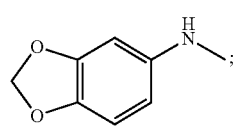

wherein Z is H, OCF$_3$, F, Cl, Br, I, or OCH$_3$.

The secondary amine-containing moiety may be:

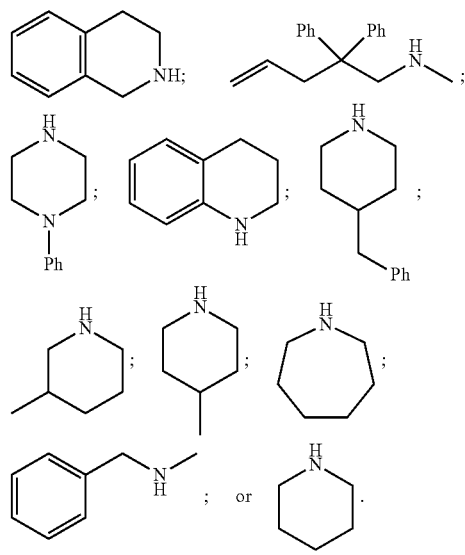

The reaction conditions may include a reaction temperature in the range from 50° C. to 200° C., a reaction temperature in the range from 75° C. to 165° C., a reaction temperature in the range from 90° C. to 150° C., a reaction temperature in the range from range from 110° C. to 130° C., a reaction temperature of about 110° C., or a reaction temperature of about 130° C.

The reaction conditions may include a solvent. The solvent may be non-protic. The solvent may be toluene, benzene, or a mixture thereof.

The secondary amine-containing moiety and said olefin may be provided in a stoichiometric ratio from 0.1 to 1.5. The secondary amine-containing moiety and said olefin may be provided in a stoichiometric ratio of about 1:1.

Aspects of the disclosure relate to a method of synthesizing a pharmaceutical compound or an agrochemical compound, the method comprising α-alkylation of a secondary amine-containing moiety according to a method as defined above and elsewhere herein.

Aspects of the disclosure relate to use of a group 5 metal salt of Formula VII $$MX_cR^4_d \qquad \text{(Formula VII)}$$

wherein:
M is a group 5 metal;
c=1 to 5 and d=0 to 4, wherein the sum of c and d is 5; and
each $R^4$ is independently: H; or a $C_1$-$C_{20}$ substituted or unsubstituted, linear, branched or cyclic alkyl, optionally comprising heteroatoms,
in combination with an amide of Formula VIII

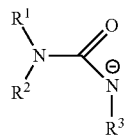

(Formula VIII)

wherein:

R¹ and R² are:
  each independently: H; a $C_1$-$C_{40}$ substituted or unsubstituted linear, branched or cyclic alkyl or alkenyl or alkynyl; a substituted or unsubstituted aryl; or a substituted or unsubstituted heterocyclic group; or
  bonded together thereby forming, together with the nitrogen atom they are both bound to, a heterocycle; and R³:
  is H; a $C_1$-$C_{40}$ substituted or unsubstituted linear, branched or cyclic alkyl or alkenyl or alkynyl; a substituted or unsubstituted aryl; or a substituted or unsubstituted heterocyclic group; or
  bonded together with R¹ and/or R² to form a heterocycle.

for generating a catalyst for α-alkylation of a secondary amine-containing moiety.

The catalyst may be a metal complex of Formula I,

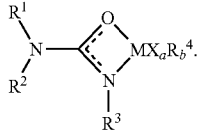

Formula I wherein a=0 to 4 and b=0 to 4, wherein the sum of a and b is 4.

In various embodiments, α-alkylation of a secondary amine-containing moiety comprises reacting said secondary amine-containing moiety with an olefin in the presence of the catalyst. The secondary-amine containing moiety and/or olefin may be as defined above and elsewhere herein.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION

Definitions

Figure 1:
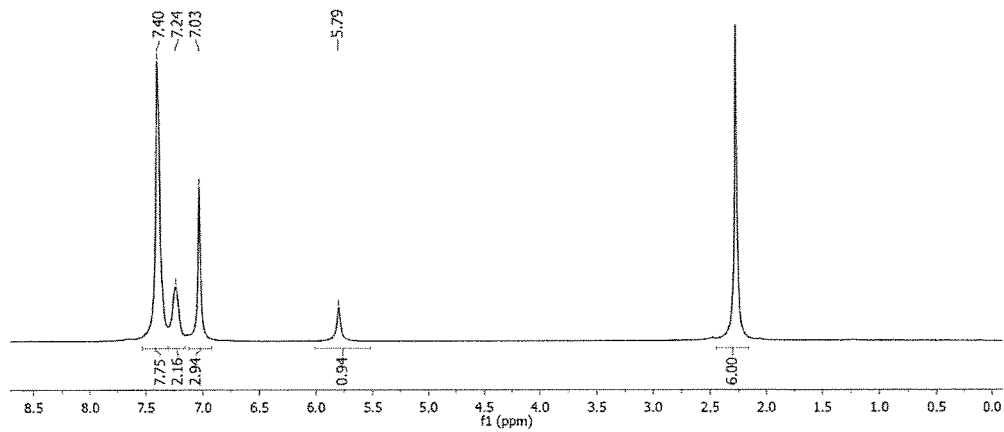
FIG. 1 is a ¹H NMR spectrum (300 MHz, CDCl₃, 298 K) of 3-(2,6-dimethylphenyl)-1,1-diphenylurea.

"Catalyst", as used herein, refers to a chemical compound that accelerates a chemical reaction without itself being affected. "Catalyst" may be used interchangeably with terms such as "pre-catalyst", "catalyst system", or "catalytic system". "Catalyst", as used herein, includes catalytic intermediates or species formed in situ.

"Group 5 metal" as used herein, refers to the d-electron comprising transition metals listed in the periodic table of the elements as group 5, including transition metals vanadium (V), niobium (Nb), tantalum (Ta), and dubnium (Db).

"Hydroaminoalkylation", as used herein, refers to a reaction between a secondary amine containing moiety and an olefin. A catalyst may often be used to promote such a reaction.

"Secondary amine", as used herein, refers to an amine in which the amino group is directly bonded to two C-atoms of any hybridization. The two C-atoms in α-position to the N-atom may be $sp^3$ hybridized.

"Olefin" or "alkene", as used herein, refers to an unsaturated hydrocarbon containing one or more pairs of C-atoms linked by a double bond.

"TOF", as used herein, refers to "turnover frequency".

Throughout this specification, unless the context requires otherwise, the words "comprise", "comprising" and the like, are to be construed in an inclusive sense as opposed to an exclusive sense, that is to say, in the sense of "including, but not limited to".

This disclosure relates to the discovery that rapid C—H alkylation of unprotected secondary arylamines with unactivated alkenes can be achieved with metal complex catalysts comprising a combination of a tantalum (Ta) organometallic reagent (e.g. $Ta(CH_2SiMe_3)_3Cl_2$) and a ureate N,O chelating-ligand salt.

Materials and Methods

The procedures described herein are given for the purposes of example and illustration only and should not be considered to limit the spirit or scope of the invention.

1. Materials

All reactions were performed under a $N_2$ atmosphere using Schlenk or glovebox techniques, unless otherwise stated. $TaCl_5$ (Strem), $Ta(NMe_2)_5$ (Strem), and (chloromethyl)trimethylsilane (Sigma) were used as received. $NaN(SiMe_3)_2$ (Sigma) was recrystallized from a hot toluene solution before use. All amines and alkenes were commercially available, dried over $CaH_2$ and distilled and degassed prior to use in catalytic experiments. $[Ta(NMe_2)_3Cl_2]_2$, $TaMe_3Cl_2$, $Ta(CH_2CMe_3)_3Cl_2$, and $Ta(CH_2SiMe_3)_3Cl_2$, were synthesized according to literature protocols (*Chem. Int. Ed.* 48, 4892-4894; *Synthesis* 46, 2884-2896; *Chem. Res* 48: 2576-2586; *Inorg. Chem.* 20: 1859-1866; *J. Am. Chem. Soc.* 100: 2389-2399; *Dalton Trans.* 40, 7777-7782). All glassware was dried in a 180° C. oven overnight before use. Toluene, hexanes and $Et_2O$ were dried over an activated alumina column and stored over activated molecular sieves (4 Å). $d_6$-Benzene and $d_8$-toluene were dried over sodium/ketyl and distilled prior to use. Experiments conducted on NMR tube scale were performed in J. Young NMR tubes (8"×5 mm) sealed with screw-type Teflon caps.

2. Instrumentation $^1H$ and $^{13}C$ NMR spectra were recorded on Bruker 300 MHz, or 400 MHz, Avance spectrometers at ambient temperature. Chemical shifts (δ) are given relative to the corresponding residual protio solvent and are reported in parts per million (ppm). Coupling constants J are given in Hertz (Hz). The following abbreviations are used to indicate signal multiplicity: s=singlet, d=doublet, t=triplet, q=quartet, m=multiplet, and br=broad. Assignment of the signals was carried out using 1D ($^1H$, $^{13}C\{^1H\}$) and 2D (COSY, HSQC and HMBC) NMR experiments.

3. Synthesis 3.1 Proligands

Figure 42:
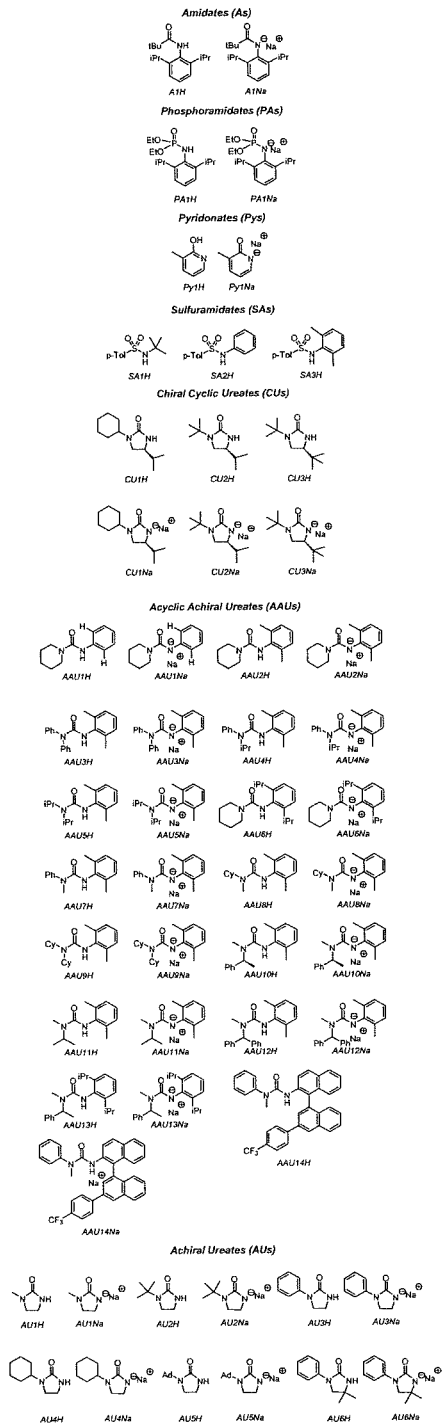
FIG. 42 is a legend of all ligands prepared and investigated in the study disclosed herein.

The synthesis of proligands is generally discussed below, with reference to particular exemplified proligands. FIG. 42 summarizes the proligands synthesized and disclosed herein.

General Procedure for the Synthesis of Urea Proligands:

Urea proligands were prepared following a modified literature procedure[3] in which the aniline (1 equiv) was dissolved in DCM and the solution was cooled to 0° C. Triphosgene (0.35 equiv) was added in one portion. The solution was stirred for five minutes after which N,N-diisopropylethylamine (2 equiv) was added and the cold bath removed. The solution was stirred for 1 hour and then piperidine (1 equiv) and a second portion of N,N-diisopropylethylamine (1 equiv) were added. The solution was stirred for an additional hour, and then diluted with 1M HCl. The organic phase was washed three times with 1M HCl dried over $MgSO_4$, filtered, and concentrated by rotary evaporation.

Synthesis of
3-(2,6-dimethylphenyl)-1,1-diphenylurea

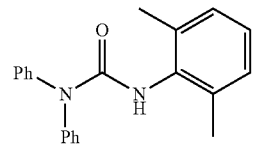 [SMILES: Cc1cccc(C)c1NC(=O)N(c1ccccc1)c1ccccc1]

Prepared following the general procedure outlined above. Recrystallization provided the desired compound as a white solid (1.2 g, Unoptimized Synthesis): $^1H$ NMR (CDCl$_3$, 300 MHz, 298 K): δ 7.42-7.38 (overlapping m, 8H, o-C$_6$H$_5$ and m-C$_6$H$_5$), 7.29-7.18 (m, 2H, p-C$_6$H$_5$), 7.05 (s, 3H, 2,6-Me$_2$C$_6$H$_3$), 5.79 (NH), 2.27 (s, 6H, CH$_3$) ppm. $^{13}C$ NMR (CDCl$_3$, 75 MHz, 298 K): δ 153.94 (C=O), 142.72 (i-C$_6$H$_5$), 135.68 (o-C$_6$H$_3$), 134.56 (i-C$_6$H$_3$), 129.53 (m-C$_6$H$_5$), 128.12 (m-C$_6$H$_3$), 127.28 (o-C$_6$H$_5$), 126.85 (p-C$_6$H$_5$), 126.40 (p-C$_6$H$_3$), 18.62 (CH$_3$) ppm.

Figure 2:
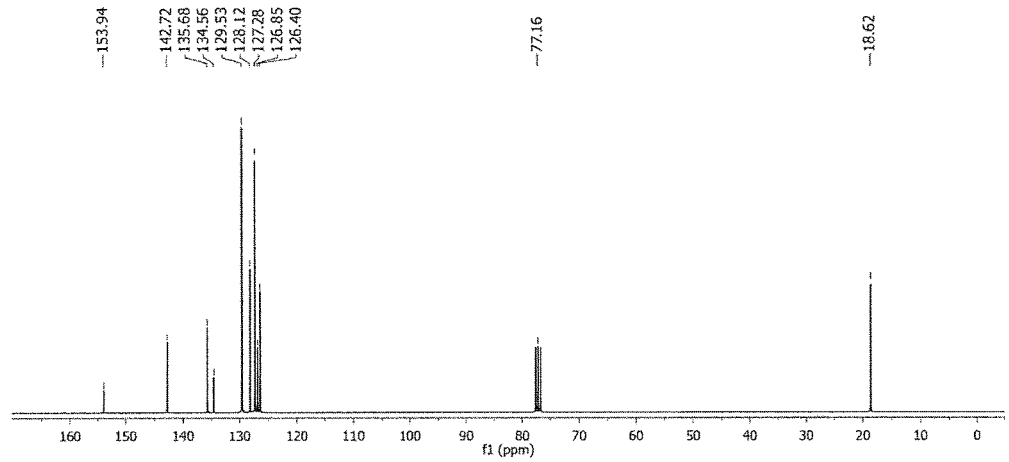
FIG. 2 is a ¹³C NMR spectrum (75 MHz, CDCl₃, 298 K) of 3-(2,6-dimethylphenyl)-1,1-diphenylurea.

A $^1H$ NMR spectrum (300 MHz, CDCl$_3$, 298 K) of 3-(2,6-dimethylphenyl)-1,1-diphenylurea is shown in FIG. 1. A $^{13}C$ NMR spectrum (75 MHz, CDCl$_3$, 298 K) of 3-(2,6-dimethylphenyl)-1,1-diphenylurea is shown in FIG. 2.

Synthesis of 3-(2,6-dimethylphenyl)-1-isopropyl-1-phenylurea

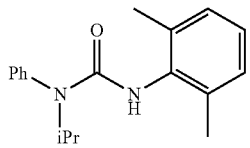 [SMILES: Cc1cccc(C)c1NC(=O)N(c1ccccc1)C(C)C]

Prepared following the general procedure outlined above. Recrystallization provided the desired compound as a white solid (1.1 g, Unoptimized Synthesis): $^1$H NMR (CDCl$_3$, 400 MHz, 298 K): δ 7.61-7.28 (overlapping m, 5H, o,m,p-C$_6$H$_5$), 6.99 (s, 3H, C$_6$H$_3$), 5.24 (NH), 4.96 (hept, $^3J_{H-H}$=6.5 Hz, 1H, CH(CH$_3$)$_2$), 2.19 (s, 6H, 2,6-(CH$_3$)$_2$C$_6$H$_3$), 1.14 (d, $^3J_{H-H}$=6.2 Hz, 6H, CH(CH$_3$)$_2$) ppm. $^{13}$C NMR (CDCl$_3$, 101 MHz, 298 K): 154.62 (C=O), 138.17 (i-C$_6$H$_5$), 135.71 (o-C$_6$H$_3$), 135.18 (i-C$_6$H$_3$), 131.21 (m-C$_6$H$_3$), 129.83 (o-C$_6$H$_5$), 128.66 (p-C$_6$H$_5$), 127.94 (m-C$_6$H$_3$), 126.38 (p-C$_6$H$_3$), 46.58 (CH(CH$_3$)$_2$), 21.65 (CH(CH$_3$)$_3$), 18.47 (2,6-(CH$_3$)$_2$C$_6$H$_3$) ppm.

Figure 3:
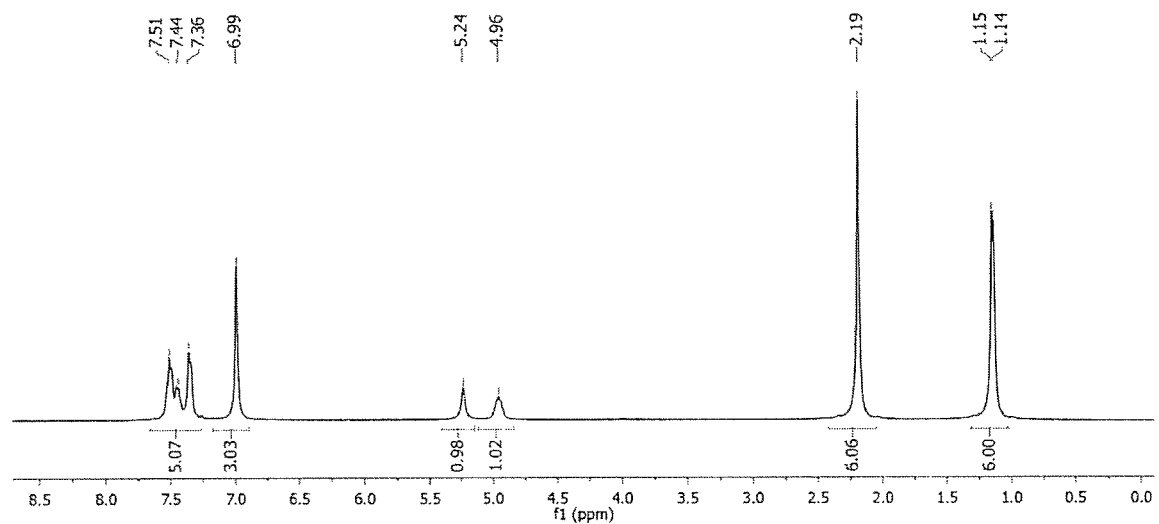
FIG. 3 is a ¹H NMR spectrum (300 MHz, CDCl₃, 298 K) of 3-(2,6-dimethylphenyl)-1-isopropyl-1-phenylurea.
Figure 4:
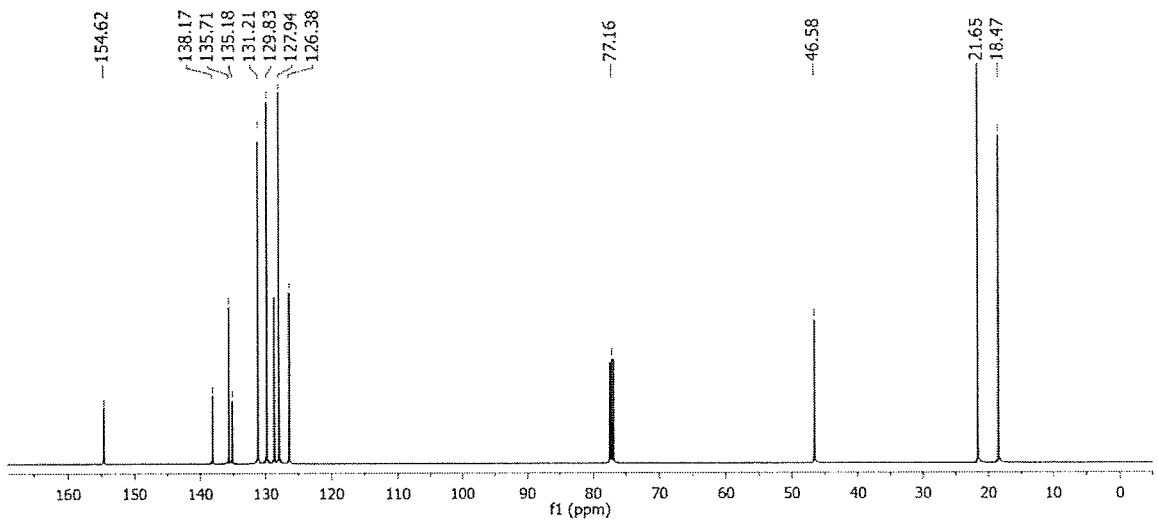
FIG. 4 is a ¹³C NMR spectrum (75 MHz, CDCl₃, 298 K) of 3-(2,6-dimethylphenyl)-1-isopropyl-1-phenylurea.

A $^1$H NMR spectrum (300 MHz, CDCl$_3$, 298 K) of 3-(2,6-dimethylphenyl)-1-isopropyl-1-phenylurea is shown in FIG. 3. A $^{13}$C NMR spectrum (75 MHz, CDCl$_3$, 298 K) of 3-(2,6-dimethylphenyl)-1-isopropyl-1-phenylurea.

Cyclic Ureate Ligands

Synthesis and Characterization of Cyclic Ureate Proligands

Scheme 1. General synthesis of cyclic ureate proligands

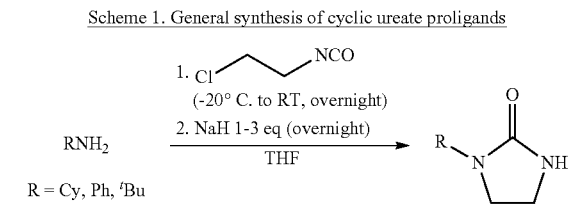

Synthesis of 1-cyclohexylimidazolidin-2-one ($^{Cy}$LH)

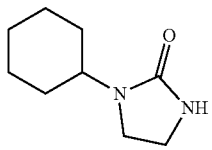 [SMILES: O=C1NCCN1C1CCCCC1]

A solution 2-chloroethyl isocyanate (1.11 g, 10.5 mmol) in THF (50 mL) was added dropwise to a stirring solution of cyclohexylamine (0.99 g, 10 mmol) in THF (20 mL) at room temperature. The resulting reaction mixture was treated with NaH (0.24 g, 10 mmol) under an inert atmosphere and stirred at room temperature overnight under an inert atmosphere. The mixture was treated with saturated NH$_4$Cl (100 mL) and EtOAc (200 mL). The organic layer was separated and the aqueous layer was extracted with EtOAc (3×50 mL). The combined organic fractions were dried over Na$_2$SO$_4$ and concentrated under vacuum to form a colorless suspension in EtOAc. The reaction mixture was filtered and the resulting solid was dried to form the desired product. Yield (0.44 g, 27%). $^1$H NMR (CDCl$_3$, 300 MHz, 298 K): δ 5.41 (br s, 1H, NH), 3.77-3.58 (m, 1H, NCH), 3.43 (s, 4H, CH$_2$CH$_2$NH), 1.92-1.52 (m, 11H, HNCH$_2$) ppm. $^{13}$C NMR (CDCl$_3$, 75 MHz, 298 K): δ 162.52 (C=O), 40.71 ($^{tBu}$NCH$_2$), 51.15 (CH), 38.76 (HNCH$_2$), 30.39 ($^{Cy}$CH$_2$), 25.64 ($^{Cy}$CH$_2$) ppm. HRMS (ESI): m/z calcd for C$_9$H$_{16}$N$_2$ONa [M+Na$^+$]: 191.1160. Found: 191.1159.

Figure 22:
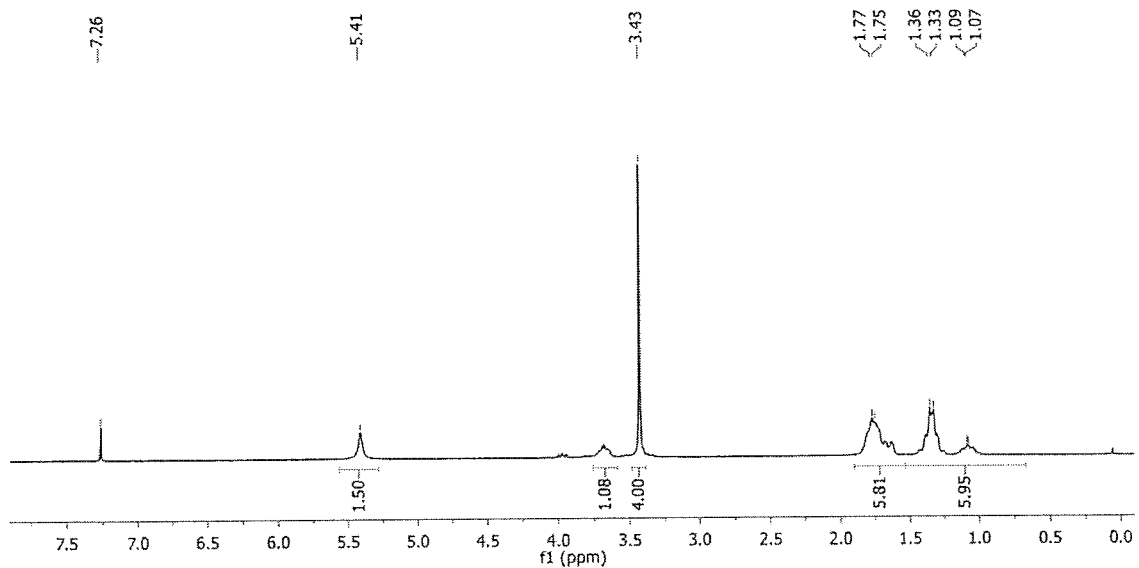
FIG. 22 is a ¹H NMR spectrum (300 MHz, CDCl₃, 298 K) of 1-cyclohexylimidazolidin-2-one ($^{Cy}$LH).
Figure 23:
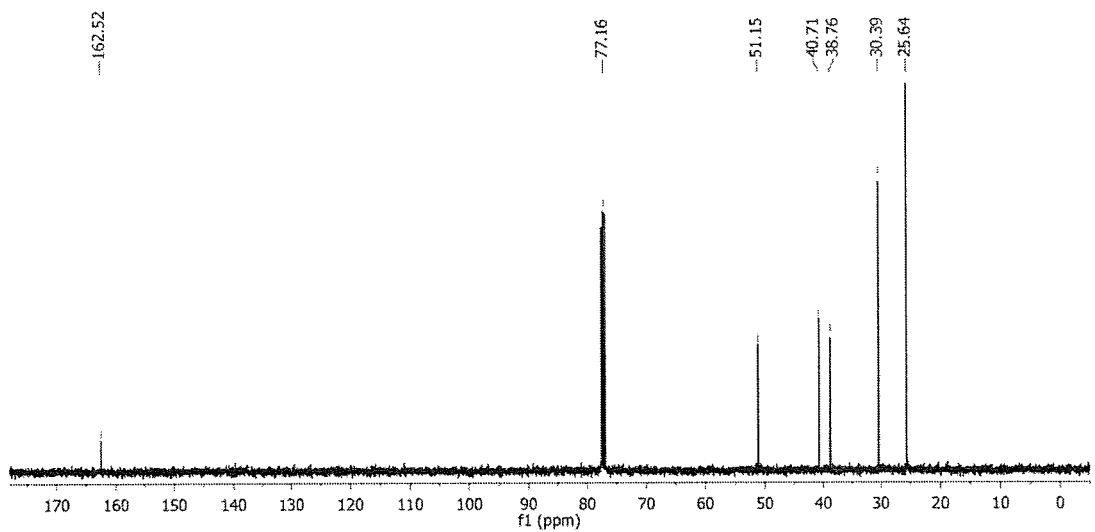
FIG. 23 is a ¹³C NMR spectrum (100 MHz, CDCl₃, 298 K) of 1-cyclohexylimidazolidin-2-one ($^{Cy}$LH).

FIG. 22 is a $^1$H NMR spectrum (300 MHz, CDCl$_3$, 298 K) of 1-cyclohexylimidazolidin-2-one ($^{Cy}$LH). FIG. 23 is a $^{13}$C NMR spectrum (100 MHz, CDCl$_3$, 298 K) of 1-cyclohexylimidazolidin-2-one ($^{Cy}$LH).

Synthesis of 1-phenylimidazolidin-2-one ($^{Ph}$LH)

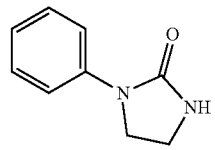 [SMILES: O=C1NCCN1c1ccccc1]

A solution 2-chloroethyl isocyanate (1.05 g, 10 mmol) in THF (50 mL) was added dropwise to a stirring solution of phenylamine (0.93 g, 10 mmol) in THF (20 mL) at −20° C. The solution was brought to room temperature overnight. The resulting reaction mixture was treated with NaH (0.24 g, 10 mmol) under an inert atmosphere and stirred at room temperature overnight. The mixture was treated with saturated NH$_4$Cl (100 mL) and EtOAc (200 mL). The organic layer was separated and the aqueous layer was extracted with EtOAc (3×50 mL). The combined organic fractions were dried over Na$_2$SO$_4$ and concentrated under vacuum to form a colorless suspension in EtOAc. The reaction mixture was filtered and the resulting solid was dried to form the desired product. Yield (0.42 g, 26%). $^1$H NMR (CDCl$_3$, 300 MHz, 298 K): δ 7.58 (d, 2H, J$_{H-H}$=8.2 Hz, m-C$_6$H$_5$), 7.38-7.29 (m, 2H, o-C$_6$H$_5$), 7.05 (t, 2H, J$_{H-H}$=7.2 Hz, p-C$_6$H$_5$), 4.00-3.84 (m, 2H, $^{Ph}$NCH$_2$), 3.65-3.48 (m, 2H, HNCH$_2$) ppm. $^{13}$C NMR (CDCl$_3$, 75 MHz, 298 K): δ 160.27 (C=O), 140.18 (C$_6$H$_5$), 128.92 (C$_6$H$_5$), 122.83 (C$_6$H$_5$), 118.09 (C$_6$H$_5$), 45.49 ($^{Ph}$NCH$_2$), 37.70 (HNCH$_2$) ppm. HRMS (ESI): m/z calcd for C$_9$H$_{10}$N$_2$ONa [M+Na$^+$]: 185.0691. Found: 185.0691.

Figure 24:
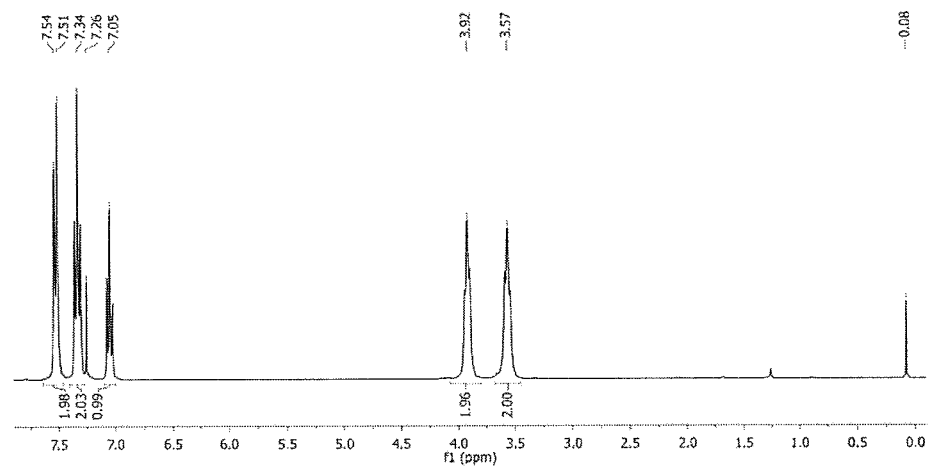
FIG. 24 is a ¹H NMR spectrum (300 MHz, CDCl₃, 298 K) of 1-phenylimidazolidin-2-one ($^{Ph}$LH).
Figure 25:
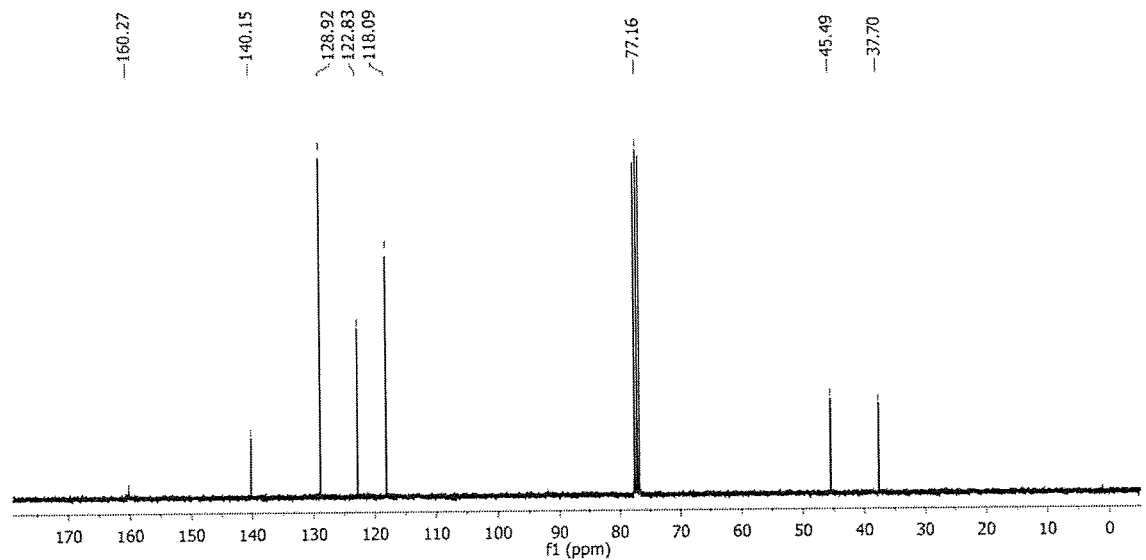
FIG. 25 is a ¹H NMR spectrum (75 MHz, CDCl₃, 298 K) of 1-phenylimidazolidin-2-one ($^{Ph}$LH).

FIG. 24 is a $^1$H NMR spectrum (300 MHz, CDCl$_3$, 298 K) of 1-phenylimidazolidin-2-one ($^{Ph}$LH). FIG. 25 is a $^1$H NMR spectrum (75 MHz, CDCl$_3$, 298 K) of 1-phenylimidazolidin-2-one ($^{Ph}$LH).

Synthesis of 1-(tert-butyl)imidazolidin-2-one ($^{tBu}$LH)

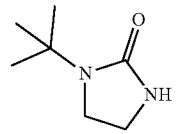

A solution 2-chloroethyl isocyanate (6.80 g, 64 mmol) in THF (50 mL) was added dropwise to a stirring solution of tertbutylamine (4.28 g, 58.5 mmol) in THF (20 mL) at −20° C. The solution was brought to room temperature overnight. The resulting reaction mixture was treated with NaH (6.8 g, 283 mmol) under an inert atmosphere and heated at 65° C. overnight under an inert atmosphere. The mixture was brought to dryness and treated with saturated NH$_4$Cl (100 mL) and EtOAc (200 mL). The organic layer was separated and the aqueous layer was extracted with EtOAc (3×50 mL). The combined organic fractions were dried over Na$_2$SO$_4$ and brought to dryness under vacuum forming a yellow oil. Hexanes (5 mL) were then added resulting with the formation of a solid at the bottom of the round bottom flask. The mother liquor was removed by filtration. This process was repeated 3 more times and the combined hexane solutions (fraction 1) were stored at −30° C. overnight, while the solid (fraction 2) was also kept. Storing the combined hexane solutions (fraction 1) at low temperatures resulted in the formation of colorless crystals that were later filtered and dried in vacuo to afford 350 mg of pure product. The solid from fraction 2 was sublimed at 100° C. under vacuum to afford a waxy solid on the cold finger. The resulting waxy solid was washed with hexanes (2×4 mL) to afford 770 mg of pure product. Total yield: 1.12 g (13%). $^1$H NMR (CDCl$_3$, 300 MHz, 298 K): δ 4.37 (br s, 1H, NH), 3.49-3.40 (m, 2H, $^{tBu}$NCH$_2$), 3.33-3.23 (m, 2H, HNCH$_2$), 1.36 (s, 9H, C(CH$_3$)$_3$) ppm. $^{13}$C NMR (CDCl$_3$, 75 MHz, 298 K): δ 163.15 (C=O), 52.96 (C(CH$_3$)$_3$), 43.73 ($^{TbU}$NCH$_2$), 38.13 (HNCH$_2$), 27.67 (C(CH$_3$)$_3$) ppm. HRMS (ESI): m/z calcd for C$_7$H$_{14}$N$_2$O [M+Na$^+$]: 165.10039. Found: 165.1001. Anal. Calcd. for C$_7$H$_{14}$N$_2$O: C, 59.12; H, 9.92; N, 19.70; Found: C, 59.12; H, 10.29; N, 19.71.

Figure 26:
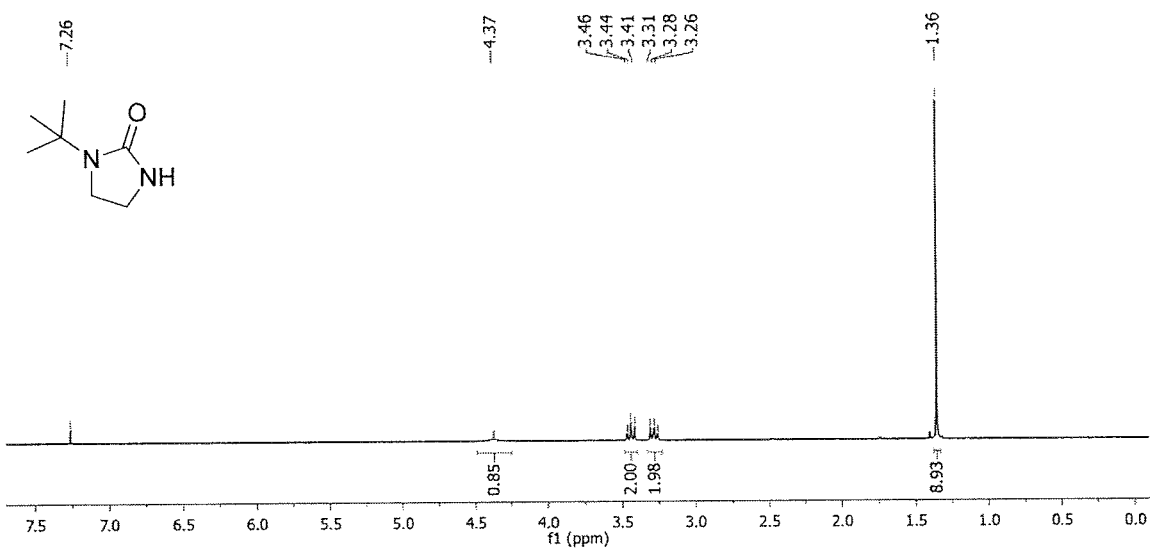
FIG. 26 is a ¹H NMR spectrum (300 MHz, CDCl₃, 298 K) of 1-(tert-butyl)imidazolidin-2-one ($^{tBu}$LH).
Figure 27:
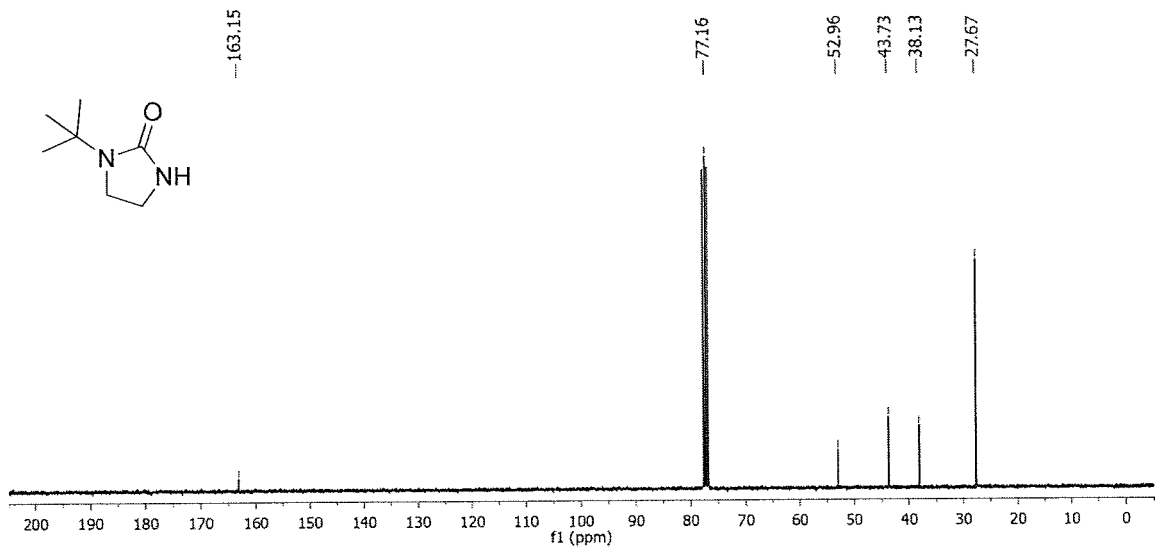
FIG. 27 is a ¹³C NMR spectrum (75 MHz, CDCl₃, 298 K) of 1-(tert-butyl)imidazolidin-2-one ($^{tBu}$LH).

FIG. 26 is a $^1$H NMR spectrum (300 MHz, CDCl$_3$, 298 K) of 1-(tert-butyl)imidazolidin-2-one ($^{tBu}$LH). FIG. 27 is a $^{13}$C NMR spectrum (75 MHz, CDCl$_3$, 298 K) of 1-(tert-butyl)imidazolidin-2-one ($^{tBu}$LH).

Synthesis of Cyclic Ureate Ligand Salts

General Procedure for the Synthesis of Ligand Salts $^x$LH (X=Me,Cy, pH, $^t$Bu):

NaN(SiMe$_3$)$_2$ (1 equiv.) and the corresponding proteoligand (1 equiv.) were mixed in toluene (~5 mL) and stirred overnight at room temperature. The volatiles were then removed at low pressure and the resulting solid was thoroughly stripped with hexanes (3×5 mL) and dried to give the sodium salt in moderate to quantitative yields as a colorless powder. The resulting ligand salts were used directly without further purification via storage in a glove box. Except in the case of $^{Dipp}$LH, NMR characterization was precluded due to poor solubility in common NMR solvents (e.g. d$_6$-benzene or d$_8$-toluene).

Synthesis of sodium 3-methyl-2-oxoimidazolidin-1-ide ($^{Me}$L$^-$Na$^+$)

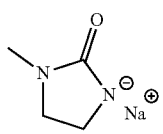

Prepared following the general procedure outlined above: $^{Me}$LH (197 mg, 1.97 mmol) and NaN(SiMe$_3$)$_2$ (361 mg, 1.97 mmol). Yield (163 mg, 68%).

Synthesis of sodium 3-cyclohexyl-2-oxoimidazolidin-1-ide ($^{Cy}$L$^-$Na$^+$)

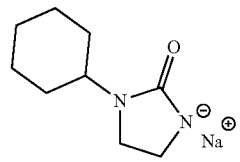 [SMILES: O=C1[N-]CCN1C1CCCCC1 ; [Na+]]

Prepared following the general procedure outlined above: $^{Cy}$LH (100 mg, 0.59 mmol) and NaN(SiMe$_3$)$_2$ (109 mg, 0.59 mmol). Yield (107 mg, 95%).

Synthesis of sodium 2-oxo-3-phenylimidazolidin-1-ide ($^{Ph}$L$^-$Na+)

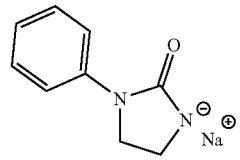 [SMILES: O=C1[N-]CCN1c1ccccc1 ; [Na+]]

Prepared following the general procedure outlined above: $^{Ph}$LH (150 mg, 0.93 mmol) and NaN(SiMe$_3$)$_2$ (170 mg, 0.93 mmol). Yield (140 mg, 82%).

Synthesis of sodium 3-(tert-butyl)-2-oxoimidazolidin-1-ide ($^{tBu}$L$^-$Na$^+$)

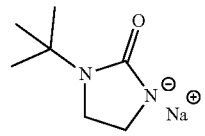

Prepared following the general procedure outlined above: $^{tBu}$L$^-$Na$^+$ (230 mg, 1.62 mmol) and NaN(SiMe$_3$)$_2$ (297 g, 1.62 mmol). Yield (265 mg, 99%).

Acyclic Ureate Ligands

Synthesis and Characterization of Proteoligands

General procedure for the synthesis of urea based proteoligands: Prepared following a modified literature procedure in which a chosen primary amine (1 equiv.) was dissolved in dichloromethane and the solution was cooled to 0° C. Triphosgene (0.35 equiv.) was added in portions as a solid. The solution was stirred for five minutes after which N,N-diisopropylethylamine DIPEA (3 equiv.) was added and the cold bath removed. The solution was stirred for 1 hour and then the appropriate amine (1 equiv.) and a second portion of DIPEA (1 equiv.) was added. The solution was stirred for an additional hour, and then diluted with 3M HCl. The organic phase was washed three times with 1M HCl dried over MgSO$_4$, filtered, and concentrated by rotary evaporation to give the crude product.

Synthesis of 3-(2,6-dimethylphenyl)-1-methyl-1-(1-phenylethyl)urea

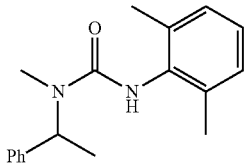 [SMILES: Cc1cccc(C)c1NC(=O)N(C)C(C)c1ccccc1]

Prepared following the general procedure outlined above: 2,6-dimethylaniline (2.25 g, 18.5 mmol), triphosgene (1.81 g, 6.10 mmol), DIPEA (7.2 g, 55.5 mmol), N-methyl-1-phenylethan-1-amine (2.5 g, 18.5 mmol). Recrystallization from a concentrated ethyl acetate solution provided the desired compound as a white solid (3.48 g, 66.9%): $^1$H NMR (CDCl$_3$, 300 MHz, 298 K): δ 7.41-7.26 (overlapping m, 5H, o-C$_6$H$_5$ m-C$_6$H$_5$, and p-C$_6$H$_5$), 7.04 (s, 3H, m-C$_6$H$_5$, and p-C$_6$H$_5$), 5.86 (br s, 1H, NH), 5.64-5.57 (q, 1H, CHCH$_3$), 2.79 (s, 3H, CH$_3$), 2.19 (s, 6H, 2,6-(CH$_3$)$_2$C$_6$H$_3$) ppm. $^{13}$C NMR (CDCl$_3$, 75 MHz, 298 K): δ 156.31 (C=O), 141.79, 135.58, 135.33, 128.64, 128.07, 127.28, 126.88, 126.34, 52.80, 29.53, 18.43, 17.02 ppm. HRMS (ESI): m/z calcd for C$_{18}$H$_{23}$N$_2$O [M+H$^+$]: 283.1810. Found: 283.1809.

Figure 33:
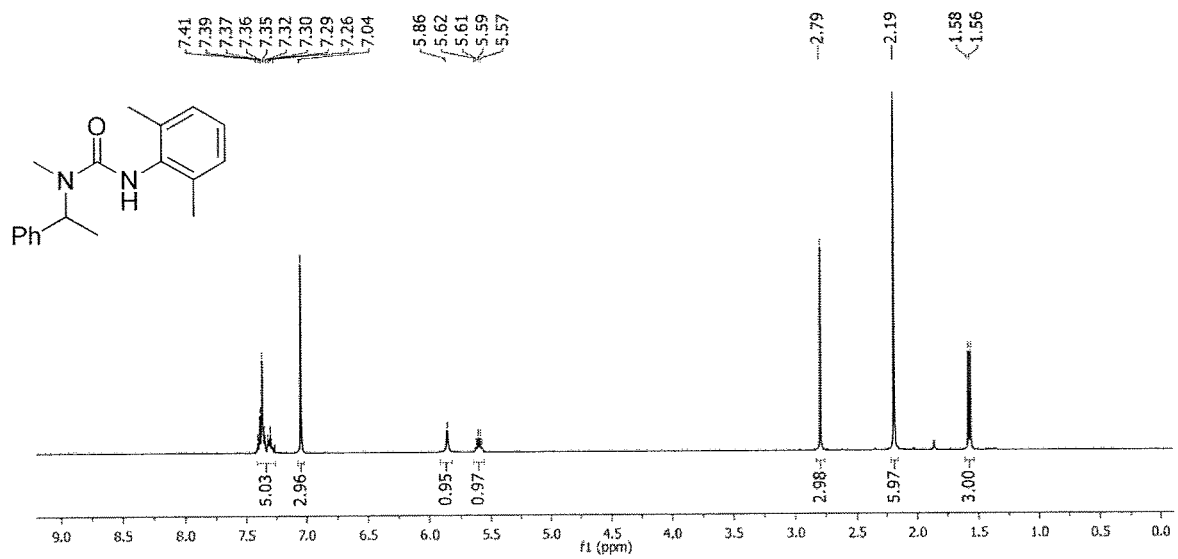
FIG. 33 is a ¹H NMR spectrum (400 MHz, CDCl₃, 298 K) of 3-(2,6-dimethylphenyl)-1-methyl-1-(1-phenylethyl)urea.
Figure 34:
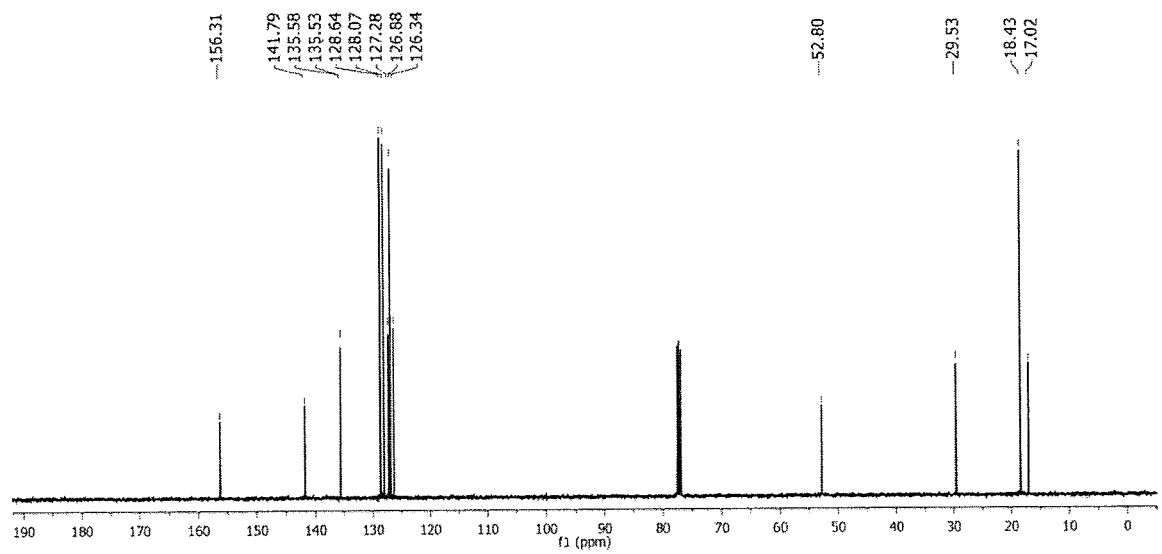
FIG. 34 is a ¹³C NMR spectrum (100 MHz, benzene-d₆, 298 K) of 3-(2,6-dimethylphenyl)-1-methyl-1-(1-phenylethyl)urea.

FIG. 33 is a $^1$H NMR spectrum (400 MHz, CDCl$_3$, 298 K) of 3-(2,6-dimethylphenyl)-1-methyl-1-(1-phenylethyl)urea. FIG. 34 is a $^{13}$C NMR spectrum (100 MHz, benzene-d$_6$, 298 K) of 3-(2,6-dimethylphenyl)-1-methyl-1-(1-phenylethyl)urea.

Synthesis of 3-(2,6-dimethylphenyl)-1-isopropyl-1-phenylurea

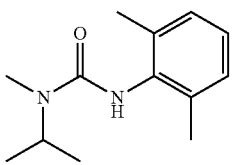 [SMILES: Cc1cccc(C)c1NC(=O)N(C)C(C)C]

Prepared following the general procedure outlined above: 2,6-dimethylaniline (1.5 g, 20.5 mmol), triphosgene (2.02 g, 7.41 mmol), DIPEA (7.95 g, 61.5 mmol), N-isopropylaniline (2.5 g, 20.5 mmol). Recrystallization from a concentrated ethyl acetate solution provided the desired compound as a white solid (3.20 g, 65%): $^1$H NMR (CDCl$_3$, 400 MHz, 298 K): δ 7.05 (s, 3H, o,m,p-C$_6$H$_5$), 5.69 (br s, 1H, NH), 4.56-4.49 (m, 1H, CH(CH$_3$)$_2$), 2.86 (s, 3H, CH$_3$), 2.24 (s, 6H, 2,6-(CH$_3$)$_2$C$_6$H$_3$), 1.17 (d, $J_{H-H}$=1.7 Hz, 6H, CH(CH$_3$)$_2$) ppm. $^{13}$C NMR (CDCl$_3$, 101 MHz, 298 K): δ 156.00 (C=O), 135.70, 135.57, 128.20, 126.40, 45.89, 27.45, 20.21, 18.56 ppm. HRMS (ESI): m/z calcd for C$_{13}$H$_{21}$N$_2$O [M+H$^+$]: 221.1654. Found: 221.1656.

Figure 35:
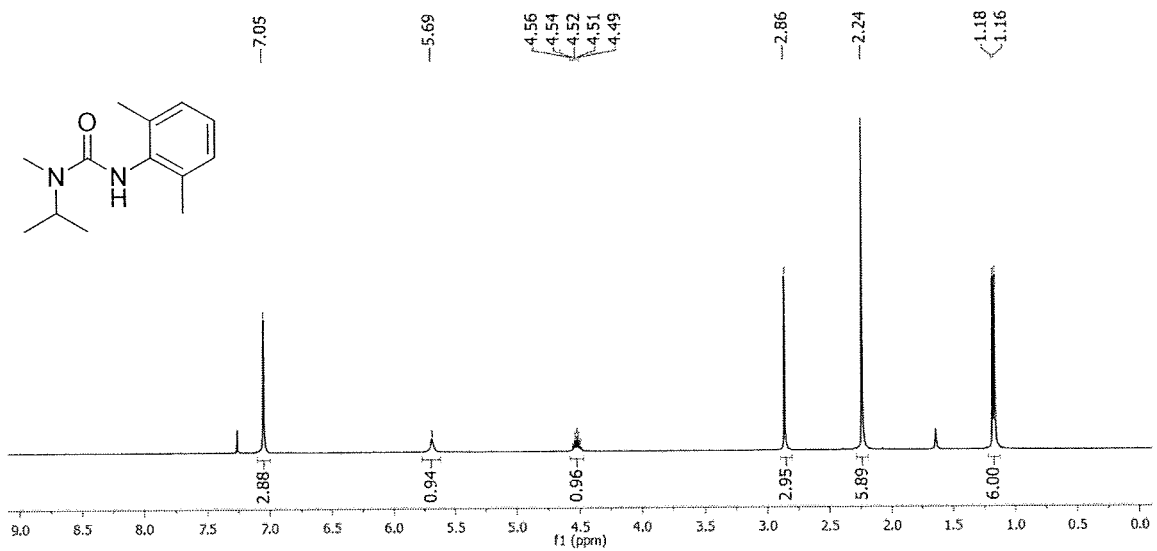
FIG. 35 is a ¹H NMR spectrum (400 MHz, CDCl₃, 298 K) of 3-(2,6-dimethylphenyl)-1-isopropyl-1-phenylurea.
Figure 36:
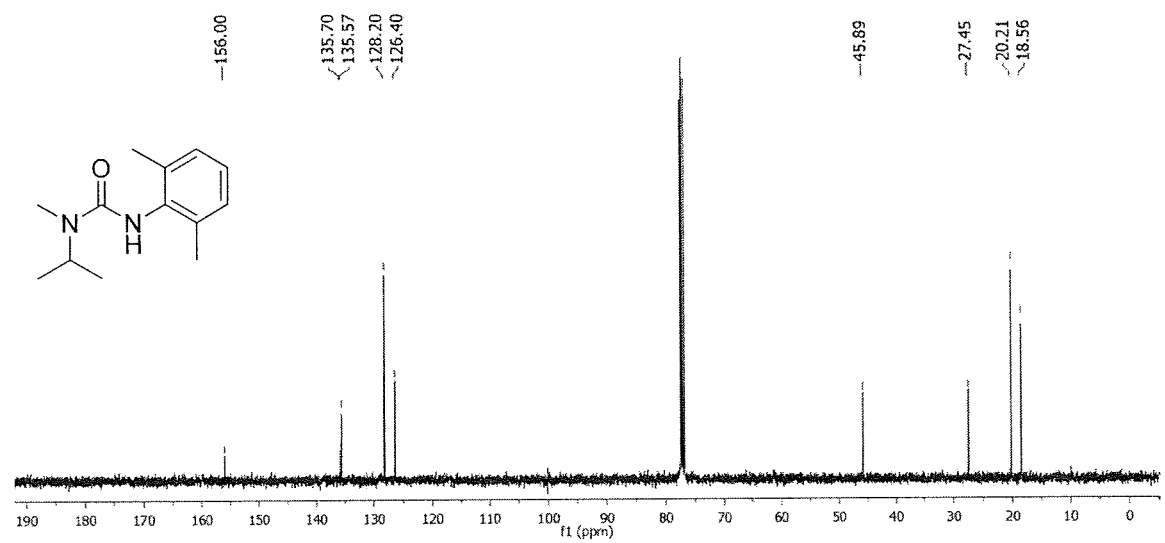
FIG. 36 is a ¹³C NMR spectrum (100 MHz, benzene-d₆, 298 K) of 3-(2,6-dimethylphenyl)-1-isopropyl-1-phenylurea.

FIG. 35 is a $^1$H NMR spectrum (400 MHz, CDCl$_3$, 298 K) of 3-(2,6-dimethylphenyl)-1-isopropyl-1-phenylurea. FIG. 36 is a $^{13}$C NMR spectrum (100 MHz, benzene-d$_6$, 298 K) of 3-(2,6-dimethylphenyl)-1-isopropyl-1-phenylurea.

Synthesis of 1-benzhydryl-3-(2,6-dimethylphenyl)-1-methylurea

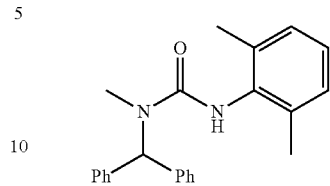

Prepared following the general procedure outlined above: 2,6-dimethylaniline (307 mg, 2.53 mmol), triphosgene (250.2 mg, 0.843 mmol), DIPEA (981 mg, 7.59 mmol), N-methyl-1,1-diphenylmethanamine (500 mg, 2.53 mmol). Recrystallization from a concentrated ethyl acetate solution provided the desired compound as a white solid (750 mg, 86%): $^1$H NMR (CDCl$_3$, 400 MHz, 298 K): δ 7.41-7.27 (overlapping m, 10H, o,m,p-C$_6$H$_5$), 7.04 (s, 3H, m,p-C$_6$H$_5$), 6.70 (s, 1H, NHCH), 5.78 (br s, 1H, NH), 2.88 (s, 3H, CH$_3$), 2.16 (s, 6H, 2,6-(CH$_3$)$_2$C$_6$H$_3$) ppm. $^{13}$C NMR (CDCl$_3$, 101 MHz, 298 K): δ 156.57 (C=O), 139.66, 135.47, 135.30, 128.80, 128.77, 128.25, 127.80, 126.49, 63.30, 32.05, 28.48 ppm. HRMS (ESI): m/z calcd for C$_{23}$H$_{25}$N$_2$O [M+H$^+$]: 345.1967 Found: 345.1964.

Figure 37:
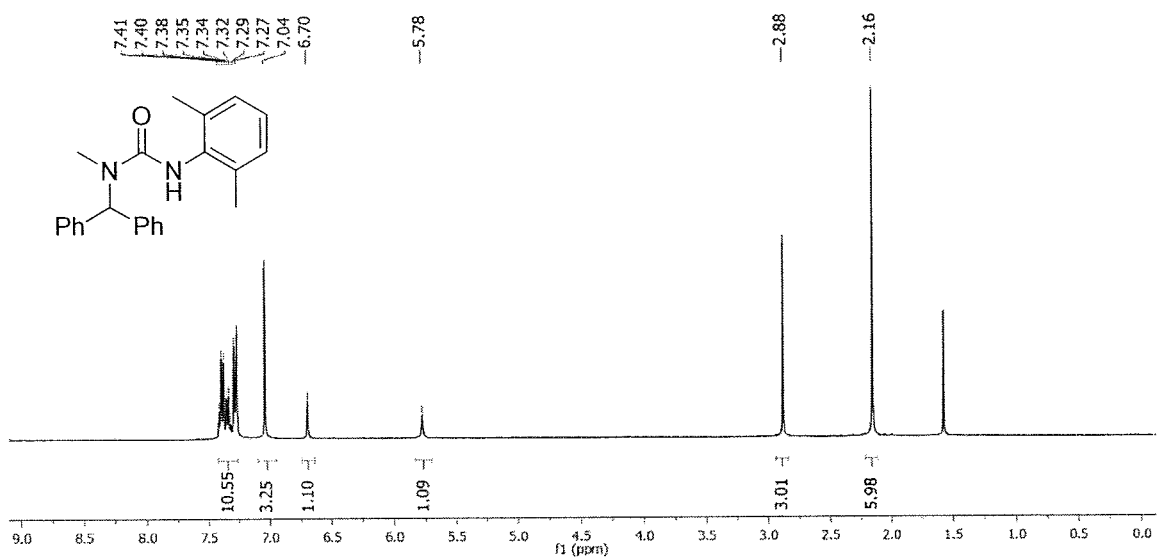
FIG. 37 is a ¹H NMR spectrum (400 MHz, CDCl₃, 298 K) of 1-benzhydryl-3-(2,6-dimethylphenyl)-1-methylurea.
Figure 38:
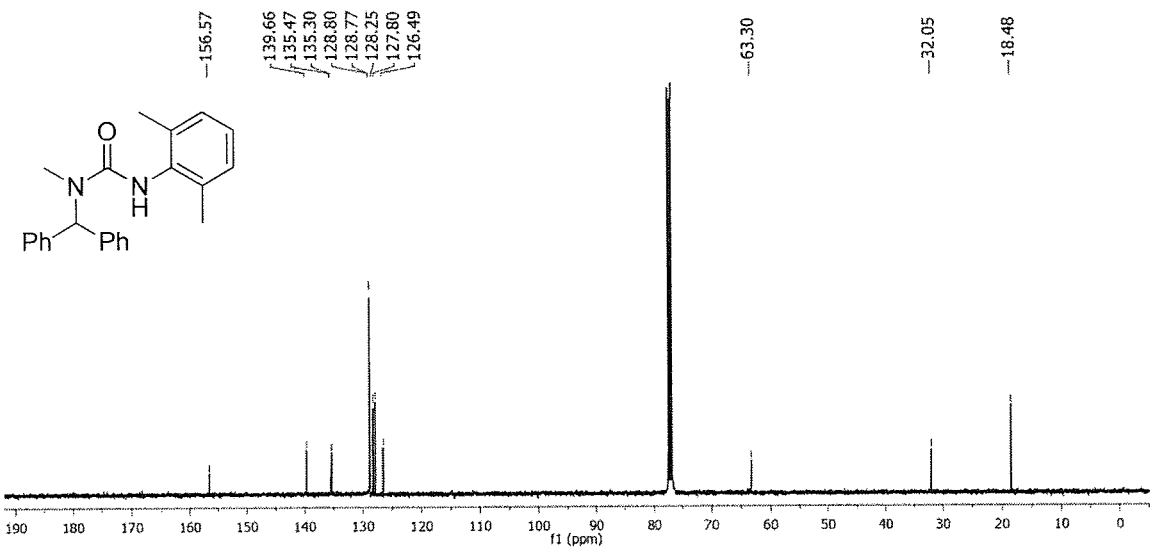
FIG. 38 is a ¹³C NMR spectrum (100 MHz, CDCl₃, 298 K) of 1-benzhydryl-3-(2,6-dimethylphenyl)-1-methylurea.

FIG. 37 is a $^1$H NMR spectrum (400 MHz, CDCl$_3$, 298 K) of 1-benzhydryl-3-(2,6-dimethylphenyl)-1-methylurea. FIG. 38 is a $^{13}$C NMR spectrum (100 MHz, CDCl$_3$, 298 K) of 1-benzhydryl-3-(2,6-dimethylphenyl)-1-methylurea.

Synthesis of 3-(2,6-diisopropylphenyl)-1-methyl-1-(1-phenylethyl)urea

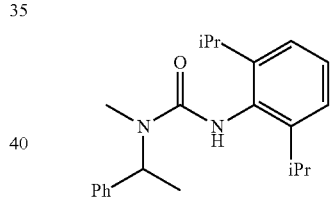

Prepared following the general procedure outlined above: 2,6-dimethylaniline (1.32 g, 7.40 mmol), triphosgene (724 mg, 2.44 mmol), DIPEA (2.87 g, 22.2 mmol), N-methyl-1,1-diphenylmethanamine (1.0 g, 7.40 mmol). Recrystallization from a concentrated ethyl acetate solution provided the desired compound as a white solid (1.81 g, 72.3%): $^1$H NMR (CDCl$_3$, 400 MHz, 298 K): δ 7.51-7.50 (overlapping m, 4H), 7.45-7.39 (overlapping m, 2H), 7.37-7.35 (m, 1H), 7.28 (m, 1H), 5.78-5.72 (overlapping m, 2H), 3.22-3.12 (m, 2H, CH(CH$_3$)$_2$), 3.00 (s, 3H, CH$_3$), 1.72 (s, 3H, CH$_3$), 1.31 (s, 12H, CH(CH$_3$)$_2$) ppm. $^{13}$C NMR (CDCl$_3$, 101 MHz, 298 K): δ 157.22 (C=O), 146.52, 142.12, 132.80, 128.73, 127.63, 127.41, 126.95, 123.36, 52.99, 29.82, 28.79, 23.81 ppm. HRMS (ESI): m/z calcd for C$_{22}$H$_{31}$N$_2$O [M+H$^+$]: 339.2437. Found: 339.2444.

Figure 39:
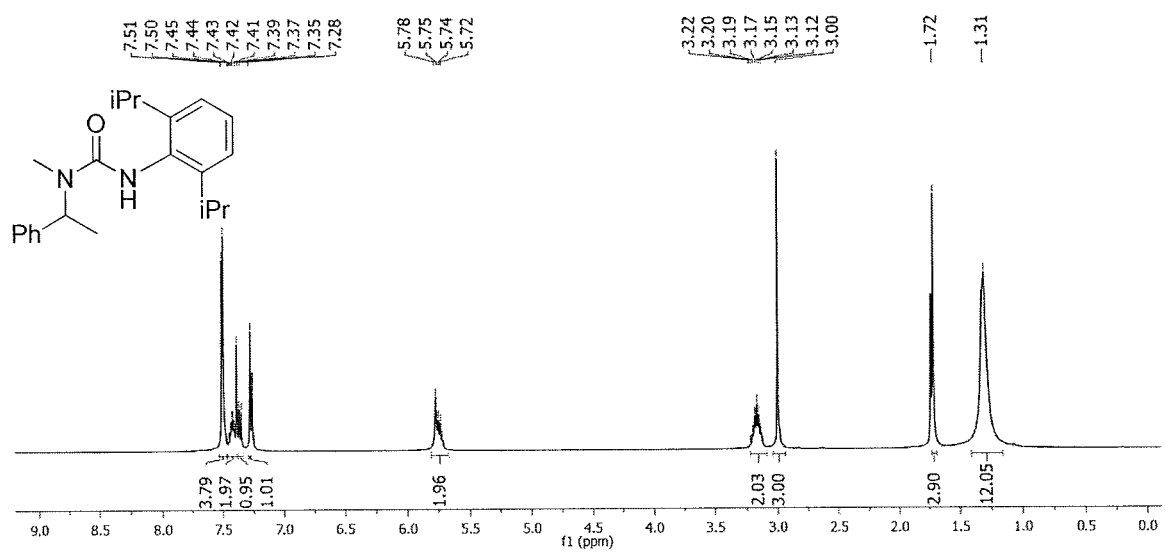
FIG. 39 is a ¹H NMR spectrum (400 MHz, CDCl₃, 298 K) of 3-(2,6-diisopropylphenyl)-1-methyl-1-(1-phenylethyl)urea.
Figure 40:
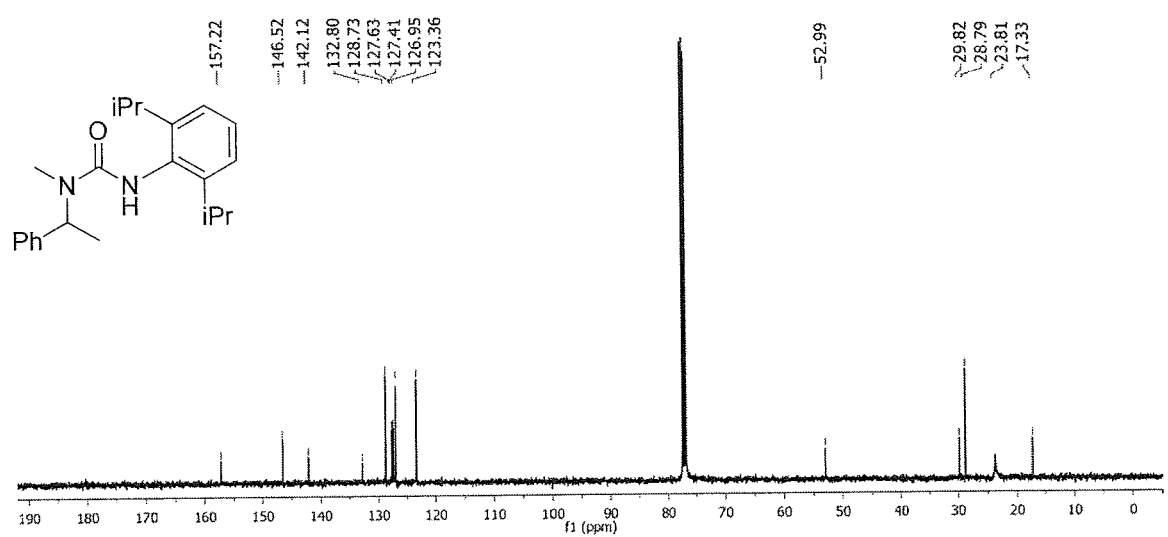
FIG. 40 is a ¹³C NMR spectrum (100 MHz, CDCl₃, 298 K) of 3-(2,6-diisopropylphenyl)-1-methyl-1-(1-phenylethyl)urea.

FIG. 39 is a $^1$H NMR spectrum (400 MHz, CDCl$_3$, 298 K) of 3-(2,6-diisopropylphenyl)-1-methyl-1-(1-phenylethyl)urea. FIG. 40 is a $^{13}$C NMR spectrum (100 MHz, CDCl$_3$, 298 K) of 3-(2,6-diisopropylphenyl)-1-methyl-1-(1-phenylethyl)urea.

Synthesis of Ta(CH$_2$SiMe$_3$)$_3$Br$_2$

A solution of Zn(CH$_2$SiMe$_3$)$_2$ (0.64 g, 2.67 mmol) in hexanes (20 mL) was added to a suspension of TaBr$_5$ (1.00 g, 1.72 mmol) in hexanes (10 mL). The reaction mixture was stirred at room temperature overnight forming a colorless precipitate. The following day, the solution was filtered and concentrated in vacuo to afford the formation of the title product as yellow powder. Yield (0.73 g, 71%). $^1$H NMR (toluene-d$_8$, 300 MHz, 298 K): δ 2.11 (s, 6H, CH$_2$), 0.29 (s, 27H, SiCH$_3$) ppm.

3.3 Ligand Salts

General procedure for the synthesis of ligand salts NaN(SiMe$_3$)$_2$ (1 equiv.) was added in portions to a suspension of the corresponding proteo-ligand (1 equiv.) in Et$_2$O (~10 mL) and stirred overnight at room temperature. The volatiles were then removed at low pressure and the resulting solid was thoroughly washed with hexanes (3×5 mL) and dried to give the sodium salt as a colorless powder. Salts were used directly without further characterization.

Scheme 2. General method for the formation of alkyl tantalum complexes

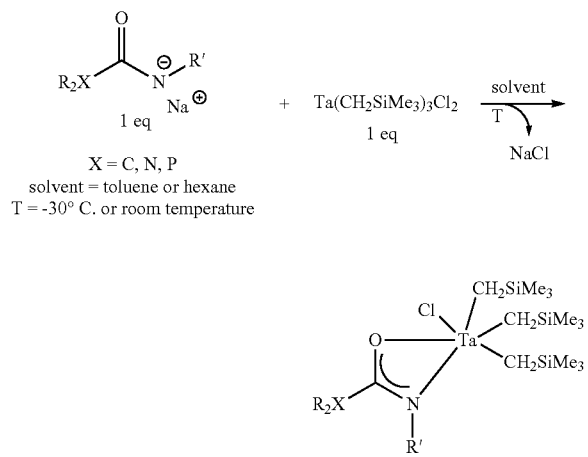

Synthesis and Characterization of Tantalum Based Ureate Complexes

Scheme 3. Synthesis of tantalum complexes supported by cyclic ureate ligands

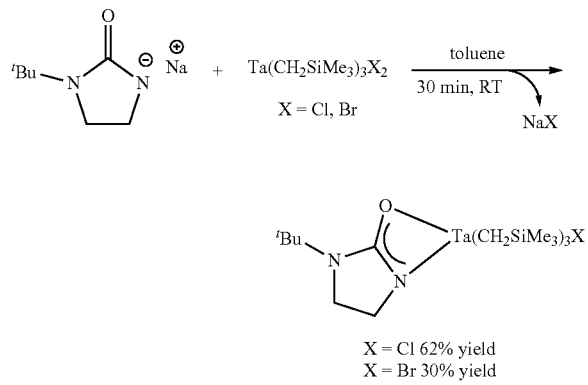

X = Cl 62% yield
X = Br 30% yield

Figure 28:
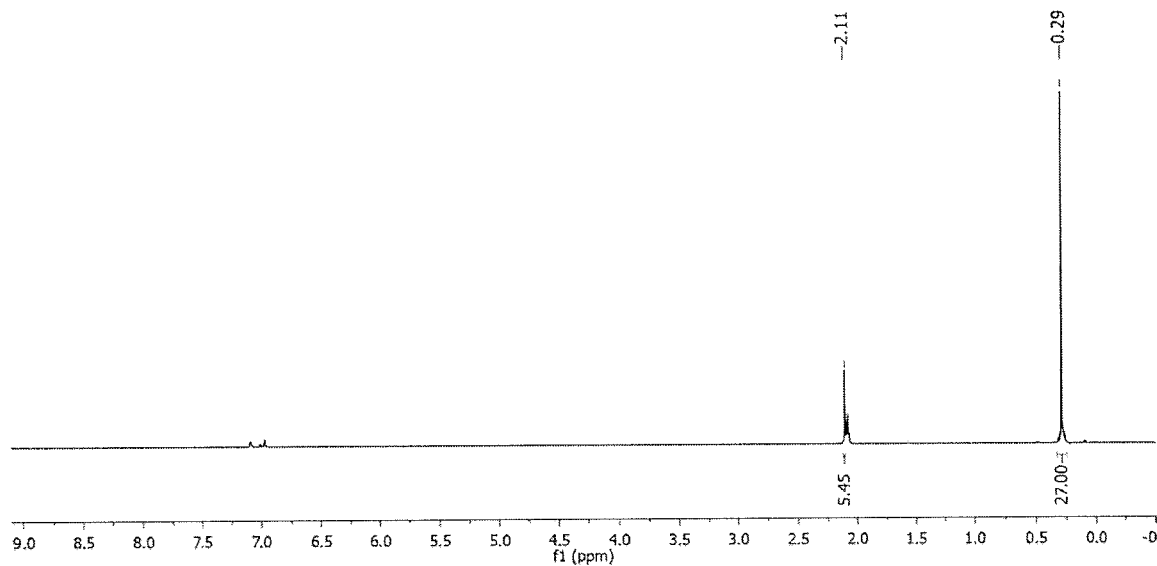
FIG. 28 is a ¹H NMR spectrum (300 MHz, toluene-d₈, 298 K) of Ta(CH₂SiMe₃)₃Br₂.

FIG. 28 is a $^1$H NMR spectrum (300 MHz, toluene-d$_8$, 298 K) of Ta(CH$_2$SiMe$_3$)$_3$Br$_2$.

Synthesis of $^{tBu}$LTa(CH$_2$SiMe$_3$)$_3$Cl

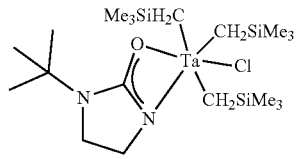

A suspension of $^{tBu}$L$^-$Na$^+$ (71 mg, 0.43 mmol) in toluene (3 mL) was added dropwise at room temperature to a solution of Ta(CH$_2$SiMe$_3$)Cl$_2$ (200 mg, 0.39 mmol) in toluene (3 mL). The reaction mixture was stirred for 30 min. The volatiles were then removed in vacuo and the title complex was extracted with hexanes (3×5 mL) and filtered over celite. The resulting organic solution was concentrated to approx. 3 mL and stored in a freezer at −30° C. A large crop of crystals were formed overnight which were further dried affording the title compound as pale yellow crystals. Yield (150 mg, 62%). $^1$H NMR (benzene-d$_6$, 300 MHz, 298 K): δ 3.36-3.23 (m, 2H, NCH$_2$), 2.75-2.62 (m, 2H, NCH$_2$), 1.57 (s, 6H, CH$_2$SiMe$_3$), 1.06 (s, 9H, NC(CH$_3$)$_3$), 0.36 (s, 27H, SiCH$_3$) ppm. $^{13}$C NMR (benzene-d$_6$, 75 MHz, 298 K): δ 171.36 (C=O), 90.19 (CH$_2$SiMe$_3$), 53.68 (NC(CH$_3$)$_3$), 45.38 (NCH$_2$), 44.41 (NCH$_2$), 27.96 (NC(CH$_3$)$_3$), 2.79 (SiCH$_3$) ppm. LRMS (ESI): m/z: 531 (M-CH$_2$SiMe$_3$-H$^+$), 443 (M-2CH$_2$SiMe$_3$-2H$^+$). Anal. Calcd. for C$_{19}$H$_{47}$ClN$_2$OSi$_3$Ta: C, 36.79; H, 7.64; N, 4.52; Found: C, 36.44; H, 7.69; N, 4.59.

Figure 29:
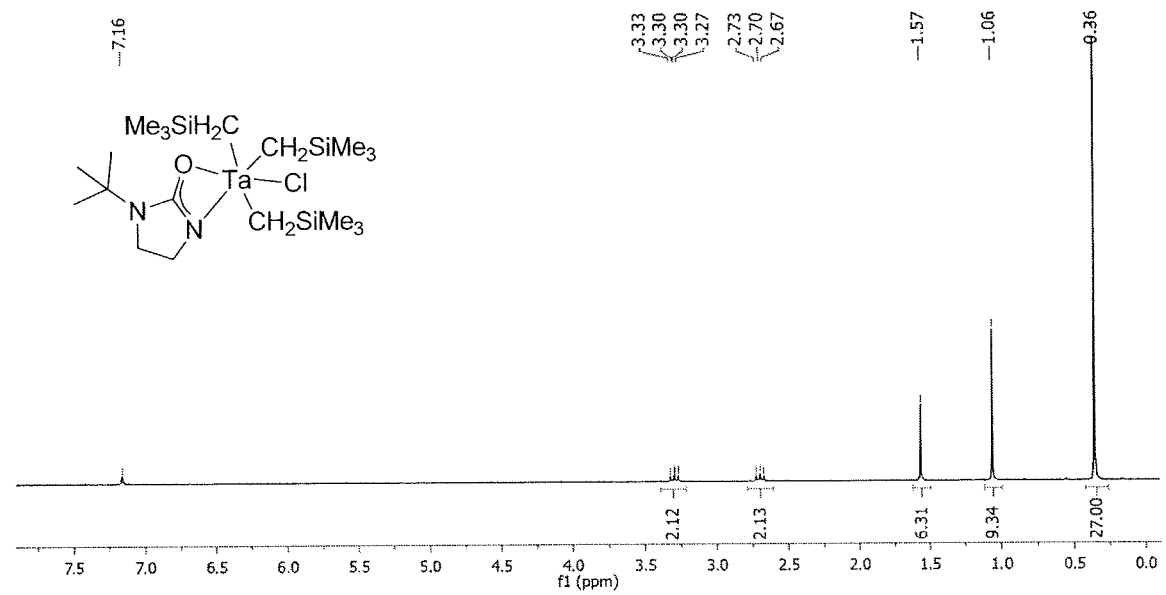
FIG. 29 is a ¹H NMR spectrum (300 MHz, benzene-d₆, 298 K) of $^{tBu}$LTa(CH₂SiMe₃)₃Cl.
Figure 30:
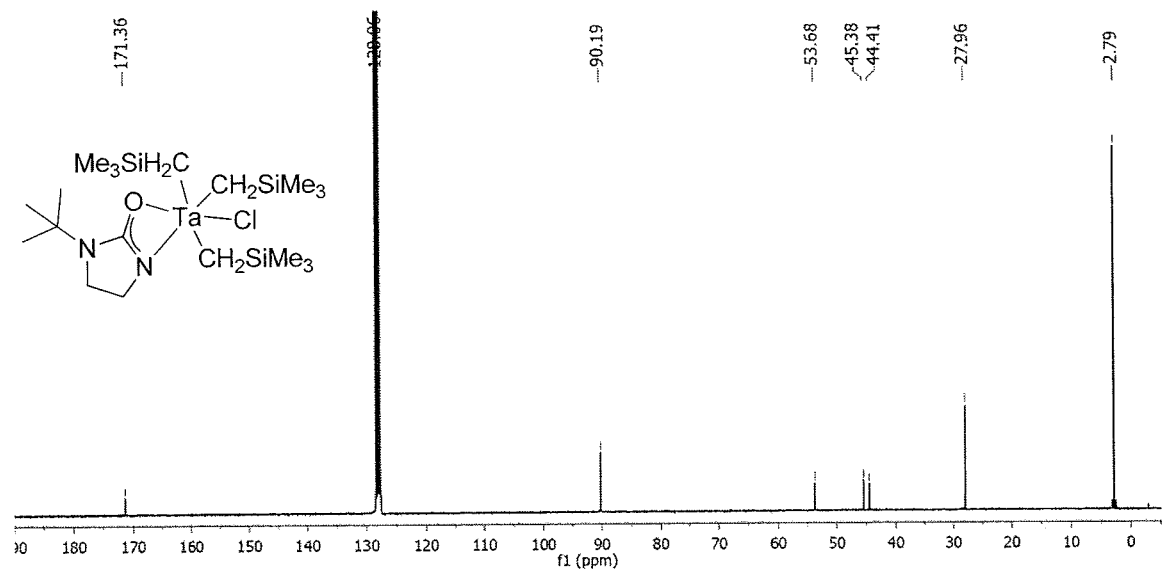
FIG. 30 is a ¹³C NMR spectrum (75 MHz, benzene-d₆, 298 K) of $^{tBu}$LTa(CH₂SiMe₃)₃Cl.

FIG. 29 is a $^1$H NMR spectrum (300 MHz, benzene-d$_6$, 298 K) of $^{tBu}$LTa(CH$_2$SiMe$_3$)$_3$Cl. FIG. 30 is a $^{13}$C NMR spectrum (75 MHz, benzene-d$_6$, 298 K) of $^{tBu}$LTa(CH$_2$SiMe$_3$)$_3$Cl.

Synthesis of $^{tBu}$LTa(CH$_2$SiMe$_3$)$_3$Br

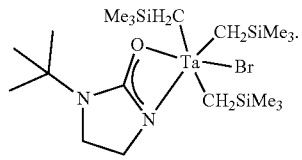

A suspension of $^{tBu}$L$^-$Na$^+$ (30 mg, 0.19 mmol) in toluene (3 mL) was added dropwise at room temperature to a solution of Ta(CH$_2$SiMe$_3$)Cl$_2$ (106 mg, 0.18 mmol) in toluene (3 mL). The reaction mixture was stirred for 30 min. The volatiles were then removed in vacuo and the title complex was extracted with hexanes (3×5 mL) and filtered over celite. The resulting organic solution was concentrated to approx. 3 mL and stored in a freezer at −30° C. A large crop of crystals were formed overnight which were further dried affording the title compound as pale yellow crystals. Yield (35 mg, 30%). $^1$H NMR (benzene-d$_6$, 400 MHz, 298 K): δ 3.31-3.24 (m, 2H, NCH$_2$), 2.72-2.65 (m, 2H, NCH$_2$), 1.62 (s, 6H, CH$_2$SiMe$_3$), 1.05 (s, 9H, NC(CH$_3$)$_3$), 0.37 (s, 27H, SiCH$_3$) ppm. $^{13}$C NMR (benzene-d$_6$, 75 MHz, 298 K): δ 171.18 (C=O), 94.33 (CH$_2$SiMe$_3$), 53.78 (NC(CH$_3$)$_3$), 45.34 (NCH$_2$), 44.16 (NCH$_2$), 27.96 (NC(CH$_3$)$_3$), 2.91 (SiCH$_3$) ppm.

Figure 31:
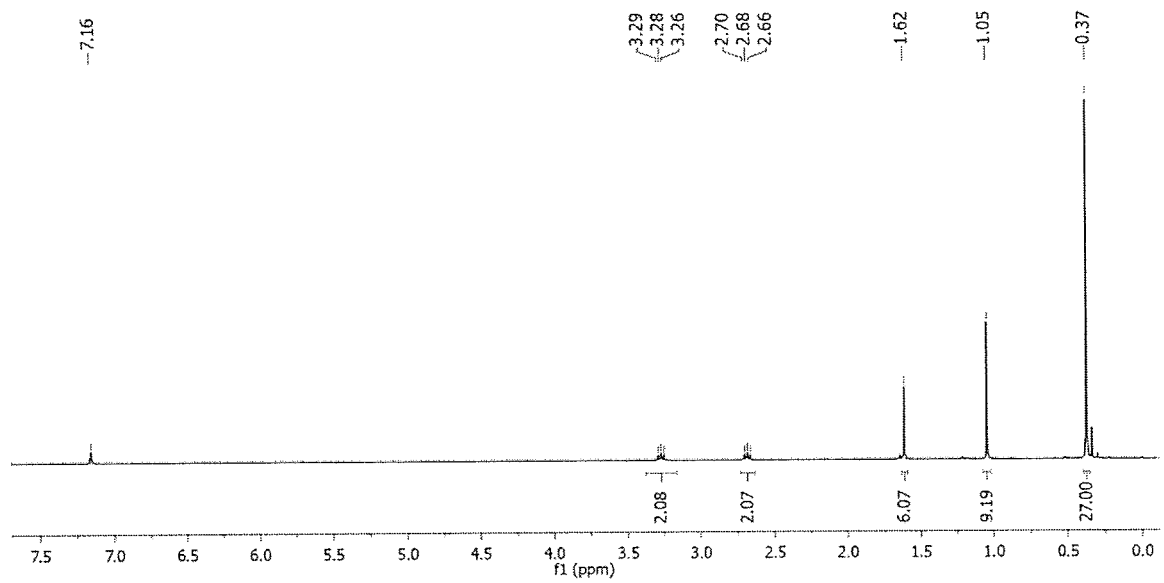
FIG. 31 is a ¹H NMR spectrum (400 MHz, benzene-d₆, 298 K) of $^{tBu}$LTa(CH₂SiMe₃)₃Br.
Figure 32:
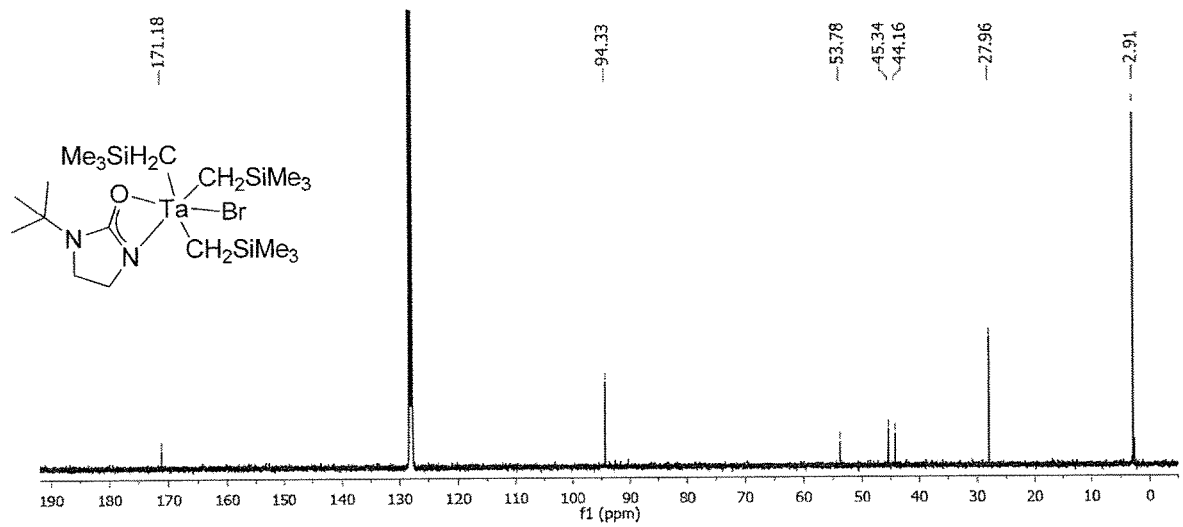

FIG. 31 is a $^1$H NMR spectrum (400 MHz, benzene-d$_6$, 298 K) of $^{tBu}$LTa(CH$_2$SiMe$_3$)$_3$Br. FIG. 32 is a $^{13}$C NMR spectrum (100 MHz, benzene-d$_6$, 298 K) of $^{tBu}$LTa(CH$_2$SiMe$_3$)$_3$Br.

Synthesis and Characterization of Tantalum Based Ureate Complexes

Synthesis of LTa(CH$_2$SiMe$_3$)$_3$Cl

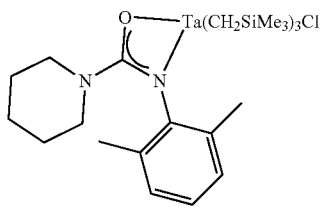

A suspension of L$^-$Na$^+$ (206 mg, 0.81 mmol) in toluene (5 mL) was added dropwise at room temperature to a solution of Ta(CH$_2$SiMe$_3$)Cl$_2$ (378 mg, 0.736 mmol) in toluene (6 mL). The reaction mixture was stirred for 30 min. The volatiles were then removed in vacuo and the title complex was extracted with hexanes (3×5 mL) and filtered over celite. The resulting organic solution was concentrated to approx. 3 mL and stored in a freezer at −30° C. Over a week period, a large amount of solid precipitated. The mixture was then filtered and the resulting solid was dried in vacuo to form the desired complex. Yield (370 mg, 71%). $^1$H NMR (benzene-d$_6$, 300 MHz, 298 K): δ 6.92-6.80 (m, 3H, C$_6$H$_3$), 3.52-3.85 (m, 2H, CH$_2$), 2.21 (s, 6H, CH$_2$SiMe$_3$), 1.41 (s, 6H, CH$_3$), 0.39 (s, 27H, SiCH$_3$) ppm.

Figure 41:
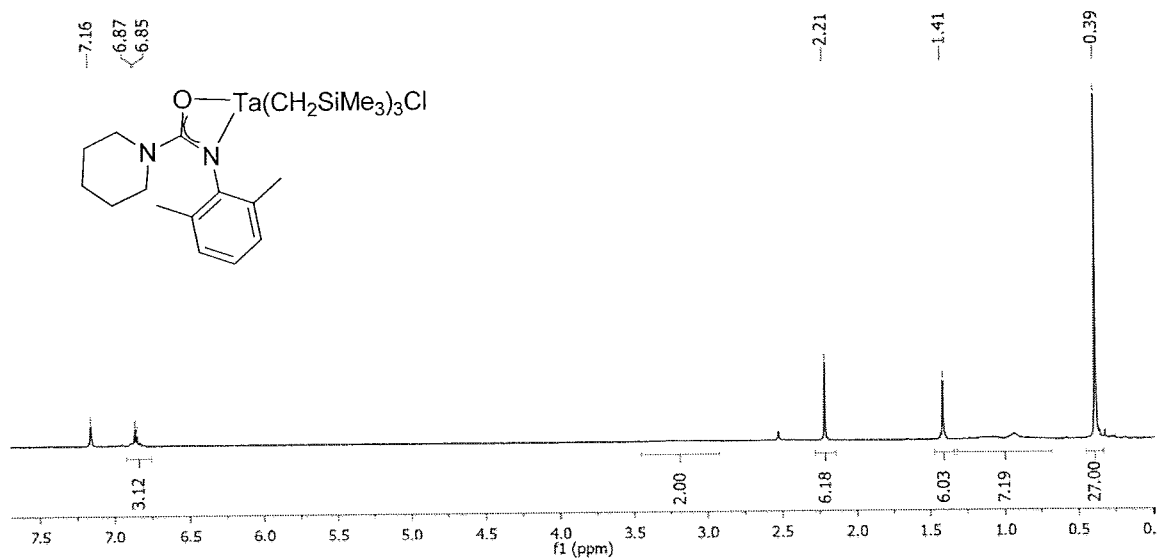
FIG. 41 is a ¹H NMR spectrum (300 MHz, benzene-d₆, 298 K) of LTa(CH₂SiMe₃)₃Cl.

FIG. 41 is a $^1$H NMR spectrum (300 MHz, benzene-d$_6$, 298 K) of LTa(CH$_2$SiMe$_3$)$_3$Cl.

3.4 Hydroaminoalkylation Reaction:

General Procedure for Hydroaminoalkylation Reaction:

Solid tantalum precursor (0.0025 mmol) was weighed into a vial, followed by addition of the chosen ligand salt (0.025 mmol) d$_8$-toluene (0.3 g) was added, and the resultant mixture was left for 15 minutes. A chosen amine substrate was then added (0.5 mmol), followed by the alkene (0.5 mmol). The resultant reaction mixture was transferred into a J. Young NMR tube and the vial was rinsed with an additional 0.2 g of d$_8$-toluene. An initial $^1$H NMR spectrum was recorded and the sample was added to a pre-heated oil bath. All conversion values were determined by $^1$H NMR spectroscopy. After removal of all reaction solvent, pentane was added to the reaction mixture and a white precipitate was formed instantaneously. Residual tantalum salts and proteo-ligands were then removed by filtering the pentane solution at −80° C. Unreacted amine or alkene starting materials were removed at 40° C. under low pressure. In all cases, $^1$H NMR spectroscopy still showed the presence of proteo-ligands in low amounts (2-4%), which can be entirely removed by column chromatography. N-(2-propylhexyl)aniline and N-(2-ethylpentyl)aniline showed signs of decomposition while heated under vacuum, and therefore must be purified by column chromatography.

N-(2-methyloctyl)aniline:

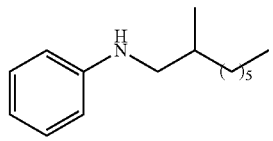

N-methylaniline (54 mg, 0.5 mmol), 1-octene (0.056 g, 0.5 mmol), Ta(CH$_2$SiMe$_3$)$_3$Cl$_2$ (13 mg, 0.025 mmol), L4 (8 mg, 0.025 mmol). Reaction time: 2 h. Yield 88%. $^1$H NMR (CDCl$_3$, 300 MHz, 298 K): δ 7.24-7.16 (m, 2H, bum-C$_6$H$_5$), 6.75-6.67 (m, 1H, p-C$_6$H$_5$), 6.67-6.60 (m, 2H, o-C$_6$H$_5$), 3.69 (br s, 1H, NH), 3.08 (dd, J$_{H-H}$=12.8, 5.8 Hz, 1H, NC(H)H), 2.91 (dd, J$_{H-H}$=12.2, 7.3 Hz, 1H, NC(H)H), 1.86-1.68 (m, 1H, 1.53-1.14 (overlapping m, 10H, CH$_2$), 1.00 (d, J$_{H-H}$=6.6 Hz, 3H, CHCH$_3$), 0.97-0.89 (t, J$_{H-H}$=6.1 Hz, 3H, CH$_2$CH$_3$) ppm. The chemical shifts for the title compound match those reported by Hartwig et al.

N-(cyclooctylmethyl)aniline

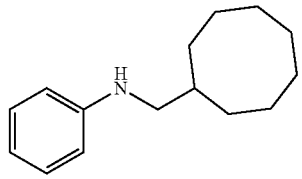 [SMILES: c1ccc(NCC2CCCCCCC2)cc1]

N-methylaniline (54 mg, 0.5 mmol), cyclooctene (55 mg, 0.5 mmol), Ta(CH$_2$SiMe$_3$)$_3$Cl$_2$ (13 mg, 0.025 mmol), L5 (8 mg, 0.025 mmol). Reaction time: 6 h. Yield 83%. $^1$H NMR (CDCl$_3$, 300 MHz, 298 K): δ 7.20 (dd, J$_{H-H}$=8.5, 7.4 Hz, 2H, m-C$_6$H$_5$), 6.70 (t, J$_{H-H}$=6.7 Hz, 1H, p-C$_6$H$_5$), 6.62 (dd, J$_{H-H}$=8.5, 0.9 Hz, 2H, o-C$_6$H$_5$), 3.71 (br s, 1H, NH), 2.08 (d, J$_{H-H}$=6.8 Hz, NCH$_2$), 1.92-1.27 (overlapping m, 13H, CH$_2$ and CH) ppm.

4-methoxy-N-(2-methyloctyl)aniline

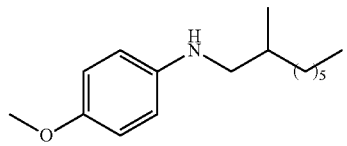

4-methoxy-N-methylaniline (96 mg, 0.5 mmol), 1-octene (0.056 g, 0.5 mmol), Ta(CH$_2$SiMe$_3$)$_3$Cl$_2$ (13 mg, 0.025 mmol), L4 (8 mg, 0.025 mmol). Reaction time: 2 h. Yield 77%. $^1$H NMR (CDCl$_3$, 300 MHz, 298 K): δ 6.84-6.74 (m, 2H, m-C$_6$H$_4$), 6.63-6.55 (m, 2H, o-C$_6$H$_4$), 3.76 (s, 3H, OCH$_3$), 3.38 (br s, 1H, NH), 3.02 (dd, J$_{H-H}$=5.8, 12.1 Hz, 1H, NC(H)H), 3.02 (dd, J$_{H-H}$=7.8, 12.1 Hz, 1H, NC(H)H), 1.82-1.64 (m, 1H, CH), 1.55-1.05 (m, 10H, CH$_2$), 0.98 (d, J$_{H-H}$=6.6 Hz, 3H, CHCH$_3$), 0.91 (t, J$_{H-H}$=6.7 Hz, 3H, CH$_2$CH$_3$) ppm. The chemical shifts for the title compound match those previously reported in the literature.

4-bromo-N-(2-methyloctyl)aniline

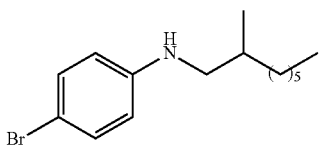

4-bromo-N-methylaniline (93 mg, 0.5 mmol), 1-octene (0.056 g, 0.5 mmol), Ta(CH$_2$SiMe$_3$)$_3$Cl$_2$ (13 mg, 0.025 mmol), L4 (8 mg, 0.025 mmol). Reaction time: 2 h. Yield 86%. $^1$H NMR (CDCl$_3$, 300 MHz, 298 K): δ 7.23 (d, J$_{H-H}$=8.7 Hz, 2H, m-C$_6$H$_4$), 6.48 (d, J$_{H-H}$=8.9 Hz, 2H, o-C$_6$H$_4$), 3.92 (br s, 1H, NH), 3.01 (dd, J$_{H-H}$=5.9, 12.2 Hz, 1H, NC(H)H), 2.84 (dd, J$_{H-H}$=7.1, 12.1 Hz, 1H, NC(H)H), 1.78-1.65 (m, 1H, CH), 1.51-1.08 (m, 10H, CH$_2$), 0.96 (d, J$_{H-H}$=6.6 Hz, 3H, CHCH$_3$), 0.89 (t, J$_{H-H}$=6.9 Hz, 3H, CH$_2$CH$_3$) ppm. $^{13}$C NMR (CDCl$_3$, 75 MHz, 298 K): δ 148.51 (i-C$_6$H$_4$), 129.34 (m-C$_6$H$_4$), 117.24 (p-C$_6$H$_4$), 112.87 (o-C$_6$H$_4$), 48.11, 47.99, 37.45, 37.28, 36.79, 36.56, 29.68, 27.37, 27.00, 26.11, 25.95, 25.04, 14.94 (CH$_3$), 14.48 (CH$_3$) ppm.

Figure 5:
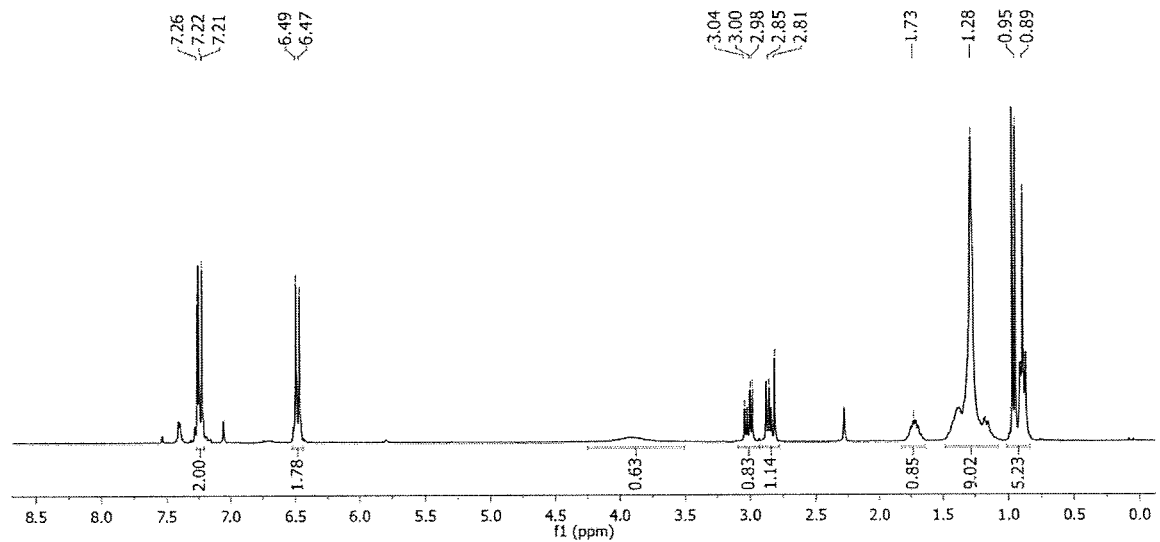
FIG. 5 is a ¹H NMR spectrum (300 MHz, CDCl₃, 298 K) of 4-bromo-N-(2-methyloctyl)aniline.
Figure 6:
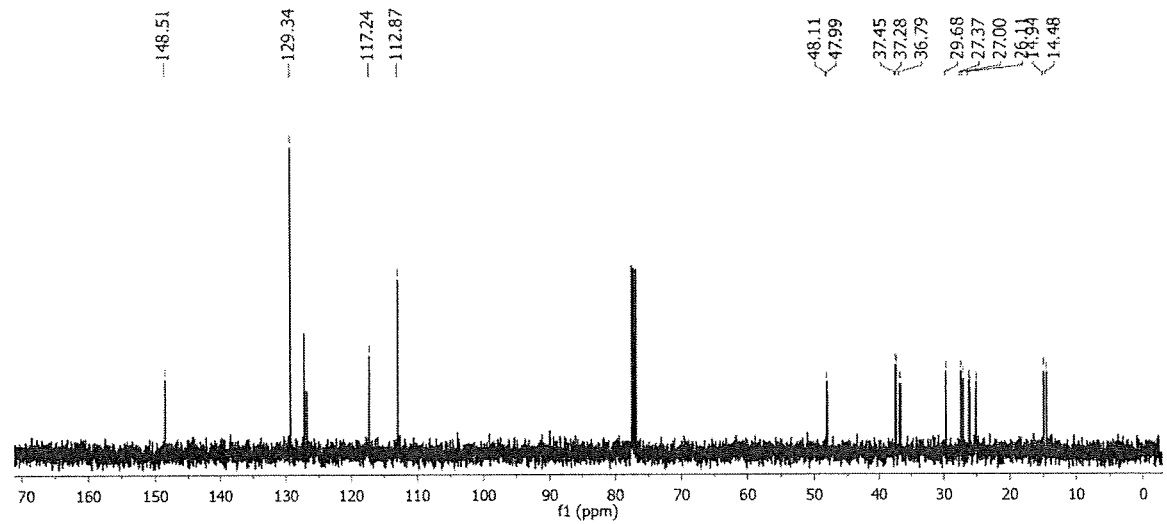
FIG. 6 is a ¹³C NMR spectrum (100 MHz, CDCl₃, 298 K) of 4-bromo-N-(2-methyloctyl)aniline.

FIG. 5 is a $^1$H NMR spectrum (300 MHz, CDCl$_3$, 298 K) of 4-bromo-N-(2-methyloctyl)aniline. FIG. 6 is a $^{13}$C NMR spectrum (100 MHz, CDCl$_3$, 298 K) of 4-bromo-N-(2-methyloctyl)aniline.

4-bromo-N-(cyclooctylmethyl)aniline

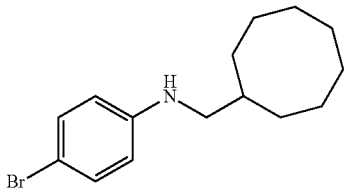 [SMILES: Clc1ccc(NCC2CCCCCCC2)cc1]

4-bromo-N-methylaniline (93 mg, 0.5 mmol), cyclooctene (55 mg, 0.5 mmol), Ta(CH$_2$SiMe$_3$)$_3$Cl$_2$ (13 mg, 0.025 mmol), L5 (8 mg, 0.025 mmol). Reaction time: 6 h. Yield 95%. $^1$H NMR (CDCl$_3$, 300 MHz, 298 K): δ 7.25 (d, J$_{H-H}$=8.8 Hz, m-C$_6$H$_4$), 6.47 (d, J$_{H-H}$=8.8 Hz, o-C$_6$H$_4$), 3.75 (br s, 1H, NH), 2.90 (d, J$_{H-H}$=6.8 Hz, NCH$_2$), 1.86-1.24 (overlapping m, 13H, CH and CH$_2$) ppm. $^{13}$C NMR (CDCl$_3$, 75 MHz, 298 K): δ 147.65 (i-C$_6$H$_4$), 131.95 (m-C$_6$H$_4$), 114.25 (o-C$_6$H$_4$), 108.40 (p-C$_6$H$_4$), 51.21 (NCH$_2$), 37.33 (CH$_2$), 30.67 (CH$_2$), 27.13 (CH$_2$), 26.41 (CH$_2$), 25.58 (CH$_2$) ppm.

Figure 7:
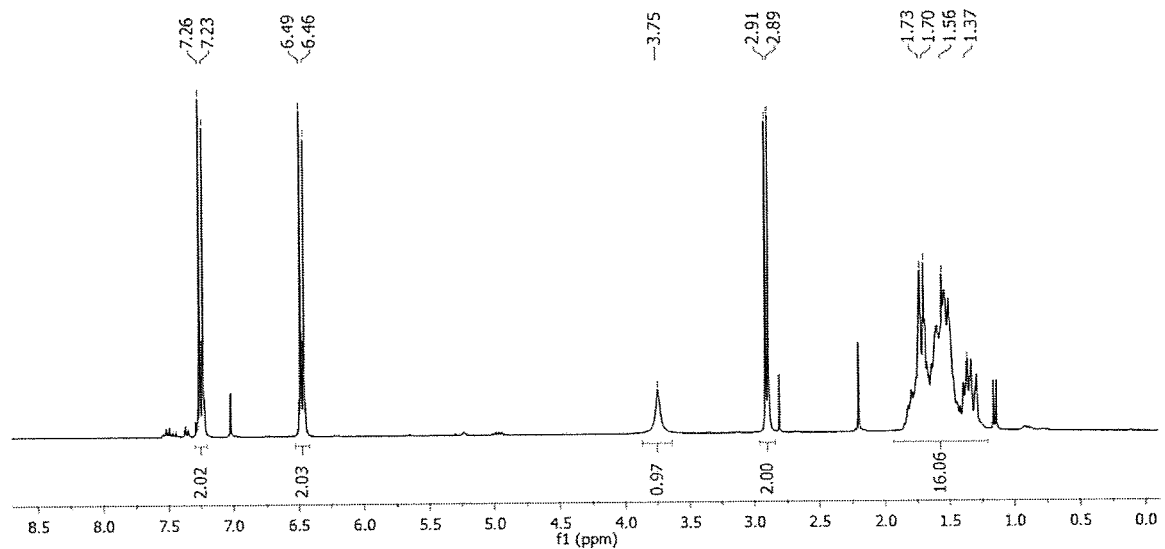
FIG. 7 is a ¹H NMR spectrum (300 MHz, CDCl₃, 298 K) of 4-bromo-N-(cyclooctylmethyl)aniline.
Figure 8:
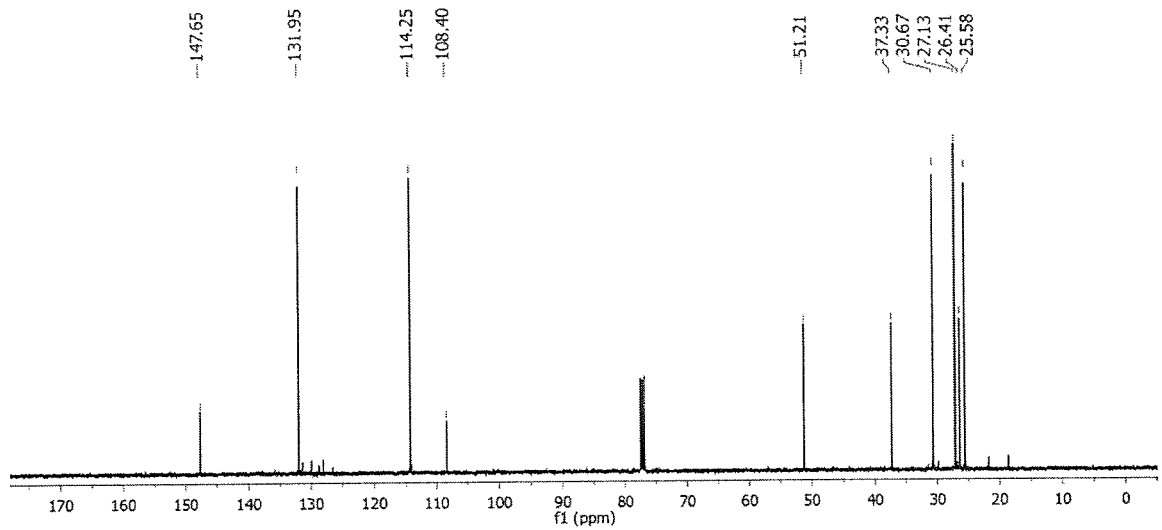
FIG. 8 is a ¹³C NMR spectrum (100 MHz, CDCl₃, 298 K) of 4-bromo-N-(cyclooctylmethyl)aniline.

FIG. 7 is a $^1$H NMR spectrum (300 MHz, CDCl3, 298 K) of 4-bromo-N-(cyclooctylmethyl)aniline. FIG. 8 is a $^{13}$C NMR spectrum (100 MHz, CDCl3, 298 K) of 4-bromo-N-(cyclooctylmethyl)aniline.

4-chloro-N-(2-methyloctyl)aniline

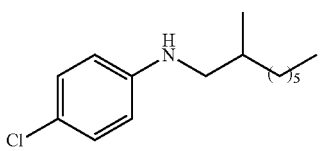

4-chloro-N-methylaniline (71 mg, 0.5 mmol), 1-octene (0.056 g, 0.5 mmol), Ta(CH$_2$SiMe$_3$)$_3$Cl$_2$ (13 mg, 0.025 mmol), L4 (8 mg, 0.025 mmol). Reaction time: 2 h. Yield 90%. $^1$H NMR (CDCl$_3$, 300 MHz, 298 K): δ 7.12 (d, J$_{H-H}$=8.8 Hz, 2H, m-C$_6$H$_5$), 6.52 (d, J$_{H-H}$=8.8 Hz, 2H, o-C$_6$H$_5$), 3.78 (br s, 1H, NH), 3.02 (dd, J$_{H-H}$=5.9, 12.2 Hz, 1H, NC(H)H), 2.86 (dd, J$_{H-H}$=7.2, 12.2 Hz, 1H, NC(H)H), 1.82-1.65 (m, 1H, 1.51-1.09 (m, 10H, CH$_2$), 0.97 (d, J$_{H-H}$=6.6 Hz, 3H, CHCH$_3$), 0.91 (t, J$_{H-H}$=6.8 Hz, 3H, CH$_2$CH$_3$) ppm. The chemical shifts for the title compound match those previously reported in the literature.

4-chloro-N-(cyclooctylmethyl)aniline

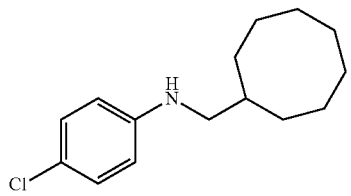

4-chloro-N-methylaniline (71 mg, 0.5 mmol), cyclooctene (55 mg, 0.5 mmol), Ta(CH$_2$SiMe$_3$)$_3$Cl$_2$ (13 mg, 0.025 mmol), L5 (8 mg, 0.025 mmol). Reaction time: 6 h. Yield 93%. $^1$H NMR (CDCl$_3$, 300 MHz, 298 K): δ 7.10 (d, J$_{H-H}$=8.8 Hz, m-C$_6$H$_4$), 6.51 (d, J$_{H-H}$=8.8 Hz, o-C$_6$H$_4$), 3.71 (br s, 1H, NH), 2.90 (d, J$_{H-H}$=6.8 Hz, NCH$_2$), 1.87-1.21 (overlapping m, 13H, CH and CH$_2$). ppm. $^{13}$C NMR (CDCl$_3$, 75 MHz, 298 K): δ 147.29 (i-C$_6$H$_4$), 129.10 (m-C$_6$H$_4$), 121.41 (p-C$_6$H$_4$), 113.73 (o-C$_6$H$_4$), 51.32 (NCH$_2$), 37.38 (CH$_2$), 30.70 (CH$_2$), 27.14 (CH$_2$), 26.43 (CH$_2$), 25.59 (CH$_2$) ppm.

Figure 9:
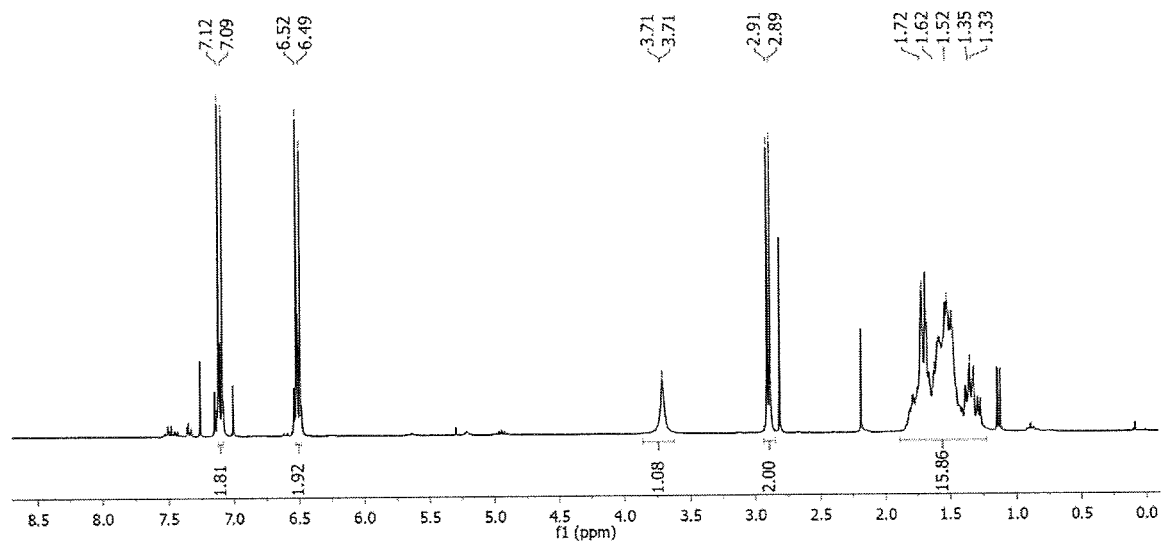
FIG. 9 is a ¹H NMR spectrum (300 MHz, CDCl₃, 298 K) of 4-chloro-N-(cyclooctylmethyl)aniline.
Figure 10:
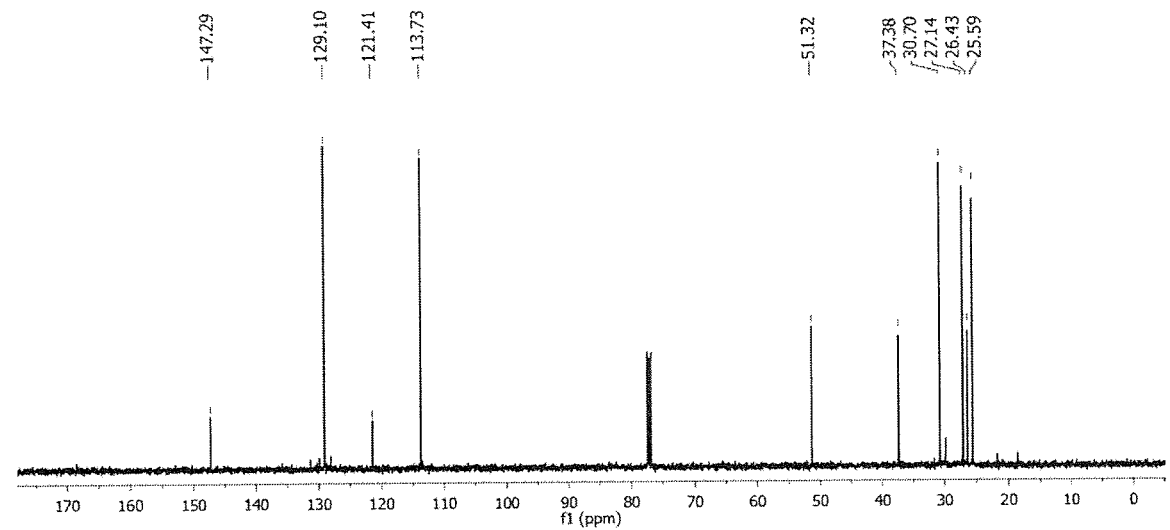
FIG. 10 is a ¹³C NMR spectrum (100 MHz, CDCl₃, 298 K) of 4-chloro-N-(cyclooctylmethyl)aniline.

FIG. 9 is a $^1$H NMR spectrum (300 MHz, CDCl3, 298 K) of 4-chloro-N-(cyclooctylmethyl)aniline. FIG. 10 is a $^{13}$C NMR spectrum (100 MHz, CDCl$_3$, 298 K) of 4-chloro-N-(cyclooctylmethyl)aniline.

4-fluoro-N-(2-methyloctyl)aniline

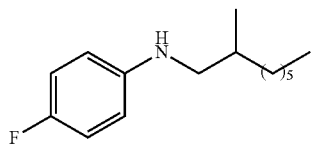

4-fluoro-N-methylaniline (63 mg, 0.5 mmol), 1-octene (0.056 g, 0.5 mmol), Ta(CH$_2$SiMe$_3$)$_3$Cl$_2$ (13 mg, 0.025 mmol), L4 (8 mg, 0.025 mmol). Reaction time: 2 h. Yield 88%. $^1$H NMR (CDCl$_3$, 300 MHz, 298 K): δ 6.89 (t, J$_{H-H}$=8.8 Hz, 2H, m-C$_6$H$_5$), 6.59-6.50 (m, 2H, o-C$_6$H$_5$), 3.57 (br s, 1H, NH), 3.02 (dd, J$_{H-H}$=5.9, 12.1 Hz, 1H, NC(H)H), 2.85 (dd, J$_{H-H}$=7.2, 12.0 Hz, 1H, NC(H)H), 1.82-1.65 (m, 1H, 1.51-1.11 (m, 10H, CH$_2$), 0.98 (d, J$_{H-H}$=6.7 Hz, 3H, CHCH$_3$), 0.91 (t, JH—H=6.9 Hz, 3H, CH$_2$CH$_3$) ppm.

25
N-(cyclooctylmethyl)-4-fluoroaniline

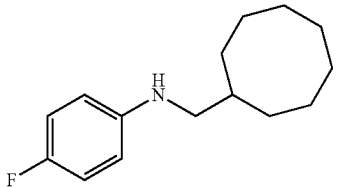 [SMILES: Fc1ccc(NCC2CCCCCCC2)cc1]

4-fluoro-N-methylaniline (63 mg, 0.5 mmol), cyclooctene (55 mg, 0.5 mmol), Ta(CH$_2$SiMe$_3$)$_3$Cl$_2$ (13 mg, 0.025 mmol), L5 (8 mg, 0.025 mmol). Reaction time: 6 h. Yield 88%. $^1$H NMR (CDCl$_3$, 300 MHz, 298 K): δ 6.89 (t, J$_{H-H}$=8.7 Hz, 2H, m-C$_6$H$_4$), 6.57-6.49 (m, 2H, o-C$_6$H$_4$), 3.58 (br s, 1H, NH), 2.90 (d, J$_{H-H}$=6.7 Hz, 2H, NCH$_2$), 1.88-1.22 (overlapping m, 13H, CH and CH$_2$) ppm. $^{13}$C NMR (CDCl$_3$, 100 MHz, 298 K): δ 155.68 (d, J$_{C-F}$=234.2 Hz, p-C$_6$H$_4$), 145.05 (i-C$_6$H$_4$), 115.66 (d, J$_{C-F}$=22.2 Hz, m-C$_6$H$_4$), 113.49 (d, J$_{C-F}$=7.3 Hz, o-C$_6$H$_4$), 51.99 (NCH$_2$), 37.41 (CH$_2$), 30.72 (CH$_2$), 27.15 (CH$_2$), 26.43 (CH$_2$), 25.60 (CH$_2$) ppm. $^{19}$F NMR (CDCl$_3$, 282.4 MHz, 298 K): δ −129.00 (tt, J$_{H-F}$=4.5 Hz, 1F, C$_6$H$_4$F) ppm.

Figure 11:
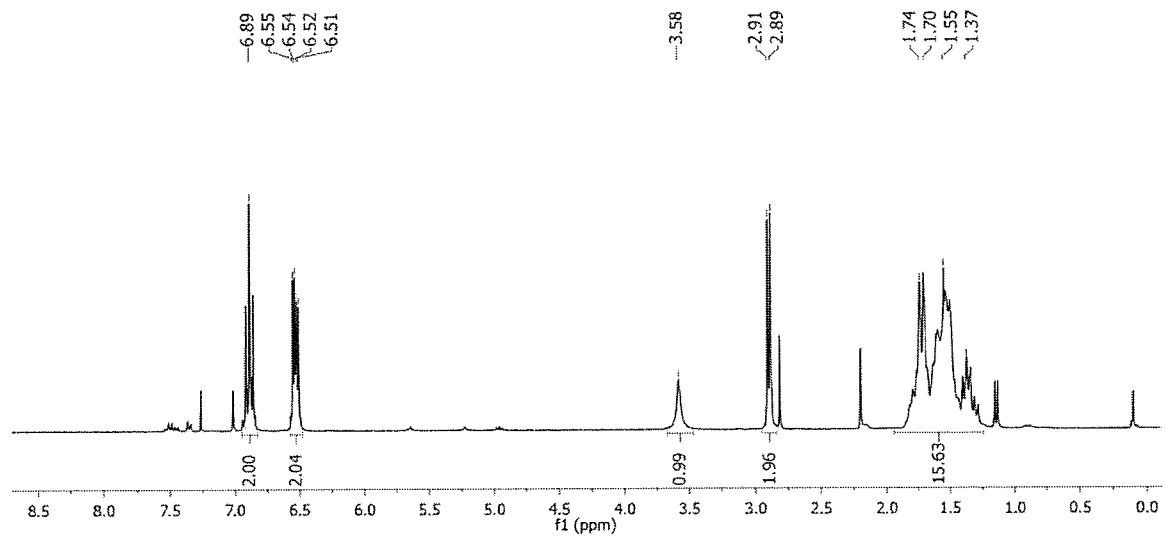
FIG. 11 is a ¹H NMR spectrum (300 MHz, CDCl₃, 298 K) of N-(cyclooctylmethyl)-4-fluoroaniline.
Figure 12:
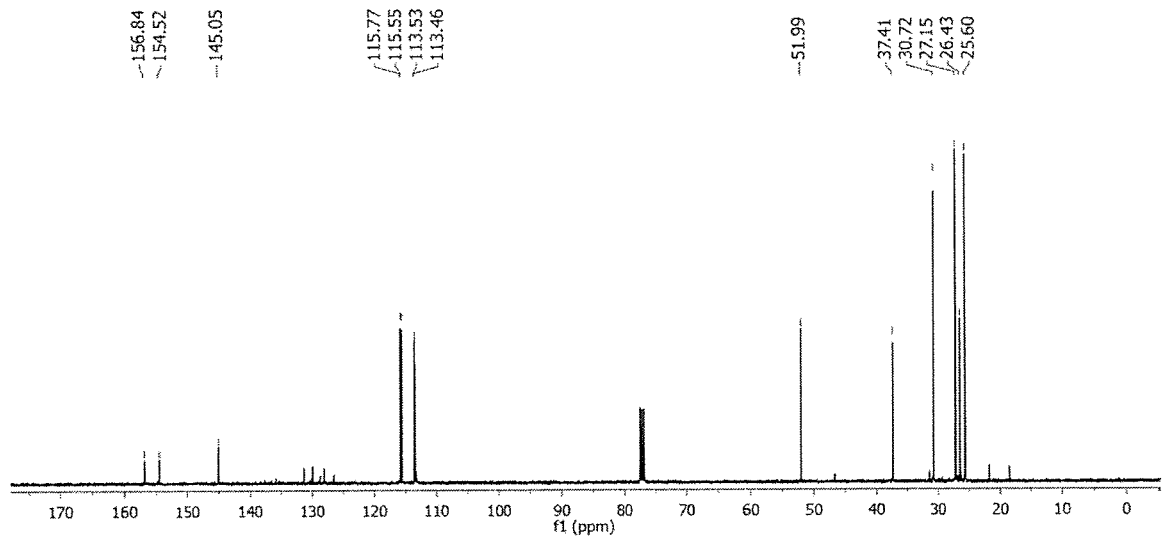
FIG. 12 is a ¹³C NMR spectrum (75 MHz, CDCl₃, 298 K) of N-(cyclooctylmethyl)-4-fluoroaniline.

FIG. 11 is a $^1$H NMR spectrum (300 MHz, CDCl3, 298 K) of N-(cyclooctylmethyl)-4-fluoroaniline. FIG. 12 is a $^{13}$C NMR spectrum (75 MHz, CDCl3, 298 K) of N-(cyclooctylmethyl)-4-fluoroaniline N-(2-methyloctyl)-4-(trifluoromethoxy)aniline

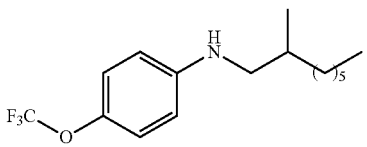

N-methyl-4-(trifluoromethoxy)aniline (96 mg, 0.5 mmol), 1-octene (0.056 g, 0.5 mmol), Ta(CH$_2$SiMe$_3$)$_3$Cl$_2$ (13 mg, 0.025 mmol), L4 (8 mg, 0.025 mmol). Reaction time: 3 h. Yield 92%. $^1$H NMR (CDCl$_3$, 300 MHz, 298 K): δ 7.03 (d, J$_{H-H}$=8.2 Hz, 2H, m-C$_6$H$_4$), 6.59-6.50 (m, 2H, o-C$_6$H$_4$), 3.80 (br s, 1H, NH), 3.03 (dd, J$_{H-H}$=5.9, 12.2 Hz, 1H, NC(H)H), 2.85 (dd, J$_{H-H}$=7.3, 12.2 Hz, 1H, NC(H)H), 1.82-1.64 (m, 1H, 1.51-1.09 (m, 10H, CH$_2$), 0.97 (d, J$_{H-H}$=6.7 Hz, 3H, CHCH$_3$), 0.90 (t, J$_{H-H}$=6.9 Hz, 3H, CH$_2$CH$_3$) ppm. $^{13}$C NMR (CDCl$_3$, 300 MHz, 298 K): δ 147.51 (i-C$_6$H$_5$), 122.53 (C$_6$H$_5$), 112.89 (C$_6$H$_5$), 50.67 (NCH$_2$), 34.90, 33.02, 32.00, 29.73, 27.07, 22.81, 18.17 (CH$_3$), 14.23 (CH$_3$) ppm. $^{19}$F NMR (CDCl$_3$, 282.4 MHz, 298 K): δ −58.81 (s, 3F, CF$_3$) ppm.

Figure 13:
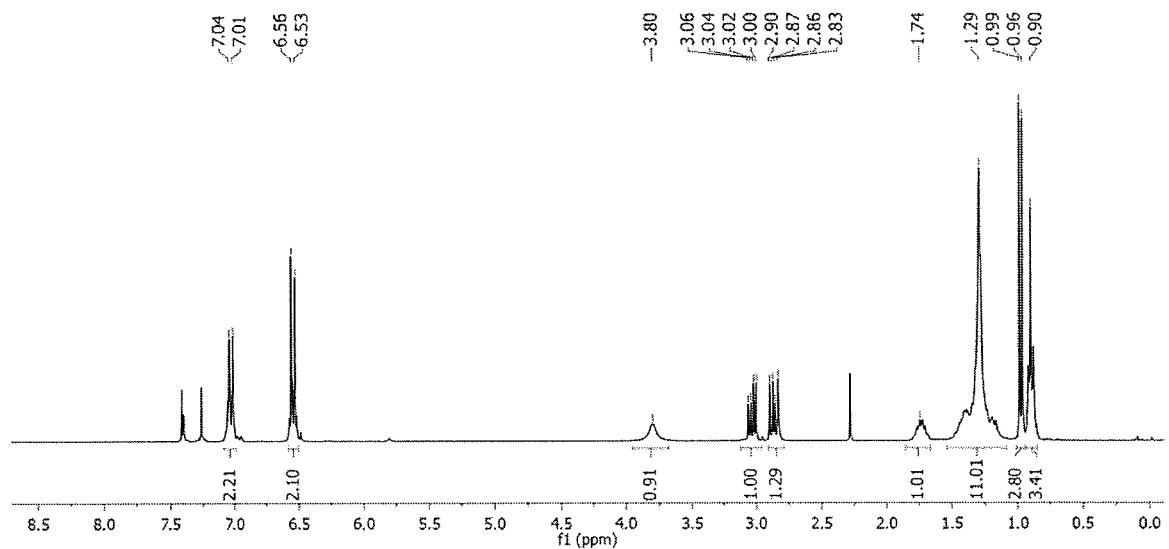
FIG. 13 is a ¹H NMR spectrum (300 MHz, CDCl₃, 298 K) of N-(2-methyloctyl)-4-(trifluoromethoxy)aniline.
Figure 14:
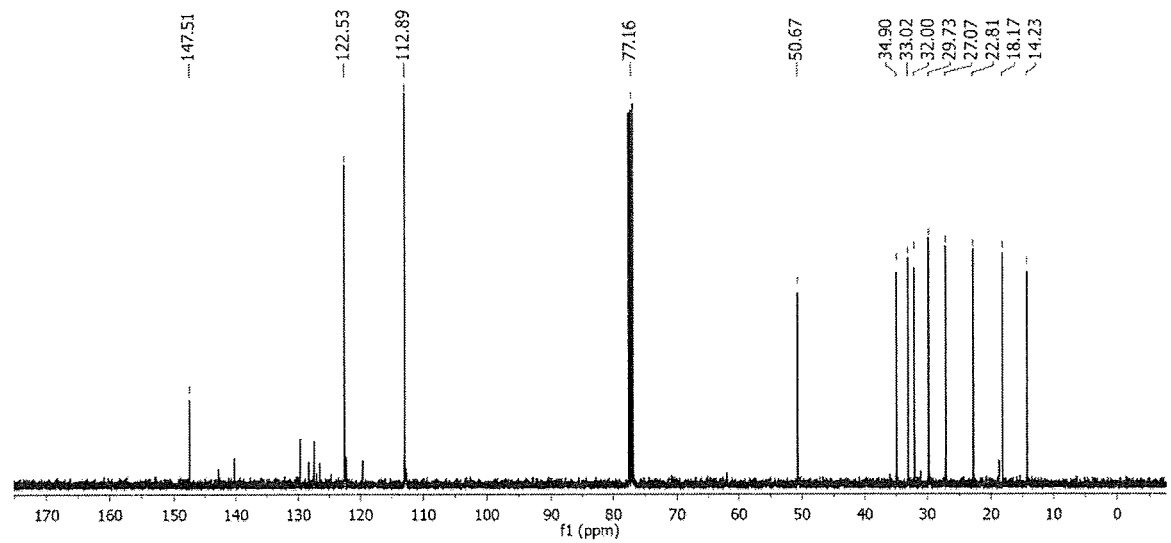
FIG. 14 is a ¹³C NMR spectrum (75 MHz, CDCl₃, 298 K) of N-(2-methyloctyl)-4-(trifluoromethoxy)aniline.

FIG. 13 is a $^1$H NMR spectrum (300 MHz, CDCl3, 298 K) of N-(2-methyloctyl)-4-(trifluoromethoxy)aniline. FIG. 14 is a $^{13}$C NMR spectrum (75 MHz, CDCl3, 298 K) of N-(2-methyloctyl)-4-(trifluoromethoxy)aniline.

26
N-(cyclooctylmethyl)-4-(trifluoromethoxy)aniline

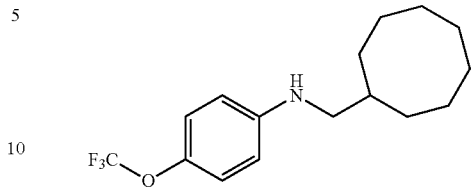

N-methyl-4-(trifluoromethoxy)aniline (96 mg, 0.5 mmol), cyclooctene (55 mg, 0.5 mmol), Ta(CH$_2$SiMe$_3$)$_3$Cl$_2$ (13 mg, 0.025 mmol), L5 (8 mg, 0.025 mmol). Reaction time: 6 h. Yield 85%. $^1$H NMR (CDCl$_3$, 300 MHz, 298 K): δ 7.03 (d, J$_{H-H}$=9.0 Hz, 2H, m-C$_6$H$_4$), 6.59-6.50 (m, 2H, o-C$_6$H$_4$), 3.77 (br s, 1H, NH), 0.2.92 (d, J$_{H-H}$=6.5 Hz, 1H, NCH$_2$), 1.89-1.21 (overlapping m, 13H, CH and CH$_2$) ppm. $^{13}$C NMR (CDCl$_3$, 75 MHz, 298 K): δ 147.55 (i-C$_6$H$_4$), 122.51 (C$_6$H$_4$), 112.81 (C$_6$H$_4$), 51.43 (NCH$_2$), 37.48, 30.73, 27.17, 26.44, 25.61 ppm. $^{19}$F NMR (CDCl$_3$, 282.4 MHz, 298 K): δ −58.79 (s, 3F, CF$_3$) ppm.

Figure 15:
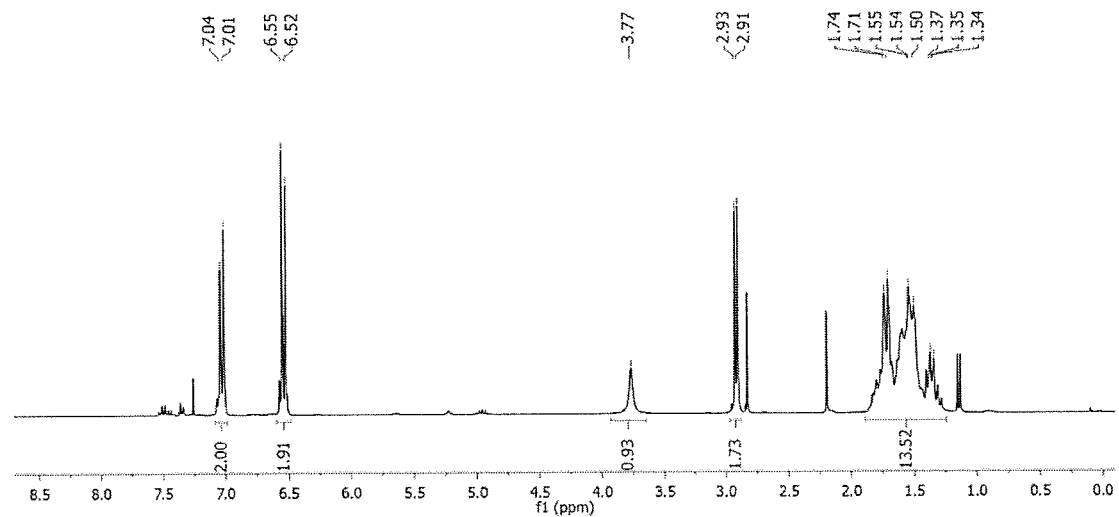
FIG. 15 is a ¹H NMR spectrum (300 MHz, CDCl₃, 298 K) of N-(cyclooctylmethyl)-4-(trifluoromethoxy)aniline.
Figure 16:
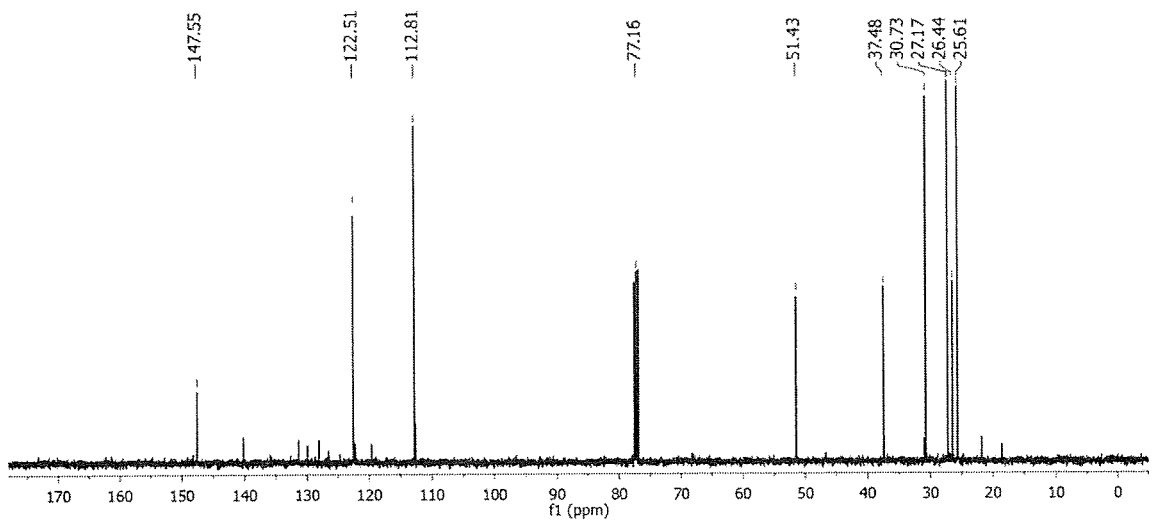
FIG. 16 is a ¹³C NMR spectrum (75 MHz, CDCl₃, 298 K) of N-(cyclooctylmethyl)-4-(trifluoromethoxy)aniline.

FIG. 15 is a $^1$H NMR spectrum (300 MHz, CDCl3, 298 K) of N-(cyclooctylmethyl)-4-(trifluoromethoxy)aniline. FIG. 16 is a $^{13}$C NMR spectrum (75 MHz, CDCl3, 298 K) of N-(cyclooctylmethyl)-4-(trifluoromethoxy)aniline.

N-(2-methyloctyl)benzo[d][1,3]dioxol-5-amine

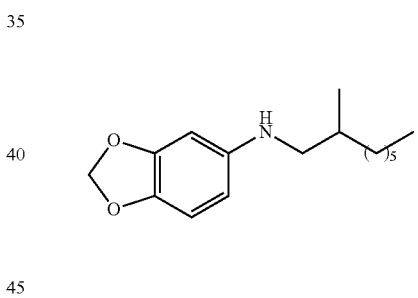

N-methylbenzo[d][1,3]dioxol-5-amine (76 mg, 0.5 mmol), 1-octene (0.056 g, 0.5 mmol), Ta(CH$_2$SiMe$_3$)$_3$Cl$_2$ (13 mg, 0.025 mmol), L4 (8 mg, 0.025 mmol). Reaction time: 2 h. Yield 85%. $^1$H NMR (CDCl$_3$, 300 MHz, 298 K): δ 6.66 (d, J$_{H-H}$=8.3 Hz, 2H, m-C$_6$H$_3$), 6.25 (d, J$_{H-H}$=8.3 Hz, 1H, o-C$_6$H$_3$), 6.04 (dd, J$_{H-H}$=2.3, 8.3 Hz, 1H, o-C$_6$H$_3$), 5.85 (s, 2H, OCH$_2$), 3.48 (br s, 1H, NH), 2.99 (dd, J$_{H-H}$=5.9, 12.0 Hz, 1H, NC(H)H), 2.84 (dd, J$_{H-H}$=5.0, 12.2 Hz, 1H, NC(H)H), 1.81-1.62 (m, 1H, 1.50-1.08 (m, 10H, CH$_2$), 0.97 (d, J$_{H-H}$=6.7 Hz, 3H, CHCH$_3$), 0.91 (t, J$_{H-H}$=7.1 Hz, 3H, CH$_2$CH$_3$) ppm. $^{13}$C NMR (CDCl$_3$, 75 MHz, 298 K): δ 148.46 (i-C$_6$H$_3$), 144.64 (m-C$_6$H$_3$), 139.40 (p-C$_6$H$_3$), 108.75 (m-C$_6$H$_3$), 104.34 (OCH$_2$), 100.62 (o-C$_6$H$_3$), 95.90 (o-C$_6$H$_3$), 51.54, 34.94, 33.03, 32.00, 29.74, 27.06, 22.80, 18.20 (CH$_3$), 14.23 (CH$_3$) ppm.

Figure 17:
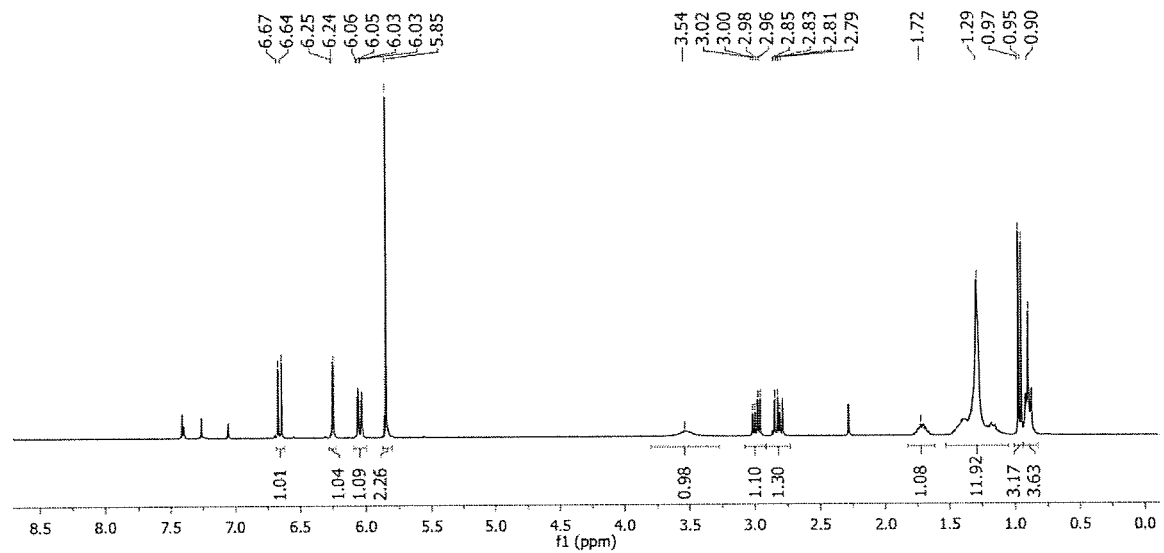
FIG. 17 is a ¹H NMR spectrum (300 MHz, CDCl₃, 298 K) of N-(2-methyloctyl)benzo[d][1,3]dioxol-5-amine.
Figure 18:
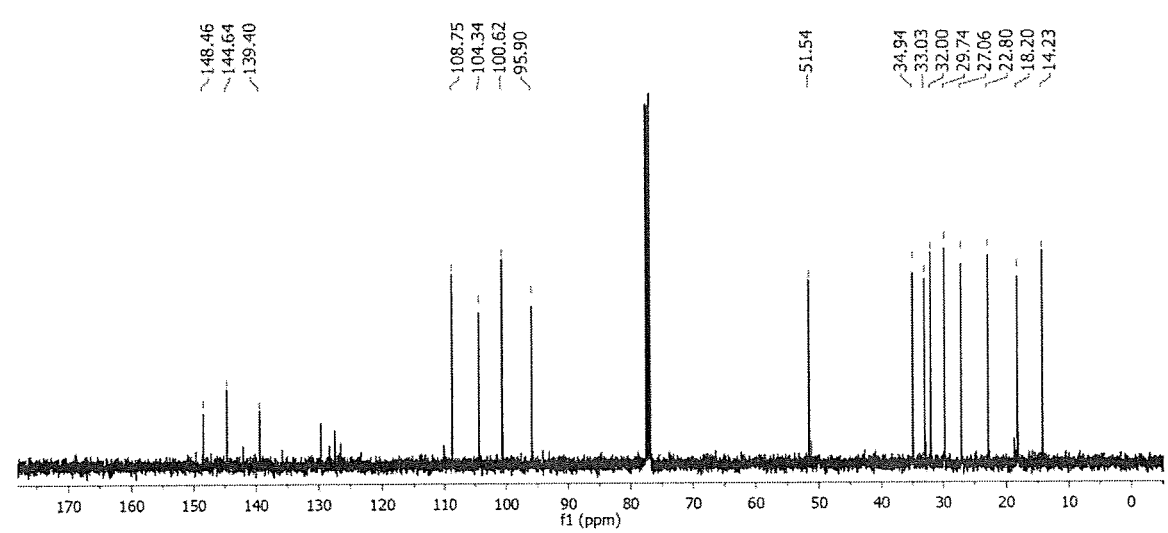
FIG. 18 is a ¹³C NMR spectrum (75 MHz, CDCl₃, 298 K) of N-(2-methyloctyl)benzo[d][1,3]dioxol-5-amine.

FIG. 17 is a $^1$H NMR spectrum (300 MHz, CDCl3, 298 K) of N-(2-methyloctyl)benzo[d][1,3]dioxol-5-amine. FIG. 18 is a $^{13}$C NMR spectrum (75 MHz, CDCl3, 298 K) of N-(2-methyloctypenzo[d][1,3]dioxol-5-amine.

N-(4-((tert-butyldimethylsilyl)oxy)-2-methylbutyl)aniline

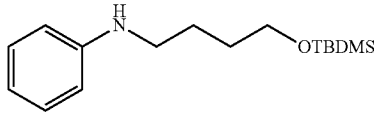 [SMILES: CC(C)(C)[Si](C)(C)OCCCCNc1ccccc1]

N-methylaniline (54 mg, 0.5 mmol), (but-3-en-1-yloxy)(tert-butyl)dimethylsilane (93 mg, 0.5 mmol), Ta(CH$_2$SiMe$_3$)$_3$Cl$_2$ (13 mg, 0.025 mmol), L4 (8 mg, 0.025 mmol). Reaction time: 2 h. Yield 75%. $^1$H NMR (CDCl$_3$, 300 MHz, 298 K): δ 7.20 (t, $^3J_{H-H}$=7.8, 2H, m-C$_6$H$_4$), 6.70 (td, $^3J_{H-H}$=0.9, 7.3, 1H, p-C$_6$H$_4$), 6.63 (d, $^3J_{H-H}$=8.5, 2H, o-C$_6$H$_4$), 3.85 (br s, 1H, NH), 3.83-3.64 (m, 2H, OCH$_2$), 3.10 (dd, J$_{H-H}$=6.3, 12.2 Hz, 1H, NC(H)H), 2.97 (dd, J$_{H-H}$=6.9, 12.2 Hz, 1H, NC(H)H), 1.97 (oct, J$_{H-H}$=6.7 Hz, 1H, OCH$_2$C(H)H), 1.76-1.61 (m, 1H, CHCH$_3$), 1.53-1.39 (m, 1H, OCH$_2$C(H)H), 0.95 (d, J$_{H-H}$=1.3 Hz, 9H, SiC(CH$_3$)$_3$), 0.10 (d, J$_{H-H}$=1.1 Hz, 6H, SiCH$_3$) ppm. $^{13}$C NMR (CDCl$_3$, 75 MHz, 298 K): δ 148.71 (i-C$_6$H$_5$), 129.33 (m-C$_6$H$_5$), 117.00 (p-C$_6$H$_5$), 112.74 (o-C$_6$H$_5$), 77.16 (OCH$_2$), 61.20 (NCH$_2$), 50.43 (OCH$_2$CH$_2$), 37.94, 29.98, 26.10 (SiC(CH$_3$)$_3$), 18.44 (CHCH$_3$), −5.18 (SiCH$_3$) ppm.

Figure 19:
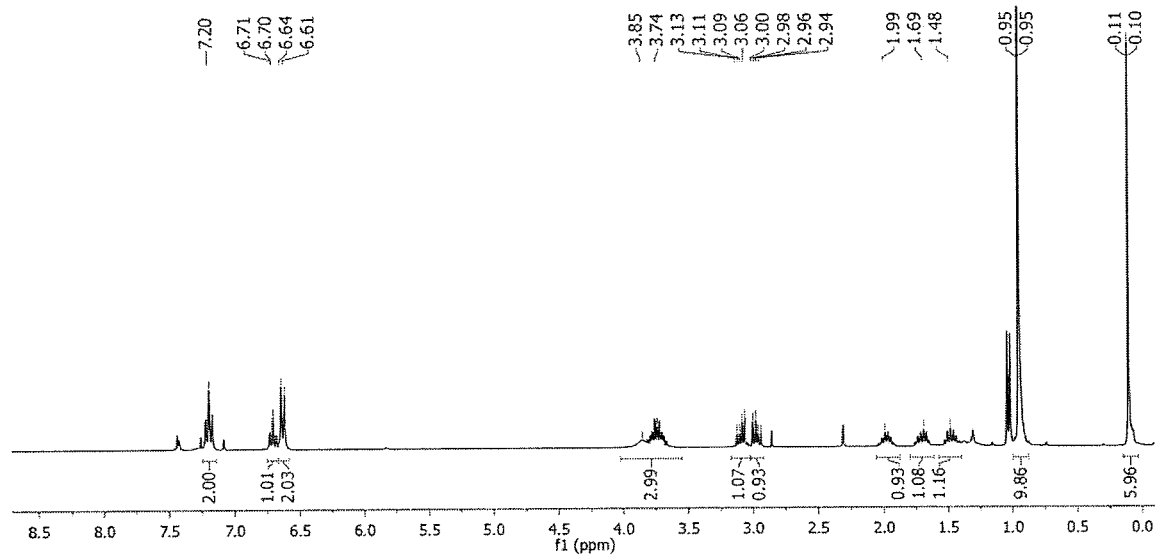
FIG. 19 is a ¹H NMR spectrum (300 MHz, CDCl₃, 298 K) of 4-((tert-butyldimethylsilyl)oxy)-2-methylbutyl)aniline.

FIG. 19: $^1$H NMR spectrum (300 MHz, CDCl3, 298 K) of 4-((tert-butyldimethylsilyl)oxy)-2-methylbutyl)aniline.

Figure 20:
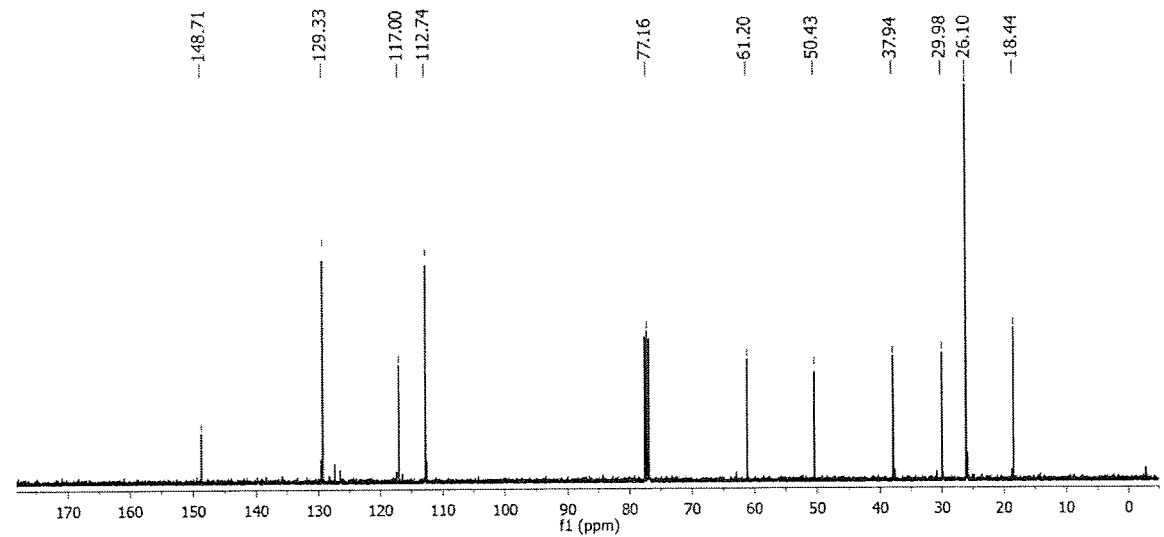
FIG. 20 is a ¹³C NMR spectrum (75 MHz, CDCl₃, 298 K) of 4-((tert-butyldimethylsilyl)oxy)-2-methylbutyl)aniline.

FIG. 20 is a $^{13}$C NMR spectrum (75 MHz, CDCl3, 298 K) of 4-((tert-butyldimethylsilyl)oxy)-2-methylbutyl)aniline.

N-(2-cyclohexylpropyl)aniline

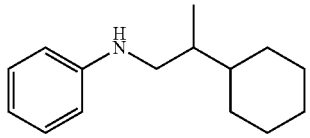 [SMILES: CC(CNc1ccccc1)C1CCCCC1]

N-methylaniline (54 mg, 0.5 mmol), vinylcyclohexane (55 mg, 0.5 mmol), Ta(CH$_2$SiMe$_3$)$_3$Cl$_2$ (13 mg, 0.025 mmol), L4 (8 mg, 0.025 mmol). Reaction time: 2 h. Yield 86%. $^1$H NMR (CDCl$_3$, 300 MHz, 298 K): δ 7.25-7.17 (m, 2H, m-C$_6$H$_4$), 6.79-6.69 (m, 1H, p-C$_6$H$_4$), 6.69-6.63 (m, 2H, o-C$_6$H$_4$) 3.87 (br s, 1H, NH), 3.20 (dd, J$_{H-H}$=5.5, 12.1 Hz, 1H, NC(H)H), 2.93 (dd, J$_{H-H}$=7.9, 12.1 Hz, 1H, NC(H)H), 1.87-1.60 (overlapping m, 6H, CH and CH$_2$$^{Cy}$), 1.47-1.04 (m, 6H, CH$_2$$^{Cy}$), 0.99 (d, J$_{H-H}$=6.9 Hz, 3H, CHCH$_3$) ppm.

N-((1-methylcyclohexyl)methyl)aniline

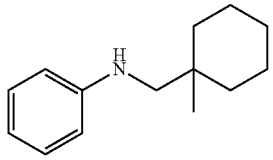

N-methylaniline (54 mg, 0.5 mmol), vinylcyclohexane (48 mg, 0.5 mmol), Ta(CH$_2$SiMe$_3$)$_3$Cl$_2$ (13 mg, 0.025 mmol), L4 (8 mg, 0.025 mmol). Reaction time: 3 h. Yield 99%. $^1$H NMR (CDCl$_3$, 300 MHz, 298 K): δ 7.30-7.21 (m, 2H, m-C$_6$H$_5$), 6.82-6.66 (overlapping m, 3H, o-C$_6$H$_5$ and p-C$_6$H$_5$), 3.68 (br s, 1H, NH), 3.03 (s, 2H, NCH$_2$), 1.69-1.33 (overlapping m, 10H, CH$_2$$^{Cy}$), 1.08 (s, 3H, CH$_3$) ppm.

N-(2-(cyclohex-3-en-1-yl)propyl)aniline

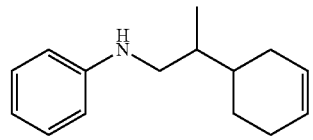 [SMILES: CC(CNc1ccccc1)C1CC=CCC1]

N-methylaniline (54 mg, 0.5 mmol), vinylcyclohexane (55 mg, 0.5 mmol), Ta(CH$_2$SiMe$_3$)$_3$Cl$_2$ (13 mg, 0.025 mmol), L4 (8 mg, 0.025 mmol). Reaction time: 2 h. Yield 98%. $^1$H NMR (CDCl$_3$, 300 MHz, 298 K): δ 7.28-7.17 (m, 2H, m-C$_6$H$_5$), 6.75 (t, J$_{H-H}$=6.8 Hz, 1H, m-C$_6$H$_5$), 6.67 (d, J$_{H-H}$=7.8 Hz, 1H, o-C$_6$H$_5$), 5.75 (s, 2H, CH=CH$_2$), 3.89 (br s, 1H, NH), 3.30-3.18 (m, 1H, NC(H)H), 3.05-2.92 (m, 1H, NC(H)H), 2.25-1.24 (overlapping m, 8H, CHCH$_3$, CH$_2$CH, and CH$_2$), 1.07-0.98 (m, 3H, CH$_3$) ppm. The chemical shifts for the title compound match those reported in the literature.

N-(2-methyl-4-phenylbutyl)aniline

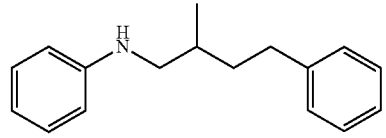 [SMILES: CC(CCc1ccccc1)CNc1ccccc1]

N-methylaniline (54 mg, 0.5 mmol), 4-phenyl-1-butene (66 mg, 0.5 mmol), Ta(CH$_2$SiMe$_3$)$_3$Cl$_2$ (13 mg, 0.025 mmol), L4 (8 mg, 0.025 mmol). Reaction time: 3 h. Yield 87%. $^1$H NMR (CDCl$_3$, 300 MHz, 298 K): δ 7.38-7.28 (m, 2H, m-C$_6$H$_5$), 7.27-7.15 (overlapping m, 5H, m-NC$_6$H$_5$, o-C$_6$H$_5$, and p-C$_6$H$_5$), 6.72 (t, J$_{H-H}$=7.1 Hz, 1H, p-NC$_6$H$_5$), 6.62 (d, J$_{H-H}$=7.9 Hz, 2H, o-NC$_6$H$_5$), 3.69 (br s, 1H, NH), 3.13 (dd, J$_{H-H}$=5.8, 12.3 Hz, 1H, NC(H)H), 2.97 (dd, J$_{H-H}$=6.9, 12.3 Hz, 1H, NC(H)H), 2.84-2.57 (m, 2H, C$_6$H$_5$CH$_2$), 1.92-1.75 (m, 2H, C$_6$H$_5$CH$_2$CH$_2$), 1.64-1.47 (m, 1H, CHCH$_3$), 1.08 (d, J$_{H-H}$=6.6 Hz, 2H, CHCH$_3$) ppm. The chemical shifts for the title compound match those reported in the literature.

N-(2-(4-chlorophenyl)propyl)aniline

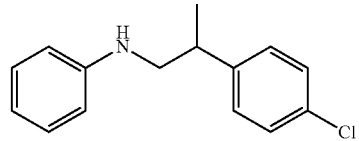 [SMILES: CC(CNc1ccccc1)c1ccc(Cl)cc1]

N-methylaniline (54 mg, 0.5 mmol), 4-chlorostyrene (70 g, 0.5 mmol), Ta(CH$_2$SiMe$_3$)$_3$Cl$_2$ (13 mg, 0.025 mmol), L4 (8 mg, 0.025 mmol). Reaction time: 2 h. Yield 98%. $^1$H NMR (CDCl$_3$, 300 MHz, 298 K): δ 7.31 (d, J$_{H-H}$=8.4 Hz, 2H, m-C$_6$H$_4$C$_1$), 7.23-7.14 (overlapping m, 4H, m-C$_6$H$_4$C$_1$ and o-C$_6$H$_5$), 6.72 (t, J$_{H-H}$=7.2 Hz, 1H, p-C$_6$H$_5$), 6.59 (d, J$_{H-H}$=8.5 Hz, 2H, o-C$_6$H$_5$), 3.59 (br s, 1H, NH), 3.35 (dd, J$_{H-H}$=6.1, 12.5 Hz, 1H, NC(H)H), 3.22 (dd, J$_{H-H}$=8.2, 12.4 Hz, 1H, NC(H)H), 3.13-2.99 (m, 1H, CHCH$_3$), 1.33 (d, J$_{H-H}$=6.9 Hz, 3H, CHCH$_3$) ppm.

N-(2-(2-bromophenyl)propyl)aniline (A) and N-(3-(2-bromophenyl)propyl)aniline (B)

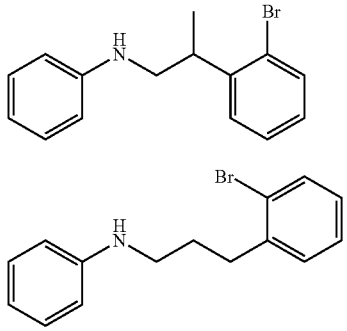

N-methylaniline (54 mg, 0.5 mmol), 2-bromostyrene (92 mg, 0.5 mmol), Ta(CH$_2$SiMe$_3$)$_3$Cl$_2$ (13 mg, 0.025 mmol), L4 (8 mg, 0.025 mmol). Reaction time: 2 h. Yield 65%. $^1$H NMR (CDCl$_3$, 300 MHz, 298 K): Product is a combination of linear and branched HAA products (~9:1), additional spectra are required for full peak assignments.

Figure 21:
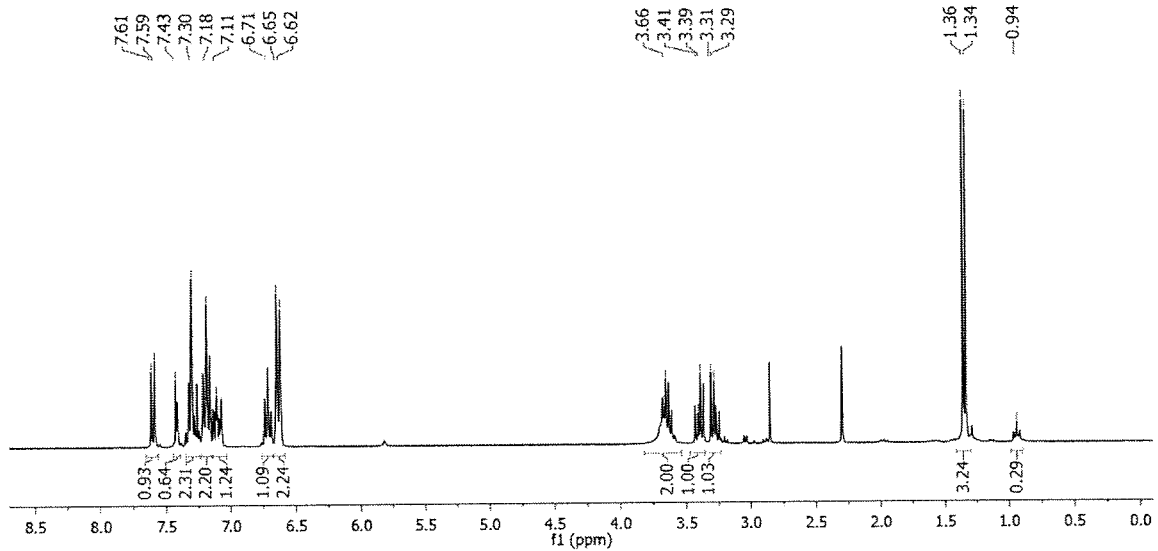
FIG. 21 is a ¹H NMR spectrum (300 MHz, CDCl₃, 298 K) of a mixture between N-(2-(2-bromophenyl)propyl)aniline and N-(3-(2-bromophenyl)propyl)aniline.

FIG. 21 is a $^1$H NMR spectrum (300 MHz, CDCl$_3$, 298 K) of a mixture between N-(2-(2-bromophenyl)propyl)aniline and N-(3-(2-bromophenyl)propyl)aniline.

N-(2-methyl-3-phenylpropyl)aniline (A) and N-(2-phenylbutyl)aniline (B)

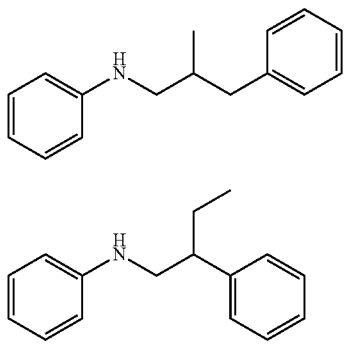

N-methylaniline (54 mg, 0.5 mmol), cis/trans-β-methylstyrene (60 mg, 0.5 mmol), Ta(CH$_2$SiMe$_3$)$_3$Cl$_2$ (13 mg, 0.025 mmol), L5 (8 mg, 0.025 mmol). Reaction time: 48 h. Yield 78%. $^1$H NMR (CDCl$_3$, 300 MHz, 298 K): δ 7.42-7.12 (overlapping m, 14H, m-C$_6$H$_5$$^A$, m-NC$_6$H$_5$$^A$, o,p-C$_6$H$_5$$^A$, o,m,p-C$_6$H$_5$$^B$, and m-NC$_6$H$_5$$^B$), 6.79-6.52 (overlapping m, 6H, p-NC$_6$H$_5$$^A$, o-NC$_6$H$_5$$^A$, p-NC$_6$H$_5$$^B$, and o-NC$_6$H$_5$$^B$), 3.69 (br s, 1H, NH$^A$), 3.60-3.38 (overlapping m, 2H, NH$^B$ and NC(H)H$^B$), 3.30-3.19 (m, 1H, NC(H)H$^B$), 3.13 (dd, J$_{H-H}$=6.0, 12.4 Hz, 1H, NC(H)H$^A$), 2.98 (dd, J$_{H-H}$=6.9, 12.3 Hz, 1H, NC(H)H$^A$), 2.87-2.75 (m, 1H, C$_6$H$_5$CH$^B$), 2.79 (dd, J$_{H-H}$=6.3, 13.4 Hz, 1H, C$_6$H$_5$C(H)H$^A$), 2.53 (dd, J$_{H-H}$=6.3, 13.4 Hz, 1H, C$_6$H$_5$C(H)H$^A$), 2.18-2.03 (m, 1H, CHCH$_3$$^A$), 1.92-1.77 (m, 1H, C(H)HCH$_3$$^B$), 1.77-1.60 (m, 1H, C(H)HCH$_3$$^B$) 1.01 (d, J$_{H-H}$=6.7 Hz, CHCH$_3$$^A$) ppm.

N-(cyclohexylmethyl)aniline

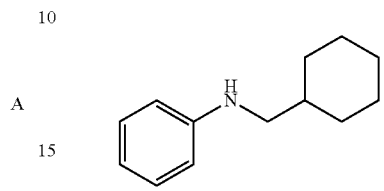

N-methylaniline (54 mg, 0.5 mmol), cyclohexene (41 mg, 0.5 mmol), Ta(CH$_2$SiMe$_3$)$_3$Cl$_2$ (13 mg, 0.025 mmol), L5 (8 mg, 0.025 mmol). Reaction time: 20 h. Yield 70%. $^1$H NMR (CDCl$_3$, 300 MHz, 298 K): δ 7.23-7.11 (m, 1H, m-C$_6$H$_5$), 6.68 (t, J$_{H-H}$=7.2 Hz, 1H, p-C$_6$H$_5$), 6.60 (d, K$_{H-H}$=8.9 Hz, 2H, o-C$_6$H$_5$), 3.70 (br s, 1H, NH), 2.96 (d, J$_{H-H}$=6.7 Hz, NCH$_2$), 1.93-1.67 (m, 5H, CH$_2$), 1.68-1.52 (m, 1H, CH), 1.39-1.21 (m, 3H, CH$_2$), 1.11-0.93 (m, 1H, CH$_2$) ppm. The chemical shifts for the title compound match those previously reported in the literature.[k,l]

N-(cyclopentylmethyl)aniline

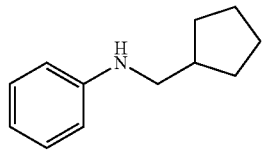 [SMILES: c1ccc(NCC2CCCC2)cc1]

N-methylaniline (54 mg, 0.5 mmol), cyclopentene (34 mg, 0.5 mmol), Ta(CH$_2$SiMe$_3$)$_3$Cl$_2$ (13 mg, 0.025 mmol), L5 (8 mg, 0.025 mmol). Reaction time: 20 h. Yield 74%. $^1$H NMR (CDCl$_3$, 300 MHz, 298 K): δ 7.21 (t, J$_{H-H}$=7.5 Hz, 2H, m-C$_6$H$_5$), 6.72 (t, J$_{H-H}$=7.3 Hz, 1H, p-C$_6$H$_5$), 6.65 (d, J$_{H-H}$=7.7 Hz, 2H, o-C$_6$H$_5$), 3.69 (br s, 1H, NH), 3.06 (d, J$_{H-H}$=7.3 Hz, 2H, NCH$_2$), 2.19 (hept, J$_{H-H}$=7.6 Hz, 1H, NCH$_2$CH), 1.94-1.80 (m, 2H, CH$_2$), 1.77-1.52 (m, 4H, CH$_2$), 1.40-1.23 (m, 2H, CH$_2$) ppm.

N-(cycloheptylmethyl)aniline

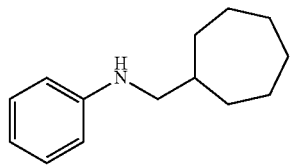 [SMILES: c1ccc(NCC2CCCCCC2)cc1]

N-methylaniline (54 mg, 0.5 mmol), cycloheptene (49 mg, 0.5 mmol), Ta(CH$_2$SiMe$_3$)$_3$Cl$_2$ (13 mg, 0.025 mmol), L5 (8 mg, 0.025 mmol). Reaction time: 6 h. Yield 88%. $^1$H NMR (400 MHz, CDCl$_3$): δ 7.17 (t, J=7.4 Hz, 2H), 6.70 (t, J=7.2 Hz, 1H), 6.62 (d, J=8.0 Hz, 2H), 3.76 (br s, 1H), 2.97 (d, J=6.3 Hz, 2H), 1.90-1.40 (m, 11H), 1.35-1.20 (m, 2H).

EXAMPLES

Various alternative embodiments and examples are described herein. These embodiments and examples are illustrative and should not be construed as limiting the scope of the invention. In particular, while tantalum was used as the representative group 5 metal for these studies, the skilled person will expect other group 5 metals, and especially niobium, to perform similarly.

Example 1: Group 5 Metal-Based Precursors as Catalysts

In order to identify potentially promising group 5 metal/ligand salt combinations, the most common Ta precursors were screened in the absence of any ligand salt (Table 1). For this step, the standard benchmark reaction between N-methylaniline and 1-octene was chosen. It has previously been demonstrated that $TaMe_3Cl_2$ can catalyse this reaction, reaching a conversion of 91%, after 30 hours at 110° C. using a 10 mol % catalyst loading, but full conversion could never be achieved due to catalyst decay. Hence, optimization of the benchmark reaction was started by reducing the reaction time from 24 h to only 1 h. Under these conditions $TaMe_3Cl_2$ could afford a 28% conversion. Further catalytic screening confirmed that Ta-alkyl precursors can competently catalyse the addition of N-methylaniline to 1-octene, with $Ta(CH_2SiMe_3)_3Cl_2$ showing the most promising activity, achieving 39% conversion in only 1 h, when stoichiometric amounts of substrates were used. On the other hand, complexes bearing a Ta—$NMe_2$ moiety were far less reactive, at best showing a 15% conversion after 24 hours of reaction. These data illustrated the promising catalytic activity of $Ta(CH_2SiMe_3)_3Cl_2$. For this reason, $Ta(CH_2SiMe_3)_3Cl_2$ was chosen as the tantalum precursor for all subsequent catalytic experiments.

TABLE 1

Screening of Ta precursors for intermolecular hydroaminoalkylation reactions.[a]

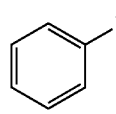

$Ta(CH_2SiMe_3)_3Cl_2$
1 h, 39%
$Ta(CH_2CMe_3)_3Cl_2$
25 h, 15%
$TaMe_3Cl_2$
1 h, 28%
$Ta(NMe_2)_5$
24 h, n.r.
$[Ta(NMe_2)_3Cl_2]_2$
1 h, n.r. 24 h, 15%

[a]Reaction conditions: amine (0.5 mmol), 1-octene (0.5 mmol), [Ta] precatalyst (0.025 mmol), $d_8$ toluene (0.6 mL). Conversion determined by $^1H$ NMR spectroscopy.
n.r. = no reaction.

Example 2: Ligand Salt Screening Using In-Situ Experiments

Further catalytic experiments were performed by generating in situ the catalytic species by reacting $Ta(CH_2SiMe_3)_3Cl_2$ with a variety N,O-chelate type ligand salts.

This study was extended to internal alkenes, adding the more challenging cyclohexene to the pool of substrates. In an effort to perform the catalytic screening under milder conditions, the reaction temperature for reactions using cyclohexene as a substrate were lowered from 145° C. to 130° C. For this step, attention was focussed on amidate (Table 2, L1), phosphoramidate (Table 2, L2), and pyridonate (Table 2, L3) sodium salts. In addition, a variety of ureate type ligand salts were also investigated. The latter type of ligands have previously been studied with group 4 metals for hydroamination and alkyne dimerization catalysis. Catalytic screening of in situ mixtures containing L1 and L2 resulted in no or poor conversion, regardless of the alkene substrate or the chosen reaction time. This behaviour is somewhat surprising considering that in the case of 1-octene, the related amidate-$Ta(NMe_2)_4$ complex gave a 96% conversion of the addition product after 63 h of reaction time. Moreover, the in situ mixture between the ligand salt L2 and $TaMe_3Cl_2$ afforded 52% conversion after 20 h, at room temperature. On the other hand, using the less sterically encumbered pyridonate ligand salt L3 proved to be more successful as 31% and 33% conversions were observed for terminal and internal alkene substrates, respectively.

TABLE 2

Screening of ligand salts in hydroaminoalkylation reactions.[a]

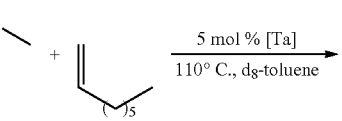

| Ligand Salt | Alkene | | |
|---|---|---|---|
| | | 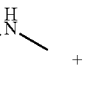 | 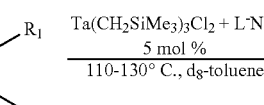 |
| 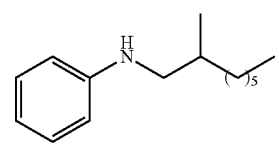 | | L1 1 h, n.r. | 20 h, n.r. |
| 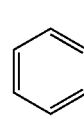 | | L2 1 h, n.r. | 20 h, n.r. |

TABLE 2-continued

Screening of ligand salts in hydroaminoalkylation reactions.[a]

| Ligand Salt | Alkene | 1-octene | cyclohexene |
|---|---|---|---|
| L3 (3-methyl-2-pyridonate Na) | | 1 h, 31% | 20 h, 33% |
| L4 (piperidine-N-carboxamide, 2,6-dimethylphenyl, Na) | | 1 h, 55% | 24 h, 58%[d] |
| L5 (piperidine-N-carboxamide, 2,6-diisopropylphenyl, Na) | | 1 h, 37% | 20 h, 34% |
| L6 (N,N-diphenyl urea, 2,6-dimethylphenyl, Na) | | 1 h, 83% | 20 h, 19% |
| L7 (N-Ph, N-iPr urea, 2,6-dimethylphenyl, Na) | | 1 h, 12% | 20 h, 83% |
| L8 (N,N-diisopropyl urea, 2,6-dimethylphenyl, Na) | | 1 h, 5% | 20 h, 6% |
| L9 (N-Ph, N-Me urea, 2,6-dimethylphenyl, Na) | | 1 h, 48% | 20 h, 45% |
| L10 (N-Cy, N-Me urea, 2,6-dimethylphenyl, Na) | | 1 h, 45% | n/a |
| L11 (N,N-dicyclohexyl urea, 2,6-dimethylphenyl, Na) | | 1 h, traces | n/a |
| L12 (N-cyclohexyl-4-isopropylimidazolidinone Na) | | 1 h, 93% | n/a |
| L13 (N-tert-butyl-4-isopropylimidazolidinone Na) | | 1 h, 92% | n/a |

[a] Reaction conditions: amine (0.5 mmol), alkene (0.5 mmol), Ta(CH$_2$SiMe$_3$)$_3$Cl$_2$ (0.025 mmol), ligand salt (0.025 mmol), d$_8$-toluene (0.5 g). Conversion was determined by $^1$H NMR spectroscopy.
n.r. = no reaction. All reactions with 1-octene were performed at 110° C., while those with cyclohexene were performed at 130° C.

Next, ureate salts were tested. In situ catalyst system with L6 was excellent, affording 83% conversion in only 1 h for the reaction between 1-octene and N-methylaniline with a TOF of more than 16 h$^{-1}$. However, when the more challenging cyclohexene substrate was evaluated, only a modest 19% conversion was observed after 20 h. Remarkably, the mixed aryl/alkyl-substituted ureate ligand L7 resulted in a reversed trend; this system provided higher conversion of the internal alkene substrate (20 h, 83%), but was less effective for the terminal alkene substrate (1 h, 12%). These results are surprising considering that the only change is the N-Ph group of L6 to the N-iPr moiety in L7. Exchanging the remaining Ph group of L7 with an iPr group (L8) did not improve the catalytic system and poor conversions were obtained for both alkenes. Without wishing to be bound by an particular theory, the inventors propose that that the known hemilability of N,O-chelating ligands coupled with the variable coordination modes of ureate ligands results in a flexible coordination environment about the reactive metal center, thereby promoting reactivity.

Table 3 provides additional data with respect to the effect of various ureate ligand salts on the addition of N-methylaniline to 1-octene.

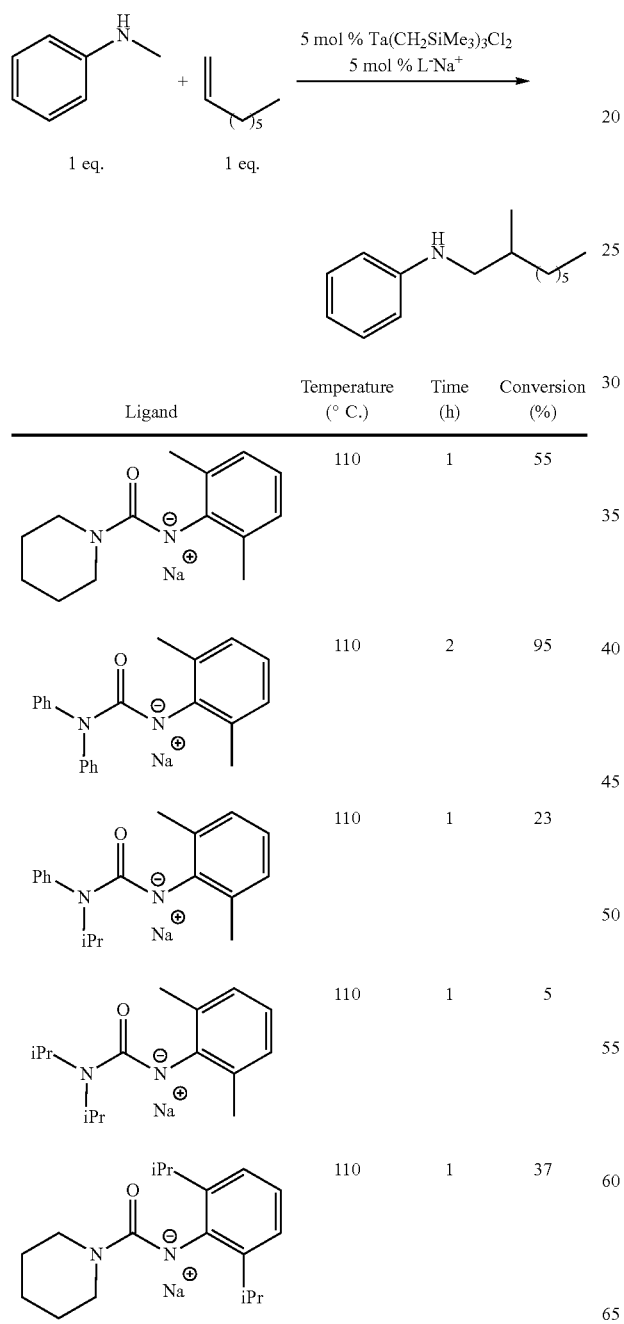

TABLE 3

Screening of ligand salts in hydroaminoalkylation reactions in which N-methylaniline is added to 1-octene.

TABLE 3-continued

Screening of ligand salts in hydroaminoalkylation reactions in which N-methylaniline is added to 1-octene.

TABLE 3-continued

Screening of ligand salts in hydroaminoalkylation reactions in which N-methylaniline is added to 1-octene.

[Reaction scheme: N-methylaniline + 1-octene, 1 eq. each, with 5 mol % Ta(CH₂SiMe₃)₃Cl₂ and 5 mol % L⁻Na⁺, giving PhNH-CH₂-CH(CH₃)-(CH₂)₅-CH₃]

| Ligand | Temperature (° C.) | Time (h) | Conversion (%) |
|---|---|---|---|
| [Urea with Ph, Me, and binaphthyl-CF₃-C₆H₄ substituents] | 110 | 24 | 100 |
| [1-methyl-imidazolidinone Na salt] | 110 | 1 | 31 |
| [1-tert-butyl-imidazolidinone Na salt] | 110 | 0.25 | 67 |
| [1-phenyl-imidazolidinone Na salt] | 110 | 0.5 | 87 |
| [1-cyclohexyl-imidazolidinone Na salt] | 100 | 1 | 93 |
| [1-adamantyl-imidazolidinone Na salt] | 110 | 0.5 | 36 |

Table 4 provides additional data with respect to the effect of various ureate ligand salts on the addition of N-methylaniline to cyclohexene.

TABLE 4

Screening of ligand salts in hydroaminoalkylation reactions in which N-methylaniline is reacted with cyclohexene.

[Reaction scheme: N-methylaniline + cyclohexene, 1 eq. each, with 5 mol % Ta(CH₂SiMe₃)₃Cl₂ and 5 mol % L⁻Na⁺, giving PhNH-CH₂-cyclohexyl]

| Ligand | Temperature (° C.) | Time (h) | Conversion (%) |
|---|---|---|---|
| [piperidine-C(O)-N(Na)-2,6-dimethylphenyl urea] | 145 | 24 | 58 |
| [Ph,Ph-N-C(O)-N(Na)-2,6-dimethylphenyl urea] | 130 | 20 | 35 |
| [Ph,iPr-N-C(O)-N(Na)-2,6-dimethylphenyl urea] | 130 | 20 | 83 |
| [iPr,iPr-N-C(O)-N(Na)-2,6-dimethylphenyl urea] | 145 | 20 | 6 |
| [piperidine-C(O)-N(Na)-2,6-diisopropylphenyl urea] | 145 | 20 | 34 |
| [Ph,Me-N-C(O)-N(Na)-2,6-dimethylphenyl urea] | 130 | 20 | 45 |
| [Cy,Me-N-C(O)-N(Na)-2,6-dimethylphenyl urea] | 130 | 20 | 0 |

TABLE 4-continued

Screening of ligand salts in hydroaminoalkylation reactions in which N-methylaniline is reacted with cyclohexene.

[Reaction scheme: N-methylaniline + cyclohexene → N-(cyclohexylmethyl)aniline, using 5 mol % Ta(CH$_2$SiMe$_3$)$_3$Cl$_2$, 5 mol % L$^-$Na$^+$; 1 eq. + 1 eq.]

| Ligand | Temperature (°C.) | Time (h) | Conversion (%) |
|---|---|---|---|
| [Cy-N(Me)-C(O)-N(Na⁺)-2,6-dimethylphenyl, with Cy on N] | 130 | 20 | 0 |
| [Ph-CH(Me)-N(Me)-C(O)-N(Na⁺)-2,6-dimethylphenyl] | 150 | 20 | 82 |
| [iPr-N(Me)-C(O)-N(Na⁺)-2,6-dimethylphenyl] | 130 | 20 | 20 |
| [Ph$_2$CH-N(Me)-C(O)-N(Na⁺)-2,6-dimethylphenyl] | 130 | 20 | 70 |
| [Ph-CH(Me)-N(Me)-C(O)-N(Na⁺)-2,6-diisopropylphenyl] | 130 | 20 | 42 |

Example 3: Amine Substrate Scope

The study referred to in Tables 2 and 3 was extended by broadening the substrate scope in amine substrates. 1-Octene was kept as the preferred substrate for the terminal alkenes, whereas cyclohexene was swapped with cyclooctene, due to higher reactivity caused by the ring strain. As indicated in Table 5, catalytic mixtures including L6 were used to convert the terminal alkene, while ligand salt L7 was used exclusively for the internal alkene. Another objective was to purify the final products in an easy manner, by avoiding separation on the chromatographic column. For this reason, reaction times were adapted in order to favour full substrate conversion i.e. 2 h for 1-octene and 6 h for cyclooctene. As expected, the reaction between N-methylaniline and 1-octene (Table 5, Entry 1), resulted in a nearly complete conversion of the substrates with a TOF value of 9.5 h$^{-1}$. Likewise, cyclooctene was fully converted within 6 hours, with an average of 3.3 turnovers per hour and an excellent 83% isolated yield (Table 5, Entry 1b). The pyridonate-Ta(NMe$_2$)$_3$Cl$_2$ complex can also catalyse this reaction, but in this case longer reaction times are needed (20 h), with a TOF value limited to 1 h$^{-1}$. Consistently with results reported in the literature, para-substituted N-methylanilines are well tolerated and good TOF values were recorded for both 1-octene (3-3.3 h$^{-1}$) and cyclooctene (8.8-10 h$^{-1}$) substrates. On the same note, the presence of halide substituents on the aromatic ring (Table 5, Entries 3-5) does not inhibit the reaction rates, opening the way for further functionalization via cross-coupling or nucleophilic aromatic substitution reactions. Perhaps more importantly, the potential pharmaceutically relevant aniline N-methyl-4-(trifluoromethoxy) aniline (Table 5, Entry 6) proved to be highly reactive under the specified catalytic conditions. Impressively, the presence of a dioxole unit was also well tolerated, as the corresponding addition product was easily obtained with an 85% yield.

TABLE 5

Substrate scope in amine$^a$

[Reaction scheme: R-substituted N-methylaniline + (a) 1-octene or (b) cyclooctene → branched octylamine product or cyclooctylmethyl aniline product, using Ta(CH$_2$SiMe$_3$)$_3$Cl$_2$, 5 mol % L$^-$Na$^+$, 5 mol %, 110 or 130° C., d$_8$-toluene]

| Entry | Amine | Alkene | Isolated Yield (%) |
|---|---|---|---|
| 1 | N-methylaniline | a | 88 |
| 2 | N-methylaniline | b | 83 |
| 3 | 4-methoxy-N-methylaniline | a | 77 |
| 4 | 4-methoxy-N-methylaniline | b | 70 |

TABLE 5-continued

Substrate scope in amine[a]

R—(C6H4)—NH(Me) + [a: CH2=CH-(CH2)5-CH3  or  b: cyclooctene] → Ta(CH2SiMe3)3Cl2, 5 mol % L⁻Na⁺, 5 mol % / 110 or 130° C., d8-toluene → R—(C6H4)—NH-CH(Me)-(CH2)5-CH3  or  R—(C6H4)—NH-CH2-cyclooctyl

| Entry | Amine | Alkene | Isolated Yield (%) |
|---|---|---|---|
| 5 | 4-Br-C6H4-NH(Me) | a | 86 |
| 6 | 4-Br-C6H4-NH(Me) | b | 95 |
| 7 | 4-Cl-C6H4-NH(Me) | a | 90 |
| 8 | 4-Cl-C6H4-NH(Me) | b | 93 |
| 9 | 4-F-C6H4-NH(Me) | a | 85 |
| 10 | 4-F-C6H4-NH(Me) | b | 88 |
| 11 | 4-F3CO-C6H4-NH(Me) | a | 92 |
| 12 | 4-F3CO-C6H4-NH(Me) | b | 85 |
| 13 | 3,4-methylenedioxy-C6H3-NH(Me) | a | 85 |

[a]Reaction conditions: amine (0.5 mmol), alkene (0.5 mmol), Ta(CH2SiMe3)3Cl2 (0.025 mmol), ligand salt (0.025 mmol), d8-toluene (0.5 g). L4 was used for all terminal alkene substrates at 110° C. over 2 h and L5 was used for internal alkene substrates at 130° C. over 6 h.

Table 6 provides additional data with respect to the addition of various amines to 1-octene in the presence of tantalum metal complexes.

TABLE 6

Amine scope for hydroaminoalkylation reactions.

R1-NH-CHR2(R3) + CH2=CH-R3 → [5 mol % Ta(CH2SiMe3)3Cl2, 5 mol % urea ligand (N,N'-substituted with iPr(Ph) and Ph, Na⁺ salt)] → R1-NH-CH(R2)-CH(R3)-...

1 eq.  1 eq.

| Entry | Amine | Alkene | Temperature (° C.) | Time (h) | Conversion (%) | dr |
|---|---|---|---|---|---|---|
| 1 | 1,2,3,4-tetrahydroisoquinoline | 1-octene | 150 | 20 | 100 | 16:1 |

TABLE 6-continued

Amine scope for hydroaminoalkylation reactions.

| Entry | Amine | Alkene | Temperature (° C.) | Time (h) | Conversion (%) | dr |
|---|---|---|---|---|---|---|
| 2 | 1-phenylpiperazine | 1-heptene | 150 | 20 | 65 | >20:1 |
| 3 | 1,2,3,4-tetrahydroquinoline | 1-heptene | 150 | 20 | | >20:1 |
| 4 | 4-benzylpiperidine | 1-heptene | 150 | 20 | 100 | 10:1 |
| 5 | 3-methylpiperidine | 1-heptene | 150 | 20 | 100 | >20:1 |
| 6 | 4-methylpiperidine | 1-heptene | 150 | 20 | 100 | 8:1 |
| 7 | azepane | 1-heptene | 150 | 20 | 100 | >20:1 |
| 8 | 2,2-diphenyl-N-methylpent-4-en-1-amine | n/a | 150 | 20 | 100 | n/a |
| 9 | N-methylbenzylamine | 1-heptene | 150 | 20 | 100 | 1:1 regioisomers dr >20:1 |
| 10 | piperidine | 4-vinylcyclohexene | 150 | 20 | 100 | >20:1 |

TABLE 6-continued

Amine scope for hydroaminoalkylation reactions.

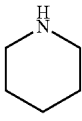

| Entry | Amine | Alkene | Temperature (° C.) | Time (h) | Conversion (%) | dr |
|---|---|---|---|---|---|---|
| 11 | 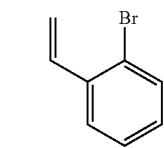 |  | 110 | 20 | 90 | TBD |
| 12 | 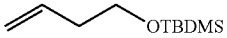 | 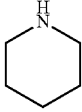 | 150 | 20 | 100 | dr TBD |
| 13 | 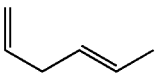 |  | 150 | 20 | 50 | dr TBD |
| 14 |  | 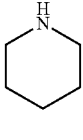 | 150 | 2 | 100 | >20:1 Mostly bis-alkylated product obtained |
| 15 | 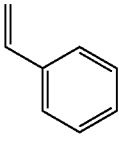 |  | 150 | 20 | 100 | 1.79:1 (Branched:Linear regioisomers) dr 17:1 |
| 16 | | 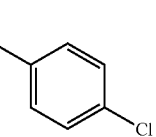 | 150 | 20 | 100 | 1.2:1 (Branched:Linear regioisomers) dr 19:1 |

Example 4: Alkene Substrate Scope

Having tested the capability of the $Ta(CH_2SiMe_3)_3Cl_2$ containing catalytic system in broadening the substrate scope in amines, attention was switched to the alkene class of substituents (Table 7). In this respect, a variety of terminal, di-substituted alkenes and dienes were chosen as candidates. As before, L6 was used exclusively for terminal alkenes, while L7 was used in the case of the internal ones. Alkenes containing silyl protected OH moieties were easily reacted with N-methylaniline in less than 2 h to give the addition product in a 75% yield, and with an average of 8.6 turnovers per hour. Further catalytic screenings involved trimethyl(vinyl)silane, which upon reaction with N-methylaniline gives a 1:1 mixture (TOF=9.0 $h^{-1}$) between the branched and linear product, perhaps as a consequence of the β-silicon effect. Even sterically hindered alkenes such as vinylcyclohexene and methylenecyclohexane are accommodated giving the corresponding addition products in excellent yields and TOF values of 9.1 $h^{-1}$ and 6.6 $h^{-1}$, respectively. Remarkably, 4-vinylcyclohex-1-ene was highly reactive under catalytic conditions (99% yield, TOF=10 $h^{-1}$), when only the terminal C=C bond was selectively activated. This result is impressive as isolated dienes are particularly difficult to convert. Styrenes are no exception to the active class of substituents as 4-chlorostyrene and 2-bromo-styrene reacted quantitatively (TOF=10 and 10 $h^{-1}$) with the amine, with no signs of polymerized product being observed. In the case of 2-bromo-styrene, the presence of the halide atom in the ortho position on the aryl ring notably does not sterically affect the outcome of the reaction.

This observation is counterintuitive considering that under identical conditions, 2-methylstyrene was found to be completely inert.

The substrate scope containing the more challenging internal alkenes was investigated next. First, α-methylstyrene required long reaction times (48 h) to ensure an almost complete conversion. α-methylstyrene can be fully converted in 24 h when the catalyst is supported by the smaller pyridonate type of ligands. The reactivity of cyclic internal alkenes was found to be directly proportional to the size of the ring, and therefore dependant on the ring strain. Hence, cyclooctene was found to be the most reactive (TOF=3.2 h$^{-1}$), followed by cycloheptene (TOF=3 h$^{-1}$), while cyclopentene (TOF=0.79 h$^{-1}$) and cyclohexene (TOF=0.80 h$^{-1}$) displayed a similar reactivity. Absence of the ring strain, as observed for the internal linear alkenes had a clear impact on the reactivity of these substrates. Indeed, compared to the cyclic alkenes, only moderate yields were obtained after 20 h i.e. 4-octene (55%), cis-3-hexene (55%), trans-3-hexene (32%).

TABLE 7

Substrate scope in alkene.$^{a,b}$ Turnover frequency values (h$^{-1}$) are given in brackets. Ratio of branched:linear regioisomers are given in square brackets TABLE 7-continued Substrate scope in alkene.$^{a,b}$ Turnover frequency values (h$^{-1}$) are given in brackets. Ratio of branched:linear regioisomers are given in square brackets

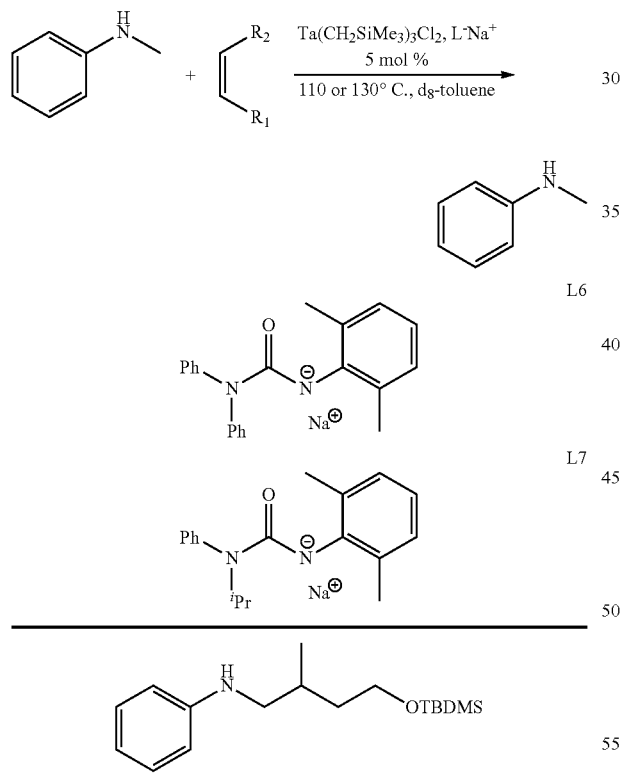

TABLE 7-continued
Substrate scope in alkene.[a,b] Turnover frequency values (h[−1]) are given in brackets. Ratio of branched:linear regioisomers are given in square brackets
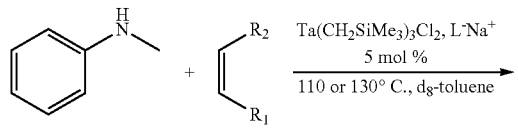
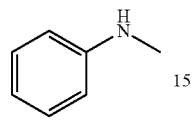
L6
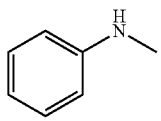
L7
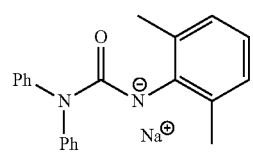
75% (0.79)
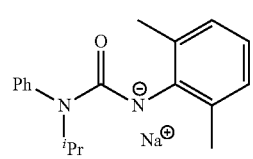
55% (0.6)
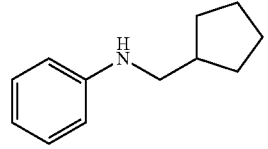
86% (9.1)
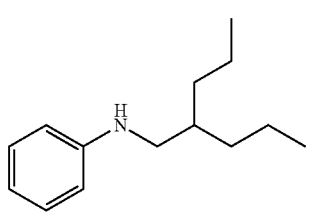
98% (10)
TABLE 7-continued
Substrate scope in alkene.[a,b] Turnover frequency values (h[−1]) are given in brackets. Ratio of branched:linear regioisomers are given in square brackets
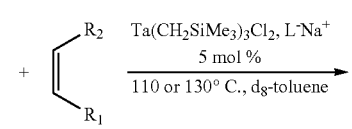
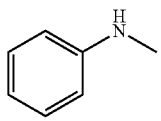
L6
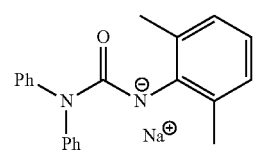 [SMILES: Cc1cccc(C)c1[N-]C(=O)N(c1ccccc1)c1ccccc1 ; [Na+]]
L7
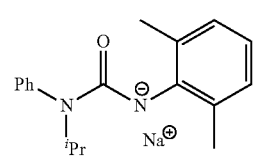 [SMILES: Cc1cccc(C)c1[N-]C(=O)N(c1ccccc1)C(C)C ; [Na+]]
70% (0.8)
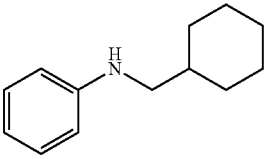
55% (0.8)
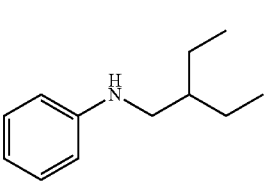
99% (6.6)
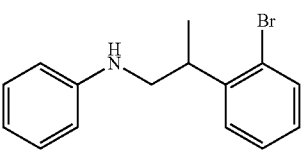
65% (10)

TABLE 7-continued

Substrate scope in alkene.[a,b] Turnover frequency values (h$^{-1}$) are given in brackets. Ratio of branched:linear regioisomers are given in square brackets

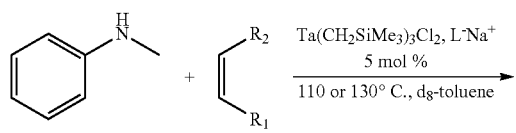

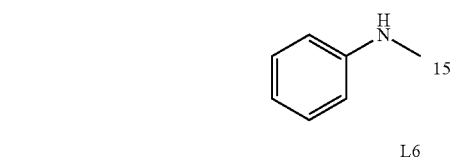 L6

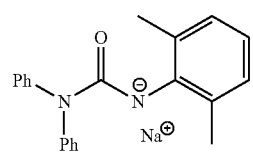 L7

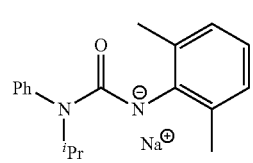

95% (3)

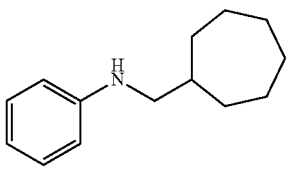

32% (0.5)

[a]Reaction conditions: amine (0.5 mmol), alkene (0.5 mmol), Ta(CH$_2$SiMe$_3$)$_3$Cl$_2$ (0.025 mmol), ligand salt (0.025 mmol), d$_8$-toluene (0.5 g). Conversion determined by $^1$H NMR spectroscopy. All reactions with terminal alkene substrates we're performed with L6 at 110° C. Reactions with internal alkene substrates were performed with L7 at 130° C.
[b]Major isomer presented, yield refers to combined regioisomers.

Table 8 provides additional data with respect to the addition of N-methyl butylamine to various alkenes.

TABLE 8

Addition of various alkenes to N-methyl butylamine.

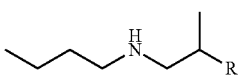

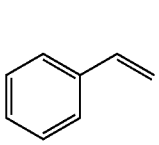

| Entry | Alkene | Temperature (° C.) | Time (h) | Conversion (%) |
|---|---|---|---|---|
| 1 | ⟶SiMe$_3$ | 110 | 24 | 94 |
| 2 | cyclohexyl-CH=CH$_2$ | 145 | 24 | 94 |
| 3 | styrene | 110 | 24 | 50 |
| 4 | ⟶OTBDMS | 145 | 24 | 0 |
| 5 | allylbenzene | 145 | 1 | 0 |
| 6 | 1,5-hexadiene | 145 | 24 | 78 |

Table 9 provides additional data with respect to the effect of various ureate ligand salts and metal complexes on the addition of piperidine to styrene.

TABLE 9
Screening of ligand salts in hydroaminoalkylation reactions in which piperidine is reacted with styrene.
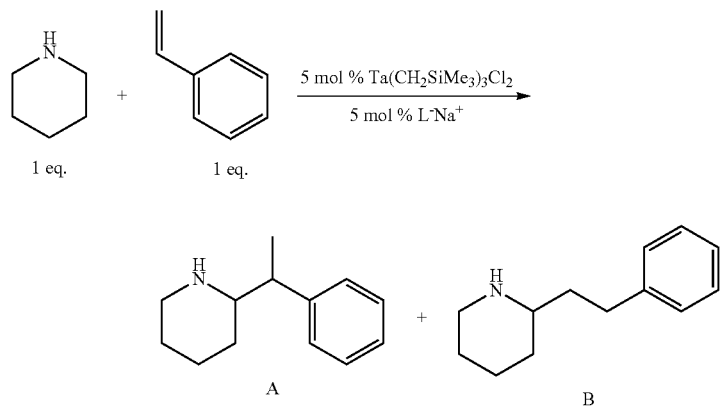
| Entry | Ligand | Temperature (° C.) | Time (h) | Percent Conversion | A:B | dr |
|---|---|---|---|---|---|---|
| 1 | Ph-N(Ph)-C(O)-N(Na⁺)-(2,6-dimethylphenyl) | 150 | 20 | 100 | 1.71:1 | 16:1 |
| 2 | piperidinyl-C(O)-N(Na⁺)-(2,6-diisopropylphenyl) | 150 | 20 | 100 | 2:1 | 20:1 |
| 3 | Me(iPr)N-C(O)-N(Na⁺)-(2,6-dimethylphenyl) | 150 | 20 | 100 | 2.2:1 | 18:1 |
| 4 | Me(CHPh₂)N-C(O)-N(Na⁺)-(2,6-dimethylphenyl) | 150 | 20 | 100 | 1.7:1 | 15:1 |
| 5 | Me(CHMePh)N-C(O)-N(Na⁺)-(2,6-diisopropylphenyl) | 150 | 20 | 100 | 1.4:1 | 18:1 |

Example 5: Hydroamination Reaction Between Piperidine and 1-Octene

Tables 10 and 11 provide data with respect to the effect of various ureate ligand salts and metal complexes on the addition of piperidine to 1-octene.

TABLE 10

Hydroaminoalkylation data using cyclic ureate salts and Ta(CH₂SiMe₃)₃Cl₂ for the reaction between piperidine and 1-octene.

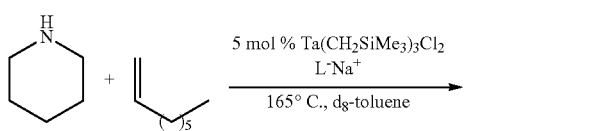

| Ligand salt | Time (h) | Conversion (%) |
|---|---|---|
|  | 144 | 100 |
| 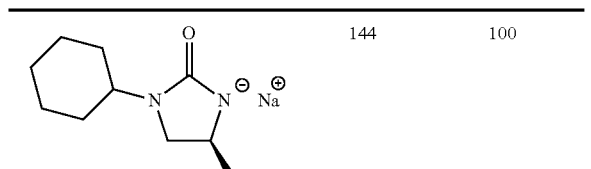 | 144 | 100 |

| Ligand | Temperature (° C.) | Time (h) | Conversion (%) |
|---|---|---|---|
| 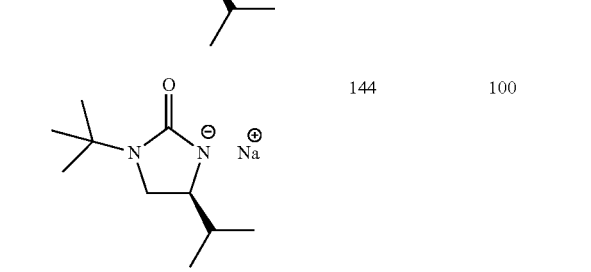 | 150 | 6 | 0 |
| 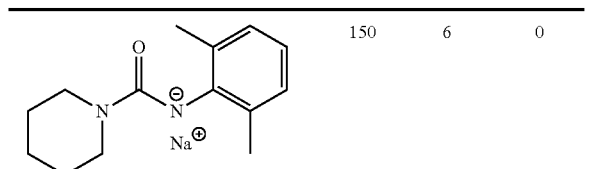 | 150 | 6 | 100 |
| 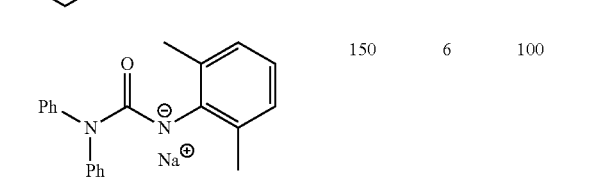 | 150 | 6 | 100 |

TABLE 10-continued

Hydroaminoalkylation data using cyclic ureate salts and Ta(CH₂SiMe₃)₃Cl₂ for the reaction between piperidine and 1-octene.

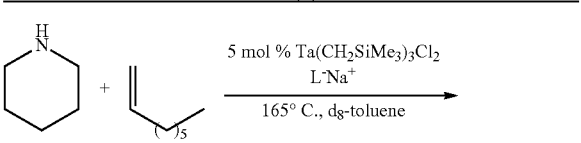

| | | | |
|---|---|---|---|
| 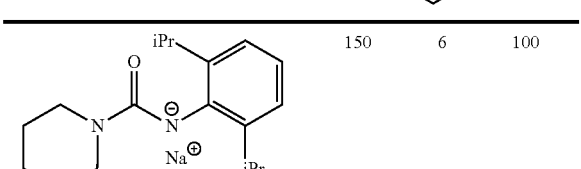 | 150 | 6 | 100 |
| 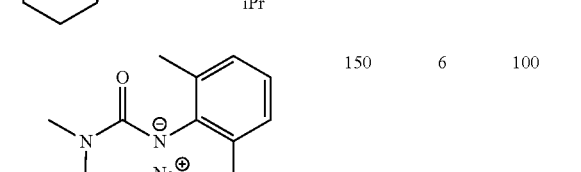 | 150 | 6 | 100 |
| 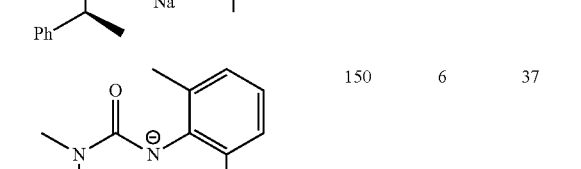 | 150 | 6 | 37 |

Example 6. Effect of Temperature on Hydroaminoalkylation

Figure 43:
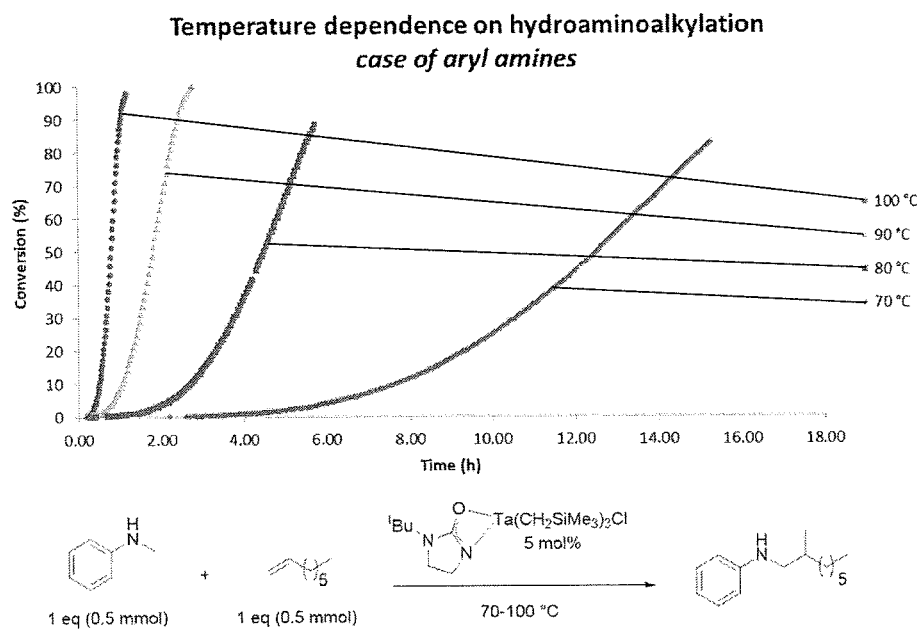
FIG. 43 is a graph showing the effect of reaction temperature on hydroaminoalkylation for an aryl amine.
Figure 44:
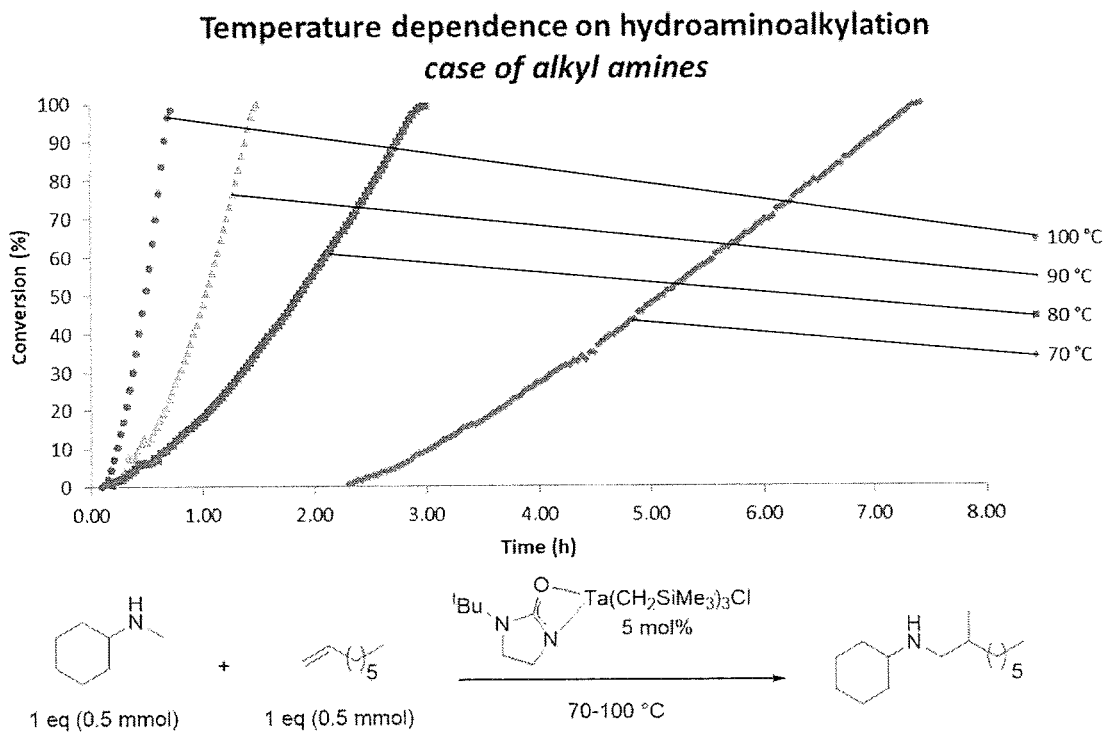
FIG. 44 is a graph showing the effect of reaction temperature on hydroaminoalkylation for an alkyl amine.

FIGS. 43 and 44 illustrate that the rate of the hydroaminoalkylation reaction for aryl and alkyl amines with 1-octene in the presence of metal complexes disclosed herein is temperature dependent and increases with temperature from 70° C. to 100° C.

Example 8. Effect of Catalyst Concentration on Hydroaminoalkylation

Figure 45:
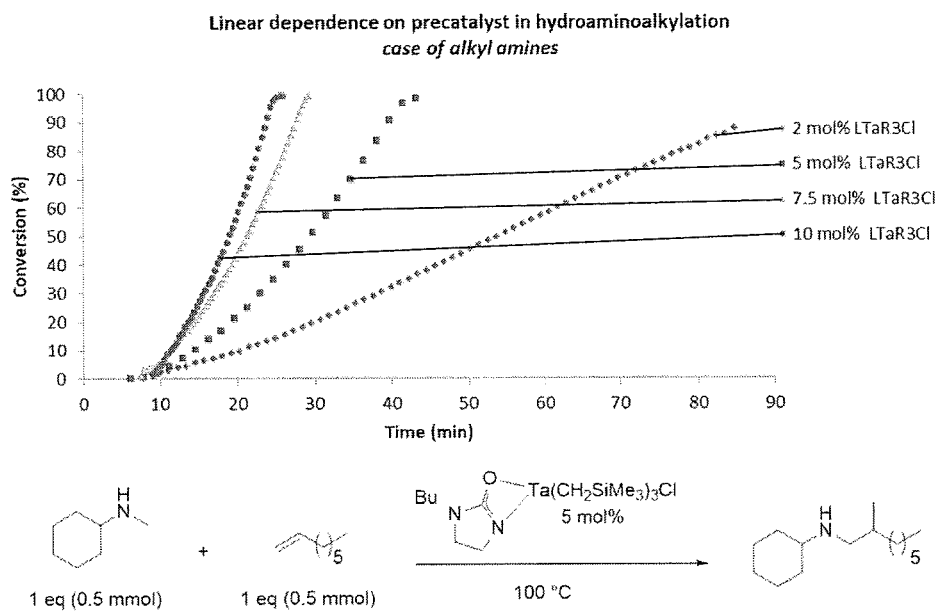
FIG. 45 is a graph showing the effect of precatalyst concentration on hydroaminoalkylation for an alkyl amine.

FIG. 45 illustrates that the rate of the hydroaminoalkylation reaction for alkyl amines with 1-octene in the presence of metal complexes disclosed herein is concentration dependent and increases with concentration 2 mol % to 10 mol %.

Example 7. Effect of Halide Salts on Hydroaminoalkylation

Figure 46:
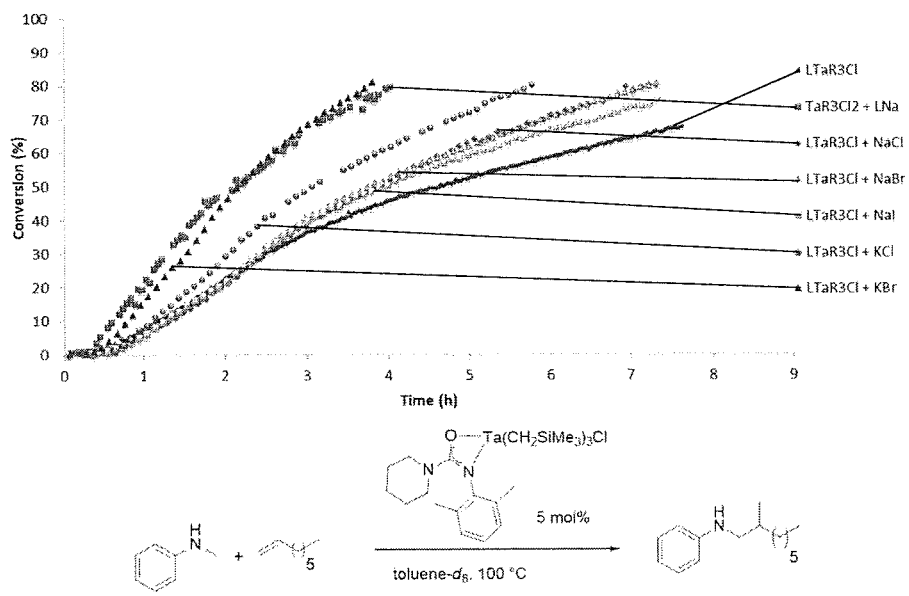
FIG. 46 is a graph showing the effect of Lewis acid salts on hydroaminoalkylation for an aryl amine.
Figure 47:
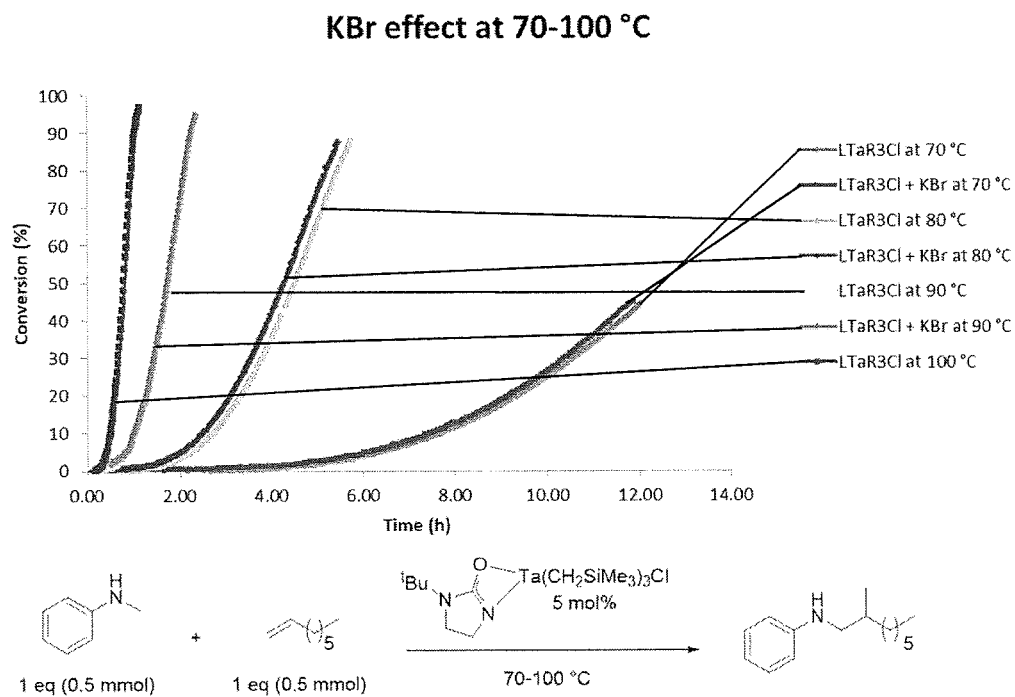
FIG. 47 is a graph showing the effect of KBr on hydroaminoalkylation for an aryl amine at different temperatures.
Figure 48:
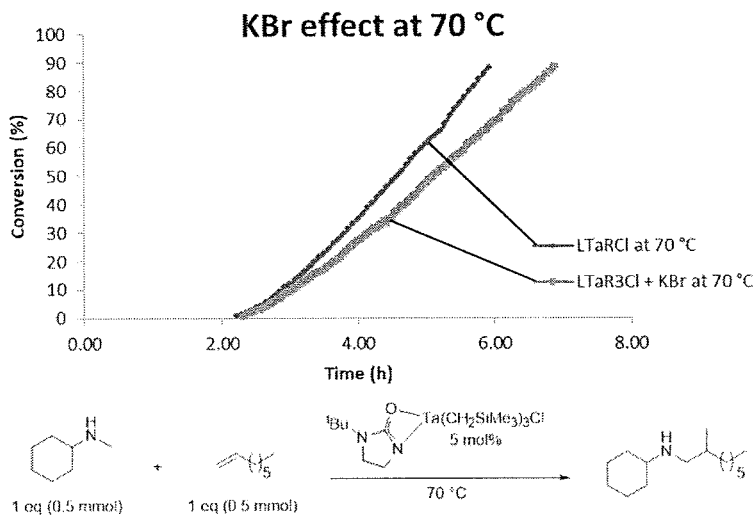
FIG. 48 is a graph showing the effect of KBr on hydroaminoalkylation for an alkyl amine.

FIG. 46 illustrates that the rate of the hydroaminoalkylation reaction for aryl amines with 1-octene in the presence of metal complexes disclosed herein increases with the addition of halide salts. FIGS. 47 and 48 demonstrate that the rate of the hydroaminoalkylation reaction for aryl amines with 1-octene in the presence of metal complexes disclosed herein increases with the addition of KBr at temperatures from 70° C. to 100° C.

Operation

While specific embodiments of the invention have been described and illustrated, such embodiments should be considered illustrative of the invention only and not as limiting the invention as construed in accordance with the accompanying claims.

What is claimed is:

1. A metal complex having the structure of Formula I:

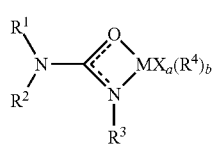

(Formula I)

wherein:

(i) $R^1$ and $R^2$ are each independently H; a $C_1$-$C_{40}$ substituted or unsubstituted linear, branched or cyclic alkyl, alkenyl or alkynyl; a substituted or unsubstituted aryl; or a substituted or unsubstituted heterocyclic group; or $R^1$ and $R^2$ are bonded together thereby forming, together with the nitrogen atom they are both bound to, a heterocycle; and $R^3$ is H; a $C_1$-$C_{40}$ substituted or unsubstituted linear, branched or cyclic alkyl, alkenyl or alkynyl; a substituted or unsubstituted aryl; or a substituted or unsubstituted heterocyclic group; or (ii) $R^1$ is H; a $C_1$-$C_{40}$ substituted or unsubstituted linear, branched or cyclic alkyl, alkenyl or alkynyl; a substituted or unsubstituted aryl; or a substituted or unsubstituted heterocyclic group; and $R^3$ is bonded together with $R^2$ to form a heterocycle;

M is a group 5 metal;

a=1 or 2 and b=2 or 3, wherein the sum of a and b is 4;

each X is a halogen substituent; and each $R^4$ is independently H; or a $C_1$-$C_{20}$ substituted or unsubstituted, linear, branched or cyclic alkyl, optionally comprising heteroatoms.

2. The metal complex of claim 1, wherein each X is independently Cl or Br, a=1 and b=3.

3. The metal complex of claim 1, wherein $R^1$ and $R^2$ are bonded together to form, together with the nitrogen atom they are both bound to, a 6-membered ring, which optionally may be substituted.

4. The metal complex of claim 1, wherein:

$R^1$ and $R^2$ are each phenyl;

$R^1$ is phenyl and $R^2$ is isopropyl;

$R^1$ and $R^2$ are bonded together to form, together with the nitrogen atom they are both bound to, piperidinyl;

$R^1$ is phenyl and $R^2$ is methyl;

$R^1$ is methyl and $R^2$ is 1-phenylethyl;

$R^1$ is methyl and $R^2$ is isopropyl; or $R^1$ is methyl and $R^2$ is diphenylmethyl.

5. The metal complex of claim 1, wherein $R^3$ is: phenyl; 2,6-dimethyl phenyl; 2,6-di(isopropyl) phenyl; or

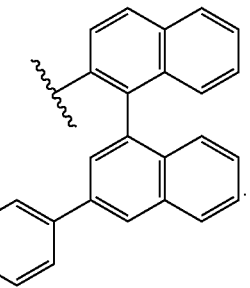

6. The metal complex of claim 1, wherein $R^3$ is bonded together with $R^2$ to form, together with each of the nitrogen atoms they are bound to, a 5-membered ring, which optionally may be substituted.

7. The metal complex of claim 6, having the structure:

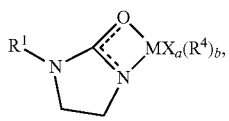

wherein $R^1$ is methyl, tert-butyl, phenyl, cyclohexyl or adamantyl.

8. The metal complex of claim 1, wherein $R^4$ is —$CH_2Si(CH_3)_3$.

9. The metal complex of claim 1, wherein M is tantalum (Ta).

10. The metal complex of claim 1, which metal complex is:

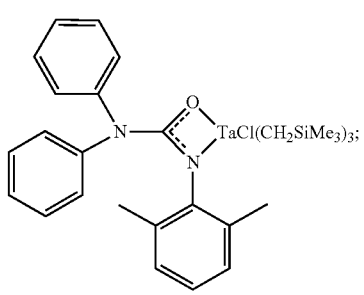

(Formula III)

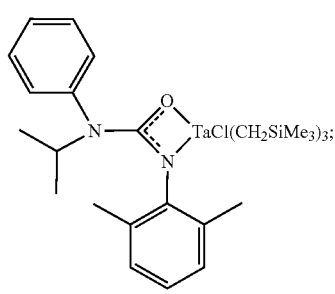

Formula (IV)

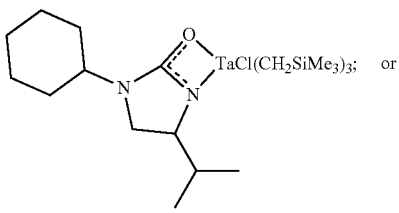

(Formula V)

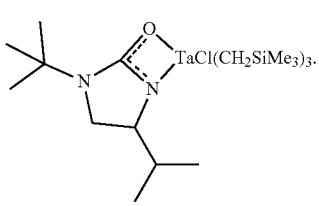

(Formula VI)

11. A method of synthesizing a metal complex of Formula I, the method comprising reacting a group 5 metal salt of Formula VII with one equivalent of an amide of Formula VIII according to the following reaction:

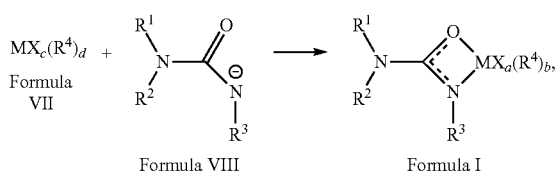

wherein:
(i) $R^1$ and $R^2$ are each independently H; a $C_1$-$C_{40}$ substituted or unsubstituted linear, branched or cyclic alkyl, alkenyl or alkynyl; a substituted or unsubstituted aryl; or a substituted or unsubstituted heterocyclic group; or
$R^1$ and $R^2$ are bonded together thereby forming, together with the nitrogen atom they are both bound to, a heterocycle; and
$R^3$ is H; a $C_1$-$C_{40}$ substituted or unsubstituted linear, branched or cyclic alkyl, alkenyl or alkynyl; a substituted or unsubstituted aryl; or a substituted or unsubstituted heterocyclic group; or
(ii) $R^1$ is H; a $C_1$-$C_{40}$ substituted or unsubstituted linear, branched or cyclic alkyl, alkenyl or alkynyl; a substituted or unsubstituted aryl; or a substituted or unsubstituted heterocyclic group; and
$R^3$ is bonded together with $R^2$ to form a heterocycle;
M is a group 5 metal;
a=1 or 2 and b=2 or 3, wherein the sum of a and b is 4;
c=2 or 3 and d=2 or 3, wherein the sum of c and d is 5;
each X is a halogen substituent; and
each $R^4$ is independently H; or a $C_1$-$C_{20}$ substituted or unsubstituted, linear, branched or cyclic alkyl, optionally comprising heteroatoms.

12. A method for α-alkylation of a secondary amine-containing moiety, the method comprising: (i) reacting said secondary amine-containing moiety with an olefin in the presence of a metal complex as defined in claim 1.

13. The method of claim 12, further comprising: (ii) isolating a product formed in step (i).

14. The method of claim 12, wherein the secondary amine-containing moiety is a $C_4$-$C_{100}$ linear, branched, or cyclic alkyl, optionally substituted and/or comprising heteroatoms.

15. The method of claim 12, wherein the secondary amine-containing moiety is substituted with a halogen, an ether, another amine, an alkyl, an alkene, an acetal, a phosphine, an amide, an alkyne, an imine, a nitrile, an isocyanide, an epoxide, a boronic acid ester, a phenyl that optionally may be substituted and/or part of a condensed ring system, or any combination thereof.

16. The method of claim 12, wherein the olefin is:

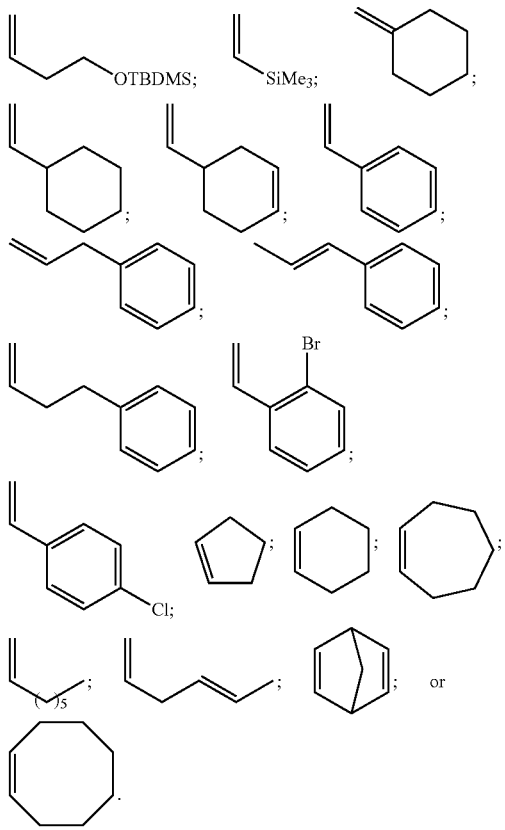

17. The method of claim 12, wherein the secondary amine-containing moiety is: pyrrolidine;

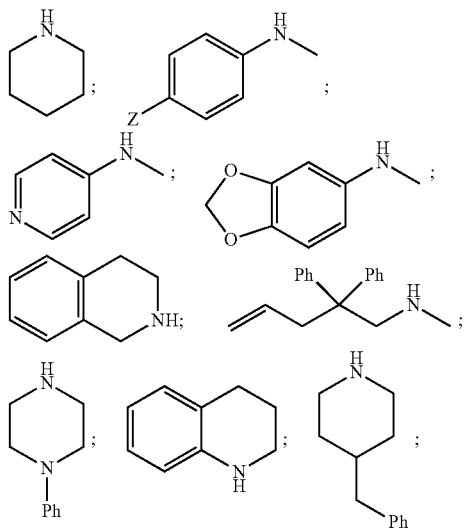

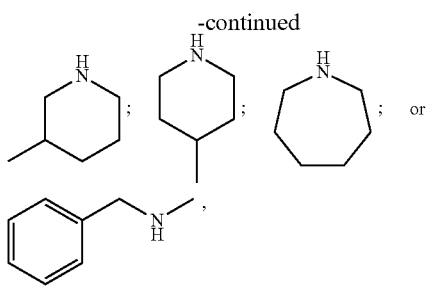

wherein Z is H, OCF$_3$, F, Cl, Br, I, or OCH$_3$.

18. The method of claim 12, wherein the reaction conditions comprise a reaction temperature in the range from 90° C. to 150° C.

19. The method of claim 12, wherein the reaction conditions comprise a solvent, wherein the solvent is toluene, benzene, or a mixture thereof.

20. The method of claim 12, wherein the metal complex is generated in situ from a group 5 metal salt of Formula VII MX$_c$(R$^4$)$_d$     (Formula VII)

wherein:
M is a group 5 metal;
c=2 or 3 and d=2 or 3, wherein the sum of c and d is 5; and
each R$^4$ is independently H; or a C$_1$-C$_{20}$ substituted or unsubstituted, linear, branched or cyclic alkyl, optionally comprising heteroatoms, in combination with an amide of Formula VIII

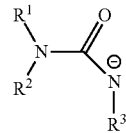

(Formula VIII)

wherein:
(i) R$^1$ and R$^2$ are each independently H; a C$_1$-C$_{40}$ substituted or unsubstituted linear, branched or cyclic alkyl, alkenyl or alkynyl; a substituted or unsubstituted aryl; or a substituted or unsubstituted heterocyclic group; or R$^1$ and R$^2$ are bonded together thereby forming, together with the nitrogen atom they are both bound to, a heterocycle; and
R$^3$ is H; a C$_1$-C$_{40}$ substituted or unsubstituted linear, branched or cyclic alkyl, alkenyl or alkynyl; a substituted or unsubstituted aryl; or a substituted or unsubstituted heterocyclic group; or
(ii) R$^1$ is H; a C$_1$-C$_{40}$ substituted or unsubstituted linear, branched or cyclic alkyl, alkenyl or alkynyl; a substituted or unsubstituted aryl; or a substituted or unsubstituted heterocyclic group; and
R$^3$ is bonded together with R$^2$ to form a heterocycle.

\* \* \* \* \*